United States Patent
Park et al.

(10) Patent No.: US 8,501,175 B2
(45) Date of Patent: Aug. 6, 2013

(54) TMPRSS4-SPECIFIC HUMAN ANTIBODY

(75) Inventors: Young Woo Park, Daejeon (KR);
So-Young Choi, Daejeon (KR);
Young-Soon Jang, Daejeon (KR); Ji Hyun Park, Daejeon (KR); Eun-Jung Song, Daejeon (KR); Jung Yu, Daejeon (KR); Myung-Ho Sohn, Daejeon (KR); Jae Won Jeon, Daejeon (KR); Joon-Goo Jung, Daejeon (KR); Sungsub Kim, Daejeon (KR); Myeoung Hee Jang, Daejeon (KR)

(73) Assignee: Korea Research Institute of Bioscience and Biotechnology (KR)

( * ) Notice: Subject to any disclaimer, the term of this patent is extended or adjusted under 35 U.S.C. 154(b) by 221 days.

(21) Appl. No.: 13/124,603

(22) PCT Filed: Nov. 10, 2008

(86) PCT No.: PCT/KR2008/006614
§ 371 (c)(1),
(2), (4) Date: Apr. 15, 2011

(87) PCT Pub. No.: WO2010/044506
PCT Pub. Date: Apr. 22, 2010

(65) Prior Publication Data
US 2011/0189087 A1 Aug. 4, 2011

(30) Foreign Application Priority Data
Oct. 16, 2008 (KR) .................. 10-2008-0101575

(51) Int. Cl.
*C07K 16/00* (2006.01)
(52) U.S. Cl.
USPC ............... 424/133.1; 424/138.1; 424/174.1; 530/387.3; 530/387.7

(58) Field of Classification Search
None
See application file for complete search history.

(56) References Cited

FOREIGN PATENT DOCUMENTS

| WO | WO 2004/097034 | 11/2004 |
|---|---|---|
| WO | WO 2007/139260 | 12/2007 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Freshney (Culture of Animal Cells, A Manual of Basic Technique, Alan R. Liss, Inc., 1983, New York, p. 4.*
Dermer (Bio/Technology, 1994, 12:320).*
Gura (Science, 1997, 278:1041-1042).*
Jain (Sci. Am., 1994, 271:58-65).*
International Search Report prepared by the Korean Intellectual Property Office dated Apr. 27, 2009, for International Application No. PCT/KR2008/006614.
Jung, H. et al. "TMPRSS4 promotes invasion, migration and metastasis of human tumor cells by facilitating an epithelial mesenchymal transition." Oncogene 2008. vol. 27 (18); pp. 2635-2647.
Choi, S. Y. et al. "Role of TMPRSS4 during cancer progression." Drug News and Perspectives. Oct. 2008. vol. 21(8); pp. 417-423.

* cited by examiner

*Primary Examiner* — Sheela J Huff
(74) *Attorney, Agent, or Firm* — Sheridan Ross P.C.

(57) ABSTRACT

The present invention relates to a transmembrane protease, serine (TMPRSS4)-specific human antibody, and more particularly to a human antibody including a complementarity determining region (CDR) and a framework region (FR) derived from a human antibody specifically bound to TMPRSS4. The TMPRSS4-specific human antibody expressed in the various kinds of cancer cells of the present invention may be used in diagnosis of the cancer, classification of the disease, visualization, treatment, and prognostic evaluation.

12 Claims, 13 Drawing Sheets

Lane1: MW Marker
Lane2: whole cell lysate
Lane3: soluble fraction from whole cell lysate
Lane4: supernatant of inclusion body wash with PBS
Lane5: supernatant of inclusion body wash with 2M urea
Lane6: inclusion body
Lane7: His-tag purified 2XFLAG-TMPRSS4
Lane8: after dialysis

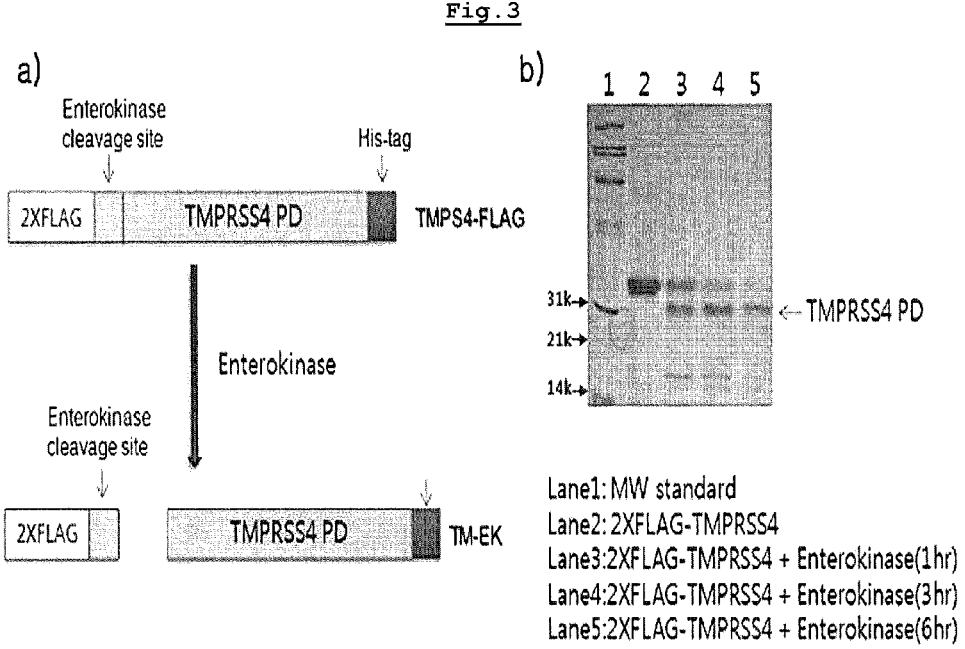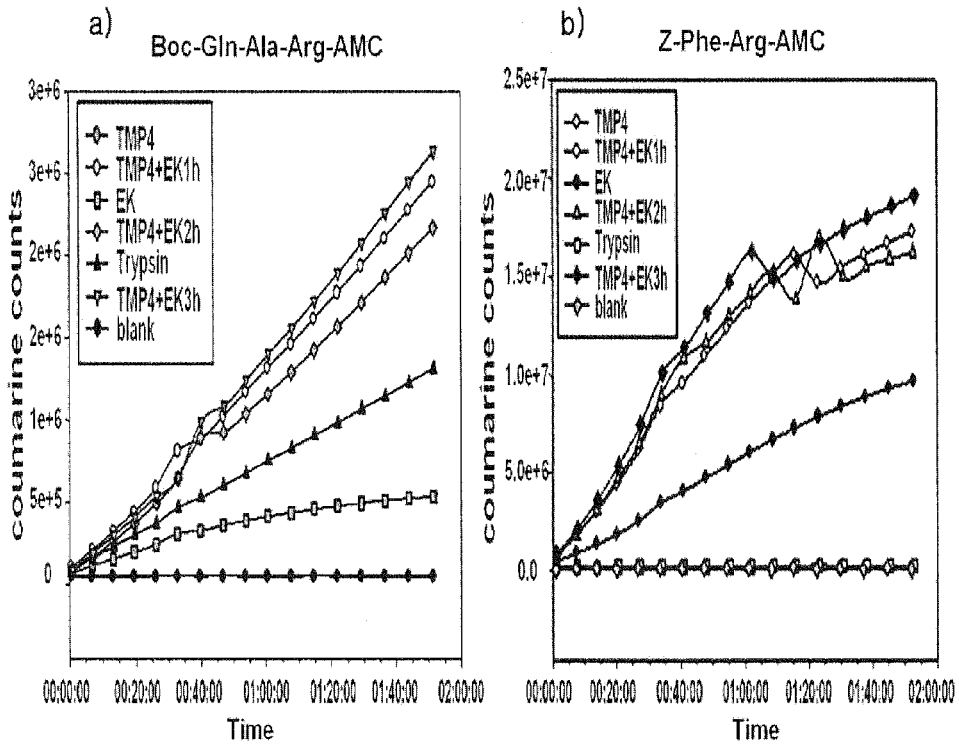

Lane1: MW standard
Lane 2: rabbit normal IgG
Land3: Ag-purified TMPRSS4-FLAG

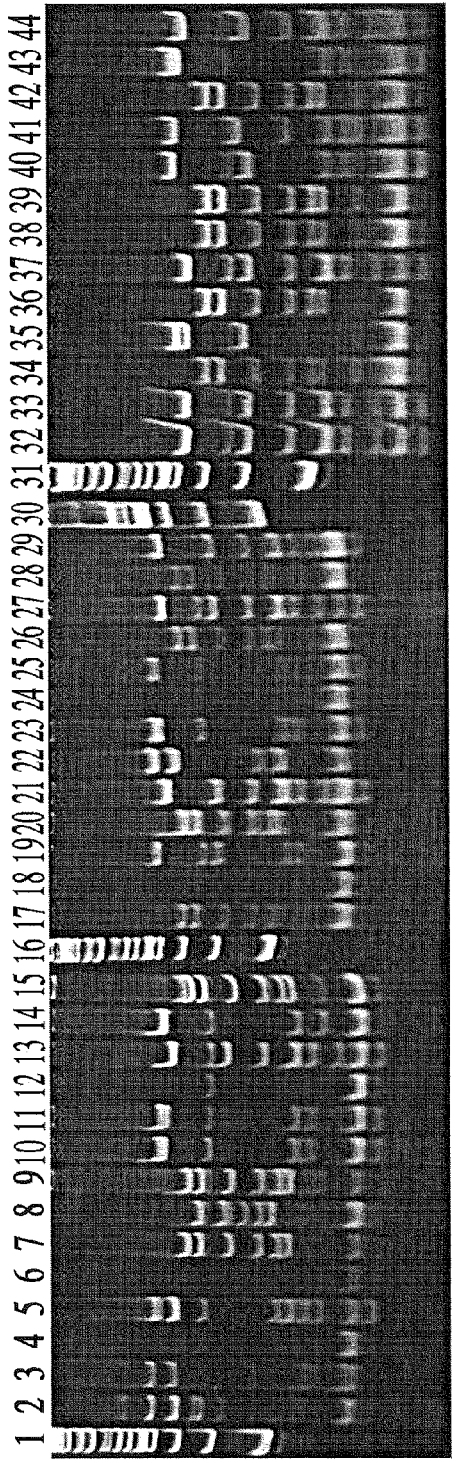

Fig.8a

Heavy Chain

```
              -------- FR 1 ----------       CDR1   ---- FR 2 -
              1                                              50
T1-11G  (1)  MA QVQLVQSGGGVVQPGRSLRLSCAASGFTLS- -RYTMH WVRQAPGKGLQ
T2- 6A  (1)  MA QMQLVQSGAEVKKPGASVKVSCKASGYTFT- -SYDVH WVRQATGQGLE
T1- 5G  (1)  MA QMQLGVSGGGLVKPGGSLRFSCAASGFSFS- -DHYMS WIRQAPGKGLE
T1-12C  (1)  MA QVQLVESGGGVVQPGRSLRLSCTASGFTFR- -NYGMH WVRQAPGKGLE
T2- 9G  (1)  MA QVQLVESGGGVVQPGRSLRLSCTASGFTFR- -NYGMH WVRQAPGKGLE
T1- 9F  (1)  MA QVQLVESGGGLVQPGGSLRLSCAASGFTFS- -SYAMS WVRQAPGKGLE
T2-12F  (1)  MA QVQLVESGGGLVQPGGSLRLSCAASGFTFS- -SYAMS WVRQAPGKGLE
T2- 8F  (1)  MA QVQLVESGGGLVQPGGSLRLSCAASGFTFR- -NYAMN WVRQAPGKGLE
T2-12A  (1)  MA QVQLVKSGGGLVQPGGSLRLSCAASGVNFN- -NYAMS WVRQAPGKGLE
T2-12C  (1)  MA QVQLVQSGGGVVQPGRSLRLSCAASGFTFN- -RYGIH WVRQAPGKGLE
T2- 3A  (1)  MA QMQLVQSGGGVVQPGRSLRLSCAASGFTFS- -SYAMH WVRQAPGKGLE
T2- 7B  (1)  MA QVQLQESGPGLVKPSQTLSLTCAISGDSVS RDSVAWN WIRQSPSRGLE
T2- 6G  (1)  MA QVQLVESGGGVVQPGRSLRLSCVGSGFTFS --NYGMH WVRQAPGKGLQ
T2-10E  (1)  MA QMQLVQSGGGVVKPGGSLRLSCGASGFTFD- -DYAMH WVRQAPGKGLE
T2- 6C  (1)  MA QMQLVESGGGLVQPGRSLRLSCAASGFTFD- -DYAIH WVRQAPGKGLE

---   ------ CDR 2 -----   ------------ FR 3 -----------
              51                                                   100
T1-11G (49)  WVA VISSDGSKK-YYGDSVKG RFTISRDNSKNTLYLQMNSLRAEDTAVYY
T2- 6A (49)  WMG WVNPSGNA-DYAQKFQG  RVTMTRNSSISTAYMELSSLRSEDTAVYY
T1- 5G (49)  WVS YISNRGYSI-YYADSVKD RFTISRDNAKNTLYLQMNSLRAEDTAVYY
T1-12C (49)  WVA VISYDGSTK-YYADSVRG RFTISRDNSKNTLYLQMNSLRSEDTAVYY
T2- 9G (49)  WVA VISYDGSTK-YYADSVRG RFTISRDNSKNTLYLQMNSLRSEDTAVYY
T1- 9F (49)  WVS AITGSGGST-FYADSVKG RFTISRDNSKNMLYLQMNSLRAEDTAVYY
T2-12F (49)  WVS AITGSGGST-FYADSVKG RFTISRDNSKNMLYLQMNSLRAEDTAVYY
T2- 8F (49)  WVS AISGSGGST-YYADSVKG RFTISRDNAKGTLYLQMNSLRAEDTAVYY
T2-12A (49)  WVS AISGSGAST-NYADSVKG RFTISRDNSENTLYLQMNSLRAEDTAVYY
T2-12C (49)  WVT VISYDGNIK-YYADSVKG RFTISRDNSKNTVYLQMNSLRSEDTAVYY
T2- 3A (49)  WIS SISWSSNNI-RYADSVKG RFTISRDNAKNSLYLQMNSLRSEDTAVYY
T2- 7B (51)  WLG RTYYKSKWYNDYAVSVRS RITINPDTSKNQFSLQLNSVTAVDTAVYY
T2- 6G (49)  WVA VISYDGSKK-YYADSVKG RFTISRDNSKNTLYLQMNSLRSEDTAVYY
T2-10E (49)  WVS GISWNSGSI-GYADSVKG RFTISRDNSKNSLYLQMNSLRAEDTAVYY
T2- 6C (49)  WVS GISWNSEIV-GYGDSVKG RFTISRDNAKNSLDLQMNSLRAEDTAVYY

---   ----- CDR 3 -----  --- FR 4---  ------ Linker ----
              101                                                  150
T1-11G  (98) CAR GGGK--------GHWLDT    WGQGSLVTVSSGLGGLGGGGSGGGGSGGS (서열번호 45)
T2- 6A  (98) CAV GR----------FGAFDV    WGQGSMVTVSSGLGGLGGGGSGGGGSGGS (서열번호 46)
T1- 5G  (98) CAK DLRSSDAHTWGGVDAFDI    WGLGTMVTVSSGLGGLGGGGSGGGGSGGS (서열번호 46)
T1-12C  (98) CAR G-----------SDVAY     WGQGTLVTVSSGLGGLGGGGSGGGGSGGS (서열번호 47)
T2- 9G  (98) CAR G-----------SDVAY     WGQGTLVTVSSGLGGLGGGGSGGGGSGGS (서열번호 47)
T1- 9F  (98) CAR G-----------GNLDV     WGLGTTVTVSSGLGGLGGGGSGGGGSGGS (서열번호 48)
T2-12F  (98) CAR G-----------GNLDV     WGLGTTVTVSSGLGGLGGGGSGGGGSGGS (서열번호 49)
T2- 8F  (98) CAR LR----------GAFDI     WGQGTMITVSSGLGGLGGGGSGGGGSGGS (서열번호 50)
T2-12A  (98) CAV LGRE---Q-YLARGYFEH    WGRGTLVTVSSGLGGLGGGGSGGGGSGGS (서열번호 51)
T2-12C  (98) CAR LW------RQSAADAFDI    WGPGTMITVSSGLGGLGGGGSGGGGSGGS (서열번호 52)
T2- 3A  (98) CAR ---------RAAAKAFDI    WGQGTRVTVSSGLGGLGGGGSGGGGSGGS (서열번호 53)
T2- 7B  (101) CSR GG----------GKGMDV   WGQGTSVTVSSGLGGLGGGGSGGGGSGGS (서열번호 54)
T2- 6G  (98) CAR G-----------TTMDV     WGKGTTVTVSSGLGGLGGGGSGGGGSGGS (서열번호 55)
T2-10E  (98) CAK GLRGLRYRNY--YYGMDV    WGQGTTVTVSSGLGGLGGGGSGGGGSGGS (서열번호 56)
T2- 6C  (98) CAR GSSG-R------AFDI      WGQGTMVTVSSGLGGLGGGGSGGGGSGGS (서열번호 57)
```

Fig.8b

```
Light Chain
                 ----- --------- FR 1 --------- ---- CDR 1 ----    -----
                151                                                     200
T1-11G   (140)  SGVGS DIQMTQSPSSVSASVGDRVTITC  RASQSISK-----WLA  WYQQKP
T2- 6A   (138)  SGVGS DIQMTQSPSSVSASVGDRVTITC  RASQGISR-----WLA  WYQQKP
T1- 5G   (148)  SGVGS DIQMTQSPSSLSASVGDRVTITC  RASQSISS-----WLA  WYQQKP
T1-12C   (136)  SGVGS DIVMTQTPLSLSVTPGQPASISC  RSSQSLVYSDGNTYLN  WFHQRP
T2- 9G   (136)  SGVGS DIVMTQTPLSLSVTPGQPASISC  RSSQSLVYSDGNTYLN  WFHQRP
T1- 9F   (136)  SGVGS DIVMTQTPLSSPVTLGQPASISC  RSSQSLVHSNGNTYLT  WLQQRP
T2-12F   (136)  SGVGS DIVMTQTPLSSPVTLGQPASISC  RSSQSLVHSNGNTYLT  WLQQRP
T2- 8F   (137)  SGVGS DIVMTQTPLSLPVTPGEPASISC  RSSQSLLHSNGYNYLD  WYLQKP
T2-12A   (144)  SGVGS SYELTQDP-AVSVALGQTVRITC  QGDSLRSY-----YAS  WYQQKP
T2-12C   (142)  SGVGS QFALTQPR-SVSGSPGQSVTISC  TGTSSDVGGS--SYVS  WYQQHP
T2- 3A   (139)  SGVGS QSALTQPA-SVSGSPGQSITISC  TGTSTDIGGY--NYVS  WYQQHP
T2- 7B   (141)  SGVGS QSALTQPR-SVSGSPGQSVTISC  TGTSGDIGGFN--YVS  WYQQHP
T2- 6G   (136)  SGVGS QSALTQPP-SASGTPGQRVTISC  SGSNSNIGSN---TVN  WYQQFP
T2-10E   (146)  SGVGS DIQMTQSSSSLSASIGDRVTITC  QASQDITN-----YLN  WYQQKP
T2- 6C   (139)  SGVGS DIQMTQSPSSVSASVGDRITITC  RASQSIST-----YLN  WYQQKP FR 2 ----   CDR2   ------------- FR 3 -------------   --
                201                                                    250
T1-11G   (185)  GKAPKLLIY  AASNLQS  GVPSRFNGSGSGTDFTLTINSLQPEDFATYYC  LQ
T2- 6A   (183)  GKAPKLLIY  AASNLQS  GVPSRFSGSGSGTDFTLTINSLQPDDFAIYYC  QQ
T1- 5G   (193)  GKAPKLLIY  KASSLES  GVPSRFSGSGSGTDFTLTINSLQPEDFATYYC  QQ
T1-12C   (186)  GQPPRRLIY  KVSNRDS  GVPGRFSGSGSGTDFTLRISRVEAEDVGVYYC  MQ
T2- 9G   (186)  GQPPRRLIY  KVSNRDS  GVPGRFSGSGSGTDFTLRISRVEAEDVGVYYC  MQ
T1- 9F   (186)  GQPPRLLIY  KISKRFS  GVPDRFSGSGAGTDFTLKISRVEAEDVGVYYC  MQ
T2-12F   (186)  GQPPRLLIY  KISKRFS  GVPDRFSGSGAGTDFTLKISRVEAEDVGVYYC  MQ
T2- 8F   (187)  GQSPQLLIY  LGSKRAA  GVPDRFSGSGSGTDFTLKISRVEAEDVGVYYC  MQ
T2-12A   (188)  GQAPVLVIY  GKNNRPS  GIPDRFSGSNSGNTASLTITGTQAEDEAVYYC  SS
T2-12C   (189)  GKAPKLMIY  DVTRRPS  GVPDRFSGSKSDNTASLTISGLQPKDEADYYC  AS
T2- 3A   (186)  GKAPKLMIS  DVNNRPS  GVSHRFSGSKSGNTASLTISGLQSEDEADYYC  SS
T2- 7B   (188)  GRAPKIIIY  DVSRRPS  GVPNRFSASKSGNTASLTVSGLQPEDEATYFC  AS
T2- 6G   (182)  GKAPQLLIF  GHNQRPS  GVPDRFSGSKSGTSASLSISGLQSEDEAHYYC  AS
T2-10E   (191)  GKAPKLLIY  AASSLHT  GVPSRFSGSGSGTDFTLTITNMLPEDFATYYC  QQ
T2- 6C   (184)  GKAPKLLIY  GATSLQS  GVPSRFSGSGSGTDFTLTIRGLQPDDFGTYYC  QQ

- CDR 3---    -- FR 4 --    ---- Myc Tag ----
                251                        291
T1-11G   (235)  SNS----LPIT  FGQGTRLDIKR  GGASLVEFEQKLISEEDL-  (서열번호 97)
T2- 6A   (233)  ANS----FPLT  FGPGTKVDIKR  GGASLVEFEQKLISEEDL-  (서열번호 98)
T1- 5G   (243)  FNN----NLFS  FGPGTKVNIKR  GGASLVEFEQKLISEEDL-  (서열번호 98)
T1-12C   (236)  SLR----TPLT  FGGGTKVDIKR  GGASLVEFEQKLISEEDL-  (서열번호 99)
T2- 9G   (236)  SLR----TPLT  FGGGTKVDIKR  GGASLVEFEQKLISEEDL   (서열번호 99)
T1- 9F   (236)  LTQ----FPLT  FGGGTKVEIKR  GGASLVEFEQKLISEEDL-  (서열번호 100)
T2-12F   (236)  LTQ----FPLT  FGGGTKVEIKR  GGASLVEFEQKLISEEDL-  (서열번호 101)
T2- 8F   (237)  ALQ----TP-T  FGQGTKVDIKR  GGASLVEFEQKLISEEDL-  (서열번호 102)
T2-12A   (238)  RDSSG--NHLV  FGGGTKLTVLG  GGASLVEFEQKLISEEDL-  (서열번호 103)
T2-12C   (239)  YAG----SHYL  FGTGTKVTVLG  GGASLVEFEQKLISEEDL-  (서열번호 104)
T2- 3A   (236)  YTS----SSFV  FGTGTKVTVLG  GGASLVEFEQKLISEEDL-  (서열번호 105)
T2- 7B   (238)  YAG---TKFWL  FGGGTKLTVLG  GGASLVEFEQKLISEEDL-  (서열번호 106)
T2- 6G   (232)  WDDTVSGPKWV  FGGGTKLTVLG  GGASLVEFEQKLISEEDL-  (서열번호 107)
T2-10E   (241)  SHS----PPFT  FGGGTKVDIKR  GGASLVEFEQKLISEEDL-  (서열번호 108)
T2- 6C   (234)  SYN----LPRT  FGQGTKLDIKR  GGASLVEFEQKLISEEDL-  (서열번호 109)
```

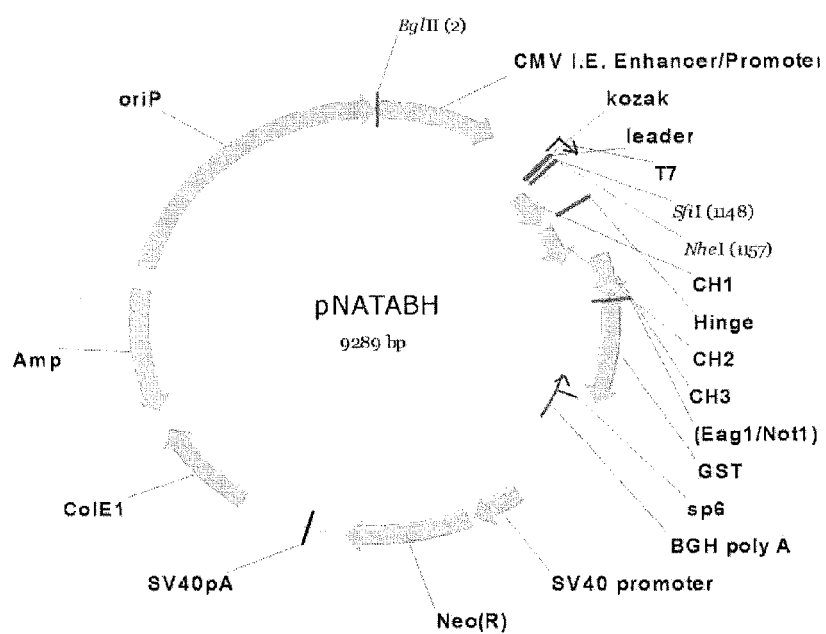
H chain vector
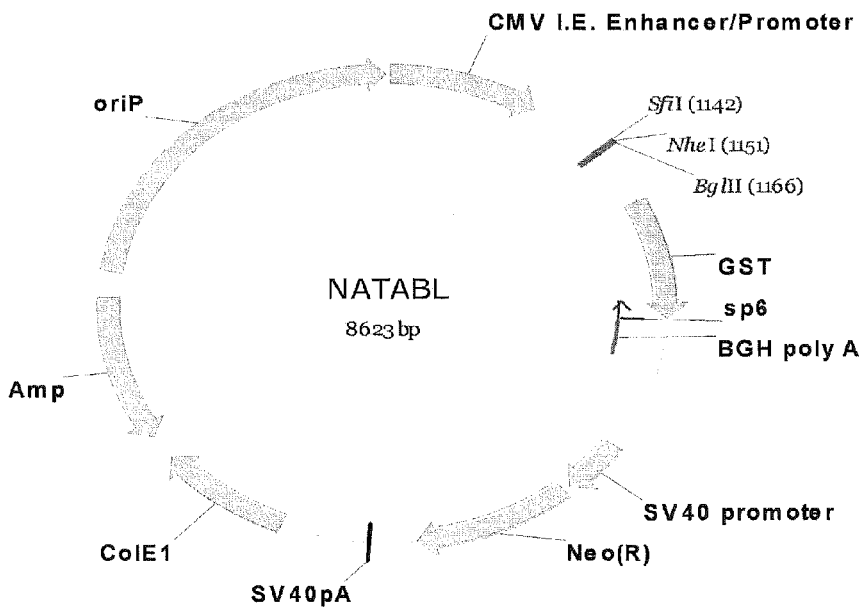
L chain vector

Fig.12
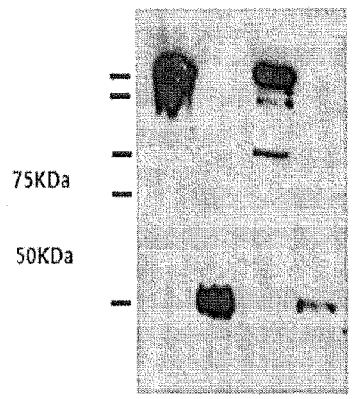
1. huIgG-non reducing (10 ng)
2. huIgG-reducing (10 ng)
3. T2-6C-non reducing
4. T2-6C-reducing
1st Ab: anti-hu FC-HRP (1:2000) 상온 1h
Expose time: 1 min
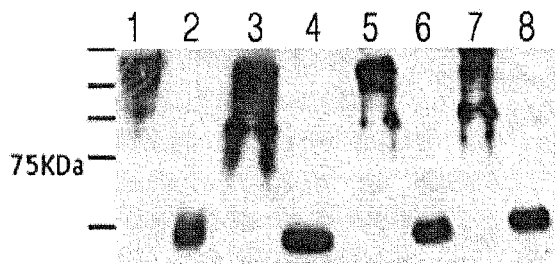
1. Non reduced Hu IgG (20 ng)
2. Reduced Hu IgG (20 ng)
3. Non reduced T2-6G
4. Reduced     T2-6G
5. Non reduced T2-3A
6. Reduced     T2-3A
7. Non reduced T2-8F
8. Reduced     T2-8F
Fig.13
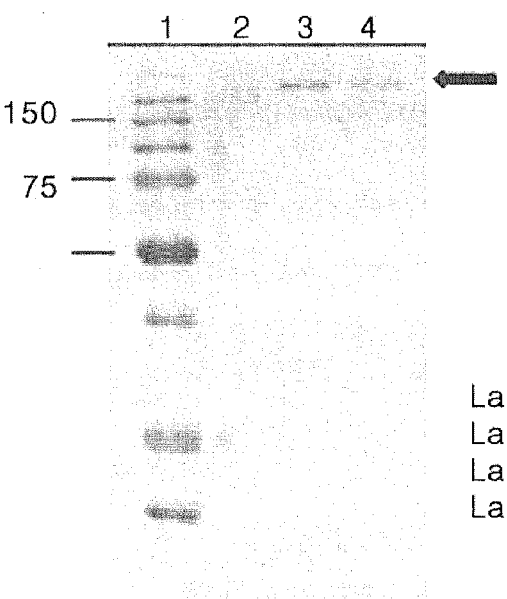
Lane 1: MW marker
Lane 2: normal human IgG
Land 3: T2-6C
Lane 4: T2-6G 1st Ab: anti-TMPRSS4 polyserum(0.5 μg/sample) / rabbit IgG(0.5 μg/sample)
2nd Ab: anti-rabbit FITC(1:200)

1st Ab: T2-6C(1 μg) or T2-6G(0.5 μg) / nor human IgG(1 μg or 0.5 μg, respectively)
2nd Ab: anti-human Fc-FITC(1:200)

Fig.16
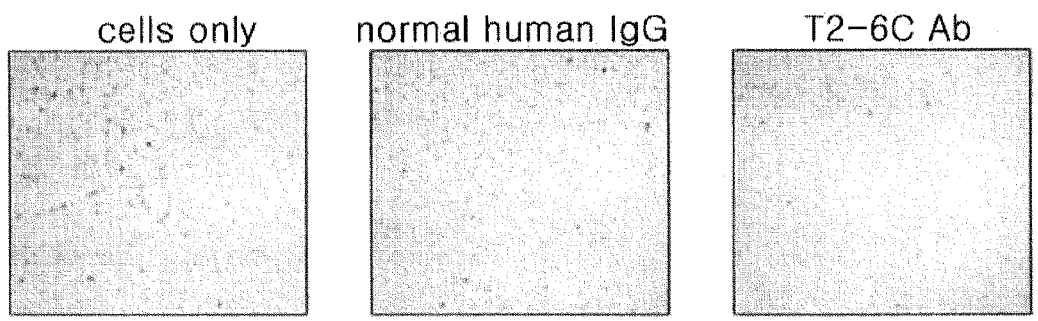
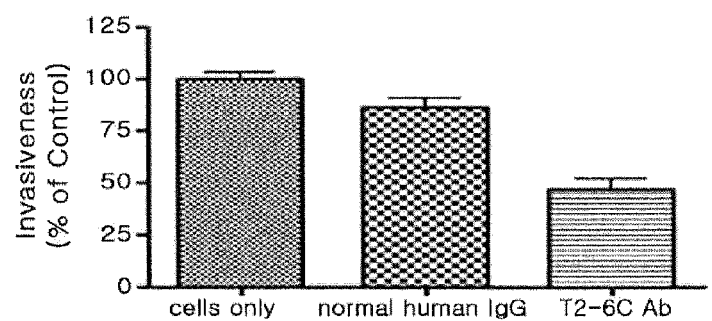
Fig.17
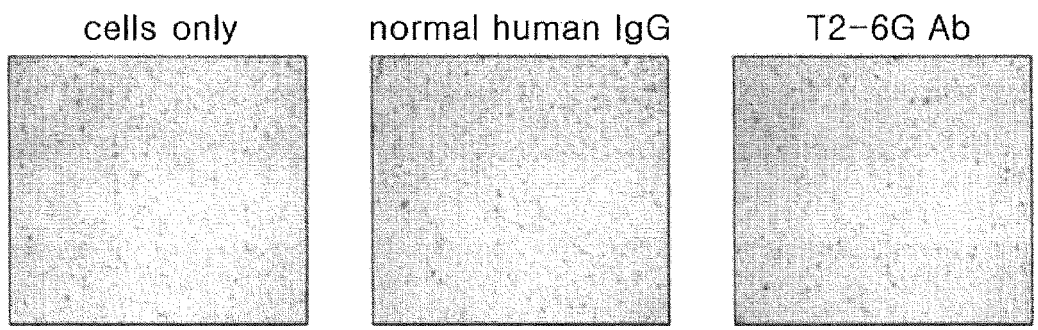
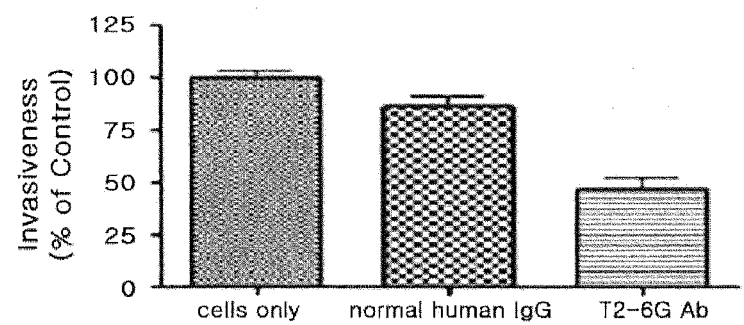

Fig.18
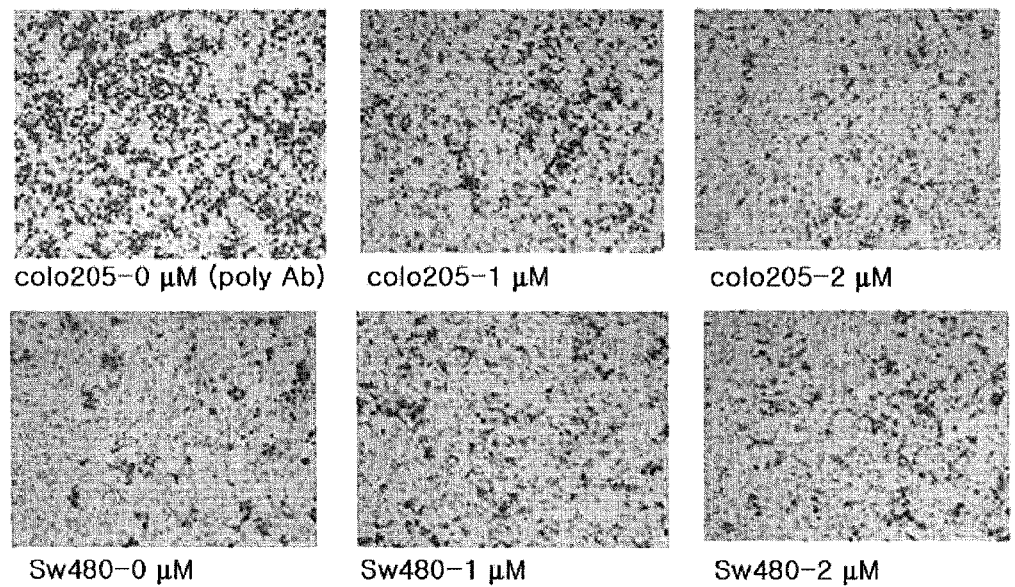
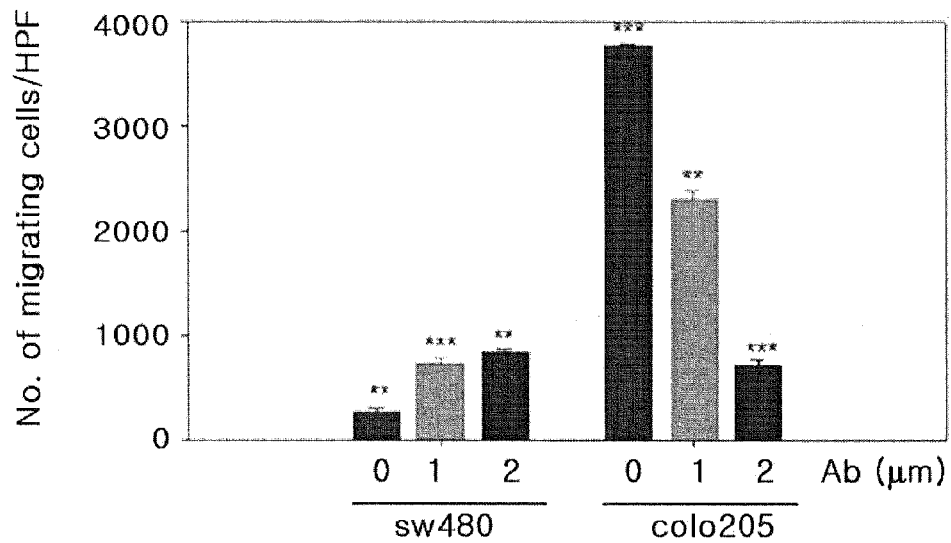

Fig.19
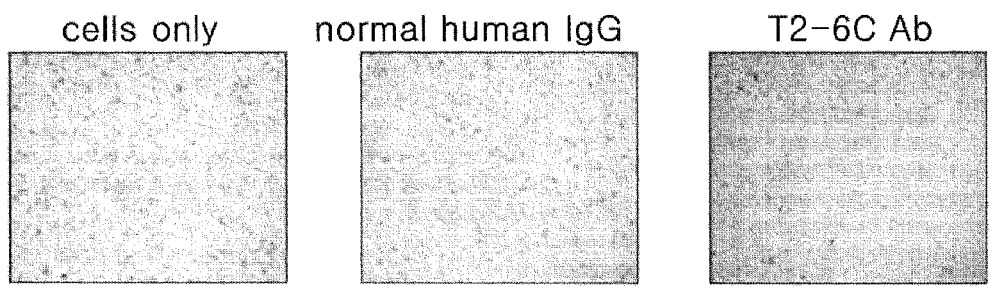
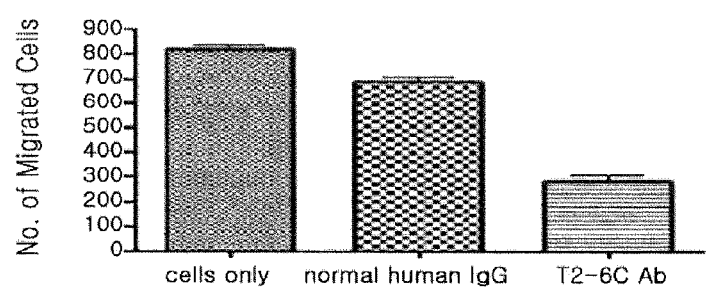
Fig.20
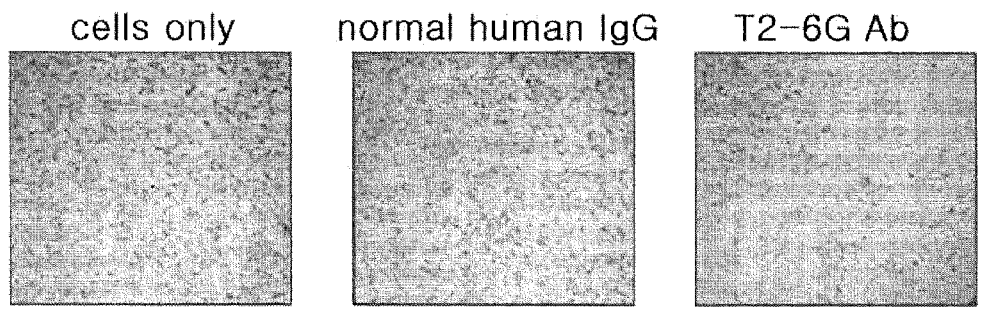
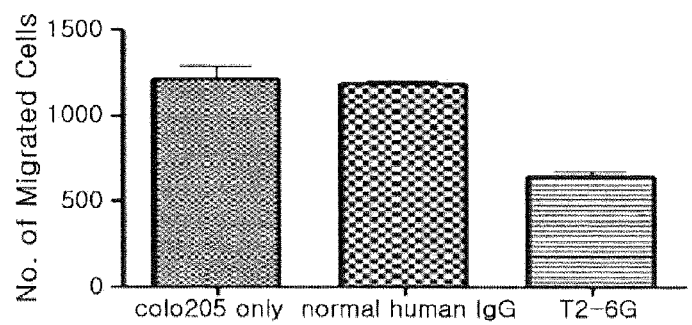

TMPRSS4-SPECIFIC HUMAN ANTIBODY

CROSS REFERENCE TO RELATED APPLICATIONS

This application is a national stage application under 35 U.S.C. 371 of PCT Application No. PCT/KR2008/006614 having an international filing date of 10 Nov. 2008, which designated the United States, which PCT application claimed the benefit of South Korea Application No. 10-2008-0101575 filed 16 Oct. 2008, the entire disclosure of each of which are hereby incorporated herein by reference.

REFERENCE TO A SEQUENCE LISTING

This application contains a Sequence Listing submitted electronically as a PDF file. The PDF file, named "WO_2010_044506_SEQUENCE_LISTING.pdf," has a size in bytes of 586 KB, and was filed on 10 Nov. 2008 under International Application No. PCT/KR2008/006614. The information contained in the text file is incorporated herein by reference in its entirety pursuant to 37 CFR §1.52(e)(5).

BACKGROUND OF THE INVENTION

The present disclosure relates to a transmembrane protease, serine 4 (TMPRSS4)-specific human antibody.

It has been confirmed that transmembrane protease, serine 4 (TMPRSS4) is significantly upregulated and expressed in lung cancer, liver cancer, colorectal cancer, pancreatic cancer, and gastric cancer and is overexpressed in most pancreatic cancer cell lines, and it has been proposed that due to its overexpression in malignant thyroid neoplasms, the gene be used as a marker for diagnosis and prognostic evaluation of these types of tumors (Kebebew E et al., Ann Surg 242(3): 353-361, 2005; Kebebew E et al., Cancer 106 (12):2592-2597, 2006).

What biological functions TMPRSS4 performs in cancer have been revealed (Jung H et al. Oncogene 17; 27 (18): 2635-2647, 2007). This study suggests that TMPRSS4 is an important mediator for invasion, metastasis, migration, and adhesion of human cancer cells and epithelial mesenchymal transition (EMT) in human epithelial cancer cells, and is a new potential target for cancer. Although much research has not been conducted on TMPRSS4, there is also a need for development of antibodies against TMPRSS4 as a target for cancer due to its potentialities as a strong and independent prognostic marker and as a target for inhibition of tumor invasion and metastasis.

Thus, the present inventors have selected 13 kinds of human antibodies specifically bound to TMPRSS4 expressing on the surface of a colorectal cancer cell line, confirmed that the human antibody has binding capacity similar to those of the conventional nonhuman-derived antibodies, and have made the present invention.

TECHNICAL PROBLEM

One object of the present invention is to provide a TMPRSS4-specific human antibody.

Another object of the present invention is to provide a polynucleotide encoding a heavy chain of the human antibody or a fragment thereof, and an expression vector including the polynucleotide and a constant region of human heavy chain.

Still another object of the present invention is to provide a polynucleotide encoding a light chain of the human antibody or a fragment thereof, and an expression vector including the polynucleotide and a constant region of human light chain.

Even another object of the present invention is to provide a transformant prepared by introducing an expression vector including a polynucleotide encoding the heavy chain of the human antibody or an immunologically active fragment thereof into a host cell.

Yet another object of the present invention is to provide a transformant prepared by introducing an expression vector including a polynucleotide encoding the light chain of the human antibody or an immunologically active fragment thereof into a host cell.

Further another object of the present invention is to provide a transformant prepared by introducing an expression vector including a polynucleotide encoding the heavy chain of the human antibody or a fragment thereof and an expression vector including a polynucleotide encoding the light chain or a fragment thereof simultaneously into a host cell.

Still further another object of the present invention is to provide a method for preparing a TMPRSS4-specific human antibody by incubating the transformant. The present invention also provides a composition including the human antibody.

The present invention also provides a pharmaceutical composition including the human antibody.

Another object of the present invention is to provide a method for treating a TMPRSS4-overexpressed cancer, the method including administering a pharmaceutically effective amount of the human antibody to a subject with the TMPRSS4-overexpressed cancer.

Still another object of the present invention is to provide a composition including the human antibody, light or heavy chain of the human antibody or an immunologically active fragment thereof, and a radioactive isotope.

Even another object of the present invention is to provide an immunodetection method for detecting an ex vivo TMPRSS4-overexpressed cancer, including contacting a composition for detection of the cancer with a cancer cell.

Yet another object of the present invention is to provide a method for imaging an in vivo TMPRSS4-overexpressed cancer, including administering a diagnostically effective amount of the composition for detection of the cancer to a subject.

Further another object of the present invention is to provide a method for prognostic evaluation of a cancer treatment using a composition for detection.

SUMMARY OF THE INVENTION

To achieve the objects, the present invention provides a TMPRSS4-specific human antibody including a heavy chain including a heavy chain variable region ($V_H$) including a heavy chain complementarity determining region (hereinafter, HCDR) 1 having an amino acid sequence selected from the group consisting of SEQ ID Nos. 7 to 18, HCDR 2 having an amino acid sequence selected from the group consisting of SEQ ID Nos. 19 to 31, and HCDR 3 having an amino acid sequence selected from the group consisting of SEQ ID Nos. 32 to 44, or a fragment thereof; and a light chain including a light chain variable region ($V_L$) including a light chain complementarity determining region (hereinafter, LCDR) 1 having an amino acid sequence selected from the group consisting of SEQ ID Nos. 58 to 70, LCDR 2 having an amino acid sequence selected from the group consisting of SEQ ID Nos. 71 to 83, and LCDR 3 having an amino acid sequence selected from the group consisting of SEQ ID Nos. 84 to 96, or a fragment thereof.

The present invention also provides a polynucleotide encoding a heavy chain of the human antibody or an immunologically active fragment thereof, and an expression vector including the polynucleotide.

The present invention also provides a polynucleotide encoding a light chain of the human antibody or an immunologically active fragment thereof, and an expression vector including the polynucleotide.

The present invention also provides a transformant prepared by introducing an expression vector including a polynucleotide encoding a heavy chain of the human antibody or an immunologically active fragment thereof into a host cell. The present invention also provides a transformant prepared by introducing an expression vector including a polynucleotide encoding a light chain of the human antibody or an immunologically active fragment thereof into a host cell.

The present invention also provides a transformant prepared by introducing an expression vector including a polynucleotide encoding a heavy chain of the human antibody or an immunologically active fragment thereof and an expression vector including a polynucleotide encoding a light chain of the human antibody or an immunologically active fragment thereof simultaneously into a host cell.

The present invention also provides a method for preparing a TMPRSS4-specific human antibody by incubating the transformant.

The present invention also provides a composition including the human antibody.

The present invention also provides a pharmaceutical composition including the human antibody.

The present invention also provides a method for treating a TMPRSS4-overexpressed cancer, including administering a pharmaceutically effective amount of the human antibody to a subject with the cancer.

The present invention also provides a composition including the human antibody, a light or heavy chain of the human antibody or an immnunologically active fragment thereof, and a radioactive isotope.

The present invention also provides an immunodetection method for detecting an ex vivo TMPRSS4-overexpressed cancer, including contacting a composition for detection of the cancer with a cancer cell. The present invention also provides a method for imaging an in vivo TMPRSS4-overexpressed cancer, the method including:
1) administering a diagnostically effective amount of a composition for detection of the cancer to a subject; and
2) obtaining a detection image for the subject. The present invention also provides a method for treating an in vivo TMPRSS4-overexpressed cancer, the method including:
1) intravenously administering a composition including the radioactive isotope to a subject;
2) detecting the composition of Step 1) to identify tumor cells; and
3) eliminating the tumor cells identified in Step 2) by surgical operation.

The present invention also provides a method for prognostic evaluation of a cancer patient, the method including:
1) intravenously administering a composition including the radioactive isotope to a patient whose tumor has been eliminated;
2) detecting the composition of Step 1) to identify tumor cells; and
3) judging that all tumor cells have been eliminated when tumor cells are not detected in step 2).

ADVANTAGEOUS EFFECT

The TMPRSS4-specific human antibody expressed in colorectal cancer cells of the present invention may be used in diagnosis of the TMPRSS4-overexpression cancers, classification of the diseases, visualization, treatment, and prognostic evaluation.

BRIEF DESCRIPTION OF THE DRAWINGS

The above and other objects, features and other advantages of the present invention will be more clearly understood from the following detailed description taken in conjunction with the accompanying drawings, in which:

FIG. 3 is a group of drawings illustrating results of a purified TM-EK with FLAG removed, identified by SDS-PAGE: a: a schematic diagram of TM-EK construction; and b: a photo of a purified TM-EK, identified by SDS-PAGE.

FIG. 4 is a group of graphs illustrating results of measurement of proteolytic activities of TMPRSS4.

FIG. 7 is a photo illustrating results of diversity of monoclonal phage antibodies against TMPRSS4, identified by fingerprinting.

FIG. 8 is a list of sequences illustrating analysis results of polypeptides used in heavy chain and light chain CDRs of monoclonal phage antibodies against TMPRSS4: a: heavy chain; and b: light chain.

FIG. 11 is a group of cleavage maps of pNATAB H vector and pNATAB L vector: a: pNATAB H vector; and b: pNATAB L vector.

FIG. 12 is a group of photos illustrating results of expressed and purified whole form IgGs, identified by Western blot a: monoclonal antibody T2-6C; and b: monoclonal antibodies T2-6G, T2-3A, and T2-8F.

FIG. 13 is a photo illustrating of purified monoclonal antibodies T2-6C and T2-6G, identified by SDS-PAGE.

FIG. 16 is a group of photos and a graph illustrating results, confirming that monoclonal antibody T2-6C inhibits the invasion of colorectal cancer cell line Colo205.

FIG. 17 is a group of photos and a graph illustrating results, confirming that monoclonal antibody T2-6G inhibits the invasion of colorectal cancer cell line Colo205.

FIG. 18 is a group of photos and a graph illustrating results, confirming that TMPRSS4 polyclonal antibody had effects on the migration of TMPRSS4-overexpressed cell line Colo205 and TMPRSS4-underexpressed cell line Sw480.

FIG. 19 is a group of photos and a graph illustrating results, confirming that monoclonal antibody T2-6C inhibits the migration of TMPRSS4-overexpressed cell line Colo205.

FIG. 20 is a group of photos and a graph illustrating results, confirming that monoclonal antibody T2-6G inhibits the migration of TMPRSS4-overexpressed cell line Colo205.

DETAILED DESCRIPTION OF EXEMPLARY EMBODIMENTS

Figure 1:
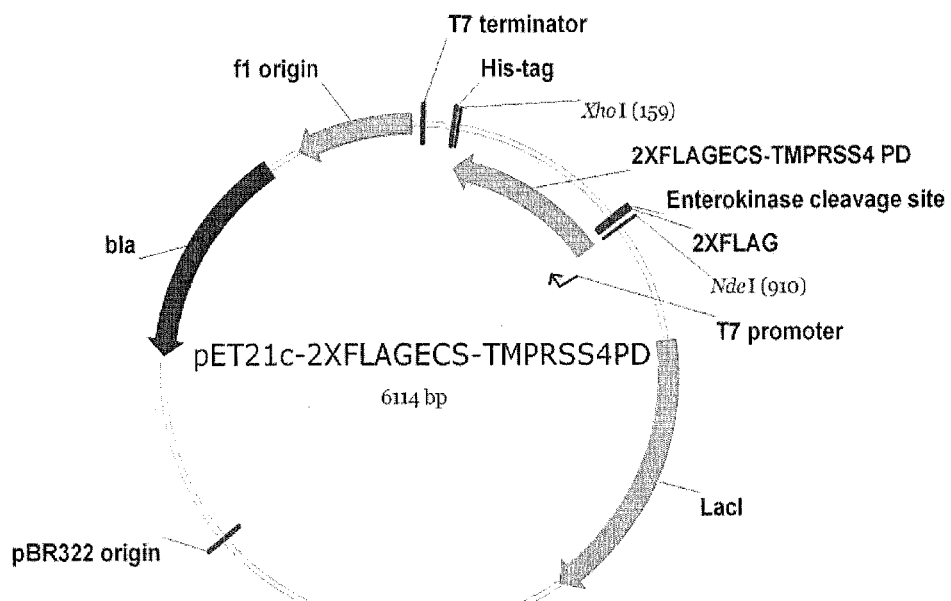
FIG. 1 is a cleavage map of TMPRSS4-FLAG expression vector.

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the terms of the present invention will be described.

"Variable region" means a region of an antibody molecule which specifically binds to an antigen and demonstrates modifications in sequence, which is exemplified by CDR1, CDR2, and CDR3. Between the CDRs, there is a framework region (FR) which supports the CDR loop.

"Complementarity determining region" is a loop-shaped site involved in antigen recognition, and specificity of an antibody against antigen depends on modification in that site. "Panning" refers to a process of selecting only a phage expressing a peptide which binds to a target molecule (antibody, enzyme, cell-surface receptor, etc.) on the coat of the phage from a phage library displaying the peptide on the coat.

Hereinafter, the present invention will be described in detail.

The present invention provides TMPRSS4-specific human antibody including: a heavy chain including a heavy chain variable region ($V_H$) including a heavy chain complementarity determining region (hereinafter, HCDR) 1 having an amino acid sequence selected from the group consisting of SEQ ID Nos. 7 to 18, HCDR 2 having an amino acid sequence selected from the group consisting of SEQ ID Nos. 19 to 31, and HCDR 3 having an amino acid sequence selected from the group consisting of SEQ ID Nos. 32 to 44, or a fragment thereof; and a light chain including a light chain variable region ($V_L$) including a light chain complementarity determining region (hereinafter, LCDR) 1 having an amino acid sequence selected from the group consisting of SEQ ID Nos. 58 to 70, LCDR 2 having an amino acid sequence selected from the group consisting of SEQ ID Nos. 71 to 83, and LCDR 3 having an amino acid sequence selected from the group consisting of SEQ ID Nos. 84 to 96, or a fragment thereof.

Preferably, the heavy chain variable region has an amino acid sequence selected from the group consisting of SEQ ID Nos. 45 to 57, and the light chain variable region has an amino acid sequence selected from the group consisting of SEQ ID Nos. 97 to 109.

The antibody includes not only a whole antibody, but also a functional fragment of the antibody molecule. The whole antibody has a structure with two full-length light chains and two full-length heavy chains, and each light chain is linked to heavy chain by disulfide bond. The functional fragment of an antibody molecule indicates a fragment retaining a antigen-binding function, and examples of the antibody fragment include (i) Fab fragment consisting of light chain variable region ($V_L$), heavy chain variable region ($V_H$), light chain constant region ($C_L$), and heavy chain $1^{st}$ constant region ($C_{H1}$); (ii) Fd fragment consisting of $V_H$ and $C_{H1}$ domains; (iii) Fv fragment consisting of $V_L$ and $V_H$ domains of a monoclonal antibody; (iv) dAb fragment consisting of $V_H$ domain (Ward E S et al., Nature 341:544-546 (1989)); (v) separated CDR region; (vi) F(ab')2 fragment including two linked Fab fragments, as a divalent fragment; (vii) single chain Fv molecule (scFv) in which $V_H$ and $V_L$ domains are linked by a peptide linker to form an antigen binding site; (viii) bi-specific single chain Fv dimmer (PCT/US92/09965), and (ix) multivalent or multi-specific diabody fragment (WO94/13804) prepared by gene fusion. In the present invention, a human antibody against TMPRSS4 was obtained as scFV by using phage display technology and screened as a mono phage clone. As a result, 13 kinds of TMPRSS4-specific monoclonal phages were obtained.

In a specific example of the present invention, the activity (see FIGS. 3 and 4) of TMPRSS4 (see FIGS. 1 and 2) obtained through recombinant technology was identified and used in preparation of monoclonal antibodies (see FIG. 5) and monoclonal antibodies. The TMPRSS4 was reacted with a library phage constructed from human naive scFV library cells having diversity, followed by panning and screening of monoclones strongly binding to the TMPRSS4 antigen (see Tables 2 & 3 and FIG. 6). The selected monoclones were identified by fingerprinting (see FIG. 7), followed by sequencing to identify CDR regions of $V_H$ and $V_L$ of the antibody (see Table 6 and FIG. 8). The Ig BLAST program of NCBI (//www.ncbi.nlm.nih.gov/igblast/) was used for identification of similarity between the antibody and a germ line antibody group (see Table 7). As a result, 13 kinds of TMPRSS4-specific phage antibodies were obtained. The selected monoclonal antibodies had lower signal intensities than polyclonal antibodies. However, about 30 kDa of antigen proteins were detected clearly without any non-specific binding (see FIG. 9), and TMPRSS4 was specifically recognized and bound in a TMPRSS4-overexpressed colorectal cell line (see FIG. 10).

The present invention also provides a polynucleotide encoding a heavy chain of the human antibody or an immunologically active fragment thereof, and an expression vector including the polynucleotide.

The present invention also provides a polynucleotide encoding a light chain of the human antibody or an immunologically active fragment thereof, and an expression vector including the polynucleotide.

Figure 6A:
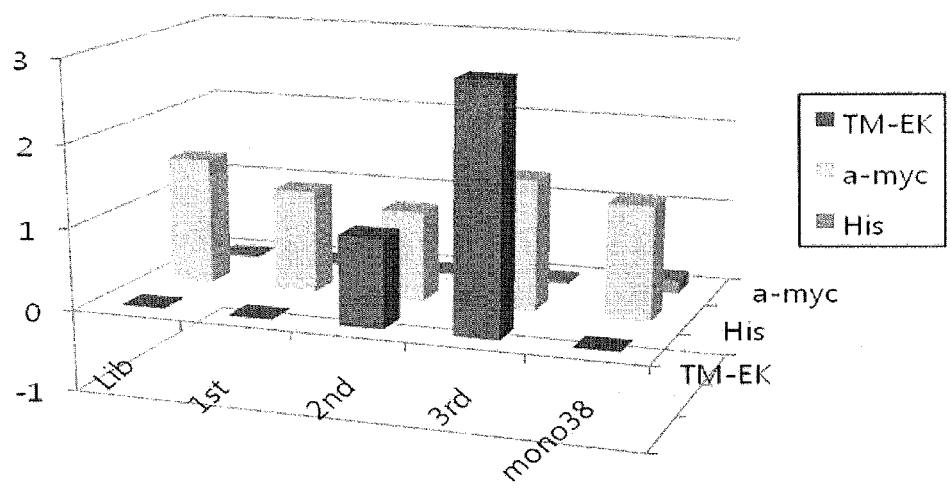
FIG. 6 is a group of graphs illustrating results of screening of phage antibodies in the 1st-3rd pannings, identified by SOS-PAGE: a: TMPS4-EK; and b: TMPS4-FLAG.
Figure 6B:
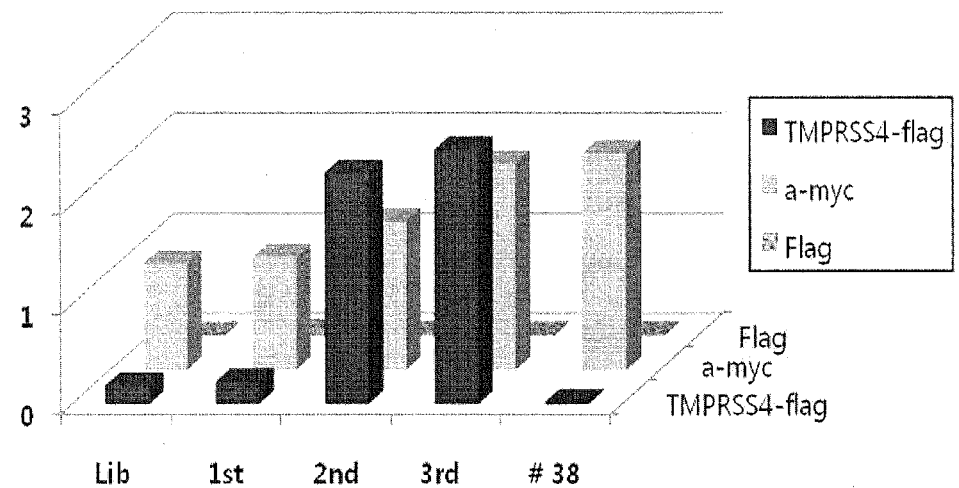

In a specific embodiment of the present invention, TMPRSS4 obtained by recombinant technology was used to screen monoclones strongly binding to TMPRSS4 antigens (see Tables 2 & 3 and FIG. 6). The selected monoclones were identified by fingerprinting (see FIG. 7), followed by sequencing to identify CDR regions of $V_H$ and $V_L$ of the antibody (see Table 6 and FIG. 8). The identification of similarity between the antibody and a germ line antibody group was performed (see FIG. 7). As a result, 13 kinds of TMPRSS4-specific phage antibodies were obtained. In the selected monoclonal antibodies, about 30 kDa of antigen proteins were detected clearly without any non-specific binding (see FIG. 9), and TMPRSS4 was specifically recognized and bound in a TMPRSS4-overexpressed colorectal cell line (see FIG. 10).

In the polynucleotide encoding a light and heavy chain of the human antibody of the present invention or a fragment thereof, due to degeneracy of the codon or in consideration of a preferred codon in an organism where light and heavy chains of the human antibody or a fragment thereof are to be expressed, various modifications may be made in a coding region within a scope that the amino acid sequences of light and heavy chains or a fragment thereof are not changed, and various changes or modifications may be made even in portions other than the coding region within a scope that the gene expression is not affected. It will be appreciated by those skilled in the art that these modified genes are also included within the scope of the present invention. That is, one or more nucleotides may be modified by substitution, deletion, insertion, or a combination thereof as long as the polynucleotide of the present invention encodes a protein with an equivalent activity thereof, and they are also included in the present invention. The sequence of the polynucleotide may be a single or double chain, and a DNA or RNA (mRNA) molecule.

In preparation of the expression vector, an expression control sequence such as a promoter, a terminator, an enhancer, etc., a sequence for membrane targeting or secretion, etc. may be appropriately selected according to a kind of host cell in which light and heavy chains of the human antibody or a fragment thereof are to be produced, and may be variously combined according to its purpose.

The expression vector of the present invention includes, but is not limited to, a plasmid vector, a cosmid vector, a bacteriophage, and a viral vector. A suitable expression vector may include expression regulatory elements such as a promoter, an operator, an initiation codon, a stop codon, a polyadenylation signal, and an enhancer and a signal sequence or leader sequence for membrane targeting or secretion, and may be variously prepared according to its purpose. A promoter of the expression vector may be constitutive or inductive. Examples of the signal sequence for use may include, but is not limited to, a PhoA signal sequence and an QmpA signal sequence for genus *Escherichia* hosts; an α-amylase signal sequence and a subtilicin signal sequence for genus *Bacillus* hosts; an MFa signal sequence and an SUC2 signal sequence for yeast hosts; and an insulin signal sequence, an α-interferon signal sequence, and an antibody molecule signal sequence for animal cell hosts. In addition, the expression vector may include a selection marker for selecting host cells containing the vector, and a replication origin when it is a replicable expression vector.

The present invention also provides a transformant prepared by introducing an expression vector including a polynucleotide encoding a heavy chain of the human antibody or an immunologically active fragment thereof into a host cell.

The present invention also provides a transformant prepared by introducing an expression vector including a polynucleotide encoding a light chain of the human antibody or an immunologically active fragment thereof into a host cell.

The present invention also provides a transformant prepared by introducing an expression vector including a polynucleotide encoding a heavy chain of the human antibody or a fragment thereof and an expression vector including a polynucleotide encoding a light chain of the human antibody or a fragment thereof simultaneously into a host cell.

In a specific example of the present invention, genes encoding light and heavy chains of a monoclonal phage were obtained and linked to a vector, respectively, and then a whole human IgG antibody expressed by introducing the expression vectors simultaneously into a host cell was identified (see FIG. 12). The human antibody in the form of whole IgG was purified (see FIG. 13), and then the binding capacity to TMPRSS4 was identified by FACS (see FIG. 14).

The expression vector according to the present invention may be transformed into a suitable host cell, for example, *E. coli* or yeast cell, and the transformed host cell may be incubated to produce light and heavy chains of the human antibody of the present invention or a fragment thereof in mass quantities. Incubation methods and media conditions suitable for a kind of host cell may be easily chosen from those known to those skilled in the art. The host cell may be a prokaryote such as *E. coli* or *Bacillus subtilis*. In addition, it may be a eukaryotic cell derived from yeast such as *Saccharomyces cerevisiae*, an insect cell, a vegetable cell, and an animal cell. More preferably, the animal cell may be an autologous or allogeneic animal cell. A transformant prepared through introduction into an autologous or allogeneic animal cell may be administered to a subject for use in cellular therapy for cancer. As for a method for introducing an expression vector into the host cell, it is possible to use any method if it is known to those skilled in the art.

The present invention also provides a method for preparing a TMPRSS4-specific human antibody by incubating the transformant.

Specifically, the present invention provides a method for preparing a TMPRSS4-specific human antibody, the method including:
1) incubating the transformant; and
2) purifying the human antibody from the medium.

As for the culture medium, it is desirable to select and use a culture medium suitable for the transformant among those known to those skilled in the art. As for the method for purifying human antibodies, it is possible to use any method known to those skilled in the art.

In a specific example of the present invention, genes encoding light and heavy chains of a monoclonal phage were obtained and linked to a vector, respectively, and then a whole human IgG antibody expressed by introducing the expression vectors simultaneously into a host cell was identified (see FIG. 12). The human antibody in the form of whole IgG was purified by protein A-affinity chromatography (see FIG. 13), and then the binding capacity to TMPRSS4 was identified by FACS (see FIG. 14).

The present invention also provides a composition including the human antibody.

The present invention also provides a pharmaceutical composition including the human antibody.

The pharmaceutical composition may be useful for prevention or treatment of a TMPRSS4-overexpressed cancer. The TMPRSS4-overexpressed cancer is preferably one selected from the group consisting of, but not limited to, colorectal cancer, lung cancer, liver cancer, pancreatic cancer, gastric cancer, and malignant thyroid neoplasms, and includes all the TMPRSS4-overexpressed cancers.

In a specific example of the present invention, it was confirmed that TMPRSS4 monoclonal antibodies inhibited an invasion in colorectal cancer cell line more significantly by 50% or more than rabbit and human normal IgGs (see FIGS. 15, 16, and 17), and migration of colorectal cancer cell line caused by TMPRSS4 was inhibited by TMPRSS4-specific polyclonal and monoclonal antibodies (see FIGS. 18 and 19). Furthermore, it was confirmed that the monoclonal antibody of the present invention caused the proliferation of TMPRSS4-overexpressed colorectal cancer cell line to be inhibited. Thus, the monoclonal antibody of the present invention may be used for prevention and treatment of TMPRSS4-overexpressed cancers.

The pharmaceutical composition of the present invention may selectively contain the TMPRSS4-specific human antibody or the transformant, and may additionally contain one or more effective ingredients exhibiting functions identical or similar to those of the ingredient. For administration, the pharmaceutical composition of the present invention may be formulated by including one or more pharmaceutically acceptable carriers in addition to the effective ingredients described above. For example, the pharmaceutically acceptable carrier includes saline solution, sterilized water, Ringer's solution, buffered saline solution, dextrose solution, maltodextrin solution, glycerol, ethanol, liposome, and at least one combination thereof, and other general additives such as antioxidants, buffer solution, bacteriostatic agents, etc. may be added if necessary. In addition, it may be formulated in the form of an injectable formulation such as aqueous solution, suspension, emulsion, etc. by additionally adding diluent, dispersing agent, surfactant, binder and lubricant, and antibodies and other ligands specific to a target cell may be used in combination with the carrier to be specifically reacted with the target cell. Furthermore, the composition may be preferably formulated according to each disease or ingredient using a suitable method in the art or a method which is taught in Remington's Pharmaceutical Science, Mack Publishing Company, Easton Pa.

The pharmaceutical composition of the present invention may be parenterally administered, and the parenteral administration is effected by subcutaneous injection, intravenous injection, intramuscular injection, or intrapleural injection. For parenteral administration, the pharmaceutical composition of the present invention may be mixed with a stabilizer or buffer to prepare a solution or suspension, which may then be provided as ampoules or vials each containing a unit dosage form.

The pharmaceutical composition of the present invention may be prepared in various forms according to the route of administration. For example, the pharmaceutical composition of the present invention may be formulated to a sterilized aqueous solution or dispersion for injection, or may be prepared in a freeze-dried form through a freeze-drying technique. The freeze-dried pharmaceutical composition may be stored typically at about 4° C. and may be reconstituted with a stabilizer that may contain an adjuvant such as saline solution and/or HEPE.

In a method of the present invention, factors affecting the amount of the pharmaceutical composition to be administered include, but are not limited to, administration mode, administration frequency, specific disease under treatment, severity of disease, history of disease, whether the subject is under treatment in combination with other therapeutics, the subject's age, height, weight, health, and physical conditions. As the patient's weight under treatment increases, the pharmaceutical composition of the present invention may preferably be administered in increasing amounts.

The present invention also provides a method for treating a TMPRSS4-overexpressed cancer, the method including administering a pharmaceutically active amount of the human antibody to a subject with the cancer.

The TMPRSS4-overexpressed cancer is preferably one selected from the group consisting of, but not limited to colorectal cancer, lung cancer, liver cancer, gastric cancer, and malignant thyroid neoplasms, and includes all the TMPRSS4-overexpressed cancers.

In a specific example of the present invention, it was confirmed that TMPRSS4 monoclonal antibodies inhibited invasion, migration, and proliferation in a colorectal cancer cell line (see FIGS. 15 to 19). Thus, the monoclonal antibody of the present invention may be useful for prevention and treatment of TMPRSS4-overexpressed cancers.

The subject applicable in the present invention is a vertebrate, preferably a mammal, more preferably an experimental animal such as mouse, rabbit, guinea pig, hamster, dog, and cat, and most preferably a primate such as chimpanzee and gorilla.

The method for administering the human antibody of the present invention may be conducted by parenteral administration (for example, intravenous, subcutaneous, intraperitoneal, or local administration) according to the purpose of use, and preferably by intravenous administration. In administration for solid cancer, local administration may be often preferable for rapid and facilitated access of the antibody. The dose may vary depending on weight, age, sex, and health condition of a patient, diet, administration time, administration method, excretion rate, and severity of disease. The single dose is in the range of 5 to 500 mg/nf, which may be administered daily or weekly. The effective amount may be controlled at the discretion of a doctor treating the patient.

The human antibody of the present invention may be used alone or in combination with surgery, hormone therapy, chemical therapy, and a biological response controller for treatment of a patient.

The present invention also provides a composition including the human antibody, light and heavy chains of the human antibody, or an immunologically active fragment thereof, and a radioactive isotope.

Figure 10:
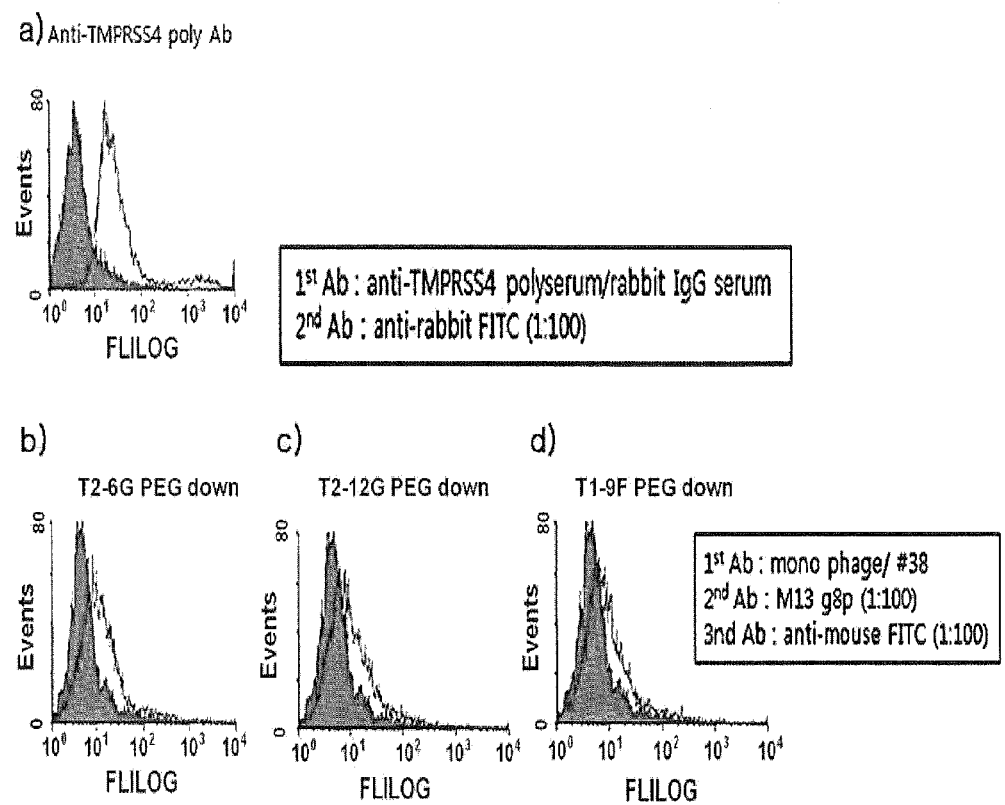
FIG. 10 is a group of graphs illustrating results, confirming that a TMPRSS4 polyclonal antibody and monoclonal antibodies specifically bind to colorectal cancer cell lines: a: polyclonal antibody; b: monoclonal antibody T2-6G; c: monoclonal antibody T2-12A; and d: monoclonal antibody T1-9F.

In a specific example of the present invention, it was confirmed that the monoclonal TMPRSS4 antibody specifically recognized TMPRSS4 and were bound to it in a TMPRSS4-overexpressed colorectal cell line (see FIG. 10). Thus, the monoclonal antibody of the present invention may be useful as a composition for detection of a TMPRSS4-overexpressed cancer.

The composition may be useful for radioimmuno treatment and detection of a TMPRSS4-overexpressed cancer. The TMPRSS4-overexpressed cancer is preferably one selected from the group consisting of, but not limited to, colorectal cancer, lung cancer, liver cancer, pancreatic cancer, gastric cancer, and malignant thyroid neoplasms, and includes all the TMPRSS4-overexpressed cancers.

Examples of preferred radioactive isotopes include $^{3}$H, $^{11}$C, $^{14}$C, $^{18}$F, $^{64}$Cu, $^{76}$Br, $^{86}$Y, $^{99m}$Tc, $^{111}$In, $^{123}$I, $^{177}$Lu, and a mixture or combination thereof. The radioactive isotope is characterized by the fact that it is bound to a human antibody and included in a carrier to which the human antibody is bound.

The present invention also provides an immunodetection method for detecting an ex vivo TMPRSS4-overexpressed cancer, the method including: contacting a composition including the radioactive isotope with cancer cells.

The TMPRSS4-overexpressed cancer is preferably one selected from the group consisting of, but not limited to, colorectal cancer, lung cancer, liver cancer, pancreatic cancer, gastric cancer, and malignant thyroid neoplasms, and includes all the TMPRSS4-overexpressed cancers.

In a specific example of the present invention, it was confirmed that the monoclonal TMPRSS4 antibody specifically recognized TMPRSS4 and were bound to it in a TMPRSS4-overexpressed colorectal cell line (see FIG. 10). Thus, the monoclonal antibody of the present invention may be useful as a composition for detection of a TMPRSS4-overexpressed cancer.

The composition including the radioactive isotope may be bound to a solid substrate in order to facilitate the subsequent steps such as washing or separation of complexes. The solid substrate includes, for example, synthetic resin, nitrocellulose, glass substrate, metal substrate, glass fiber, microsphere, microbead, etc. The synthetic resin includes polyester, polyvinyl chloride, polystyrene, polypropylene, PVDF, nylon, etc.

In addition, cancer cell may be appropriately diluted before it is contacted with the composition for detection.

The present invention also provides a method for imaging a TMPRSS4-overexpressed cancer, the method including 1) administering a diagnostically effective amount of a compound including the radioactive isotope to a subject; and 2) obtaining a detection image for the subject. The TMPRSS4-overexpressed cancer is preferably one selected from the group consisting of, but not limited to, colorectal cancer, lung cancer, liver cancer, pancreatic cancer, and malignant thyroid neoplasms, and includes all the TMPRSS4-overexpressed cancers.

In a specific example of the present invention, it was confirmed that the monoclonal TMPRSS4 antibody specifically recognized TMPRSS4 and were bound to it in a TMPRSS4-overexpressed colorectal cell line (see FIG. 10). Thus, the monoclonal antibody of the present invention may be useful as a composition for detection of a TMPRSS4-overexpressed cancer.

The detection image is characterized by the fact that it is obtained by near-infrared light imaging, PET, MRI, or ultrasonic imaging.

The present invention also provides a method for treating an in vivo TMPRSS4-overexpressed cancer, the method including:
1) intravenously administering a composition including the radioactive isotope to a subject;
2) detecting the composition of Step 1) to identify tumor cells; and 3) eliminating the tumor cells identified in Step 2) by surgical operation.

The TMPRSS4 overexpressed cancer is preferably one selected from the group consisting of, but not limited to, colorectal cancer, lung cancer, pancreatic cancer, gastric cancer, and malignant thyroid neoplasms, and includes all the TMPRSS4-overexpressed cancers.

In a specific example of the present invention, it was confirmed that TMPRSS4 monoclonal antibodies inhibited invasion, migration, and proliferation in a colorectal cancer cell line (see FIGS. 15 to 19). Thus, the monoclonal antibody of the present invention may be useful for prevention and treatment of TMPRSS4-overexpressed cancers.

Furthermore, the present invention provides a method for prognostic evaluation of a cancer patient, the method including:
1) intravenously administering a composition including the radioactive isotope to a patient whose tumor has been eliminated;
2) detecting the composition of Step 1) to identify tumor cells; and
3) judging that all tumor cells have been eliminated when tumor cells are not detected in step 2).

MODE FOR INVENTION

Hereinafter, the present invention will be described in more detail with reference to examples.

However, the following examples are provided for illustrative purposes only, and the scope of the present invention should not be limited thereto in any manner.

Example 1

Preparation of TMPRSS4 Antigen Protein <1-1>
TMPRSS4 Gene Cloning

A plasmid (IRAU-61-E06; Clone ID: hMU011286) containing a human TMPRSS4 gene was provided from KUGI (Korean UniGene Information) of the Center for Functional Analysis of Human Genome in Korea Research Institute of Bioscience and Biotechnology. The plasmid was used as a template DNA. In order to express only the protease domain (aa205~434) of the TMPRSS4, a forward primer (SEQ ID No. 1: 5'-GAGGAGCATATGGATTATAAAGATCAT-GATATTGATTATAAAGATGATGATGATAAAGTG GT GGGTGGGGAGGAG-3') and a reverse primer (SEQ ID No. 2: 5'-GAGGAGCTCGAGCAGCTCAGCCTTCCAGAC-3') were used to amplify the gene under the following conditions. The gene was treated with MieI and XhoI, followed by subcloning into a pET21c (Novagen, USA) using a ligase. PCR conditions are as follows: when a total reaction reagent was 50 μl, 100 ng of the template was introduced and a reaction at 94° C. for 2 minutes, 30 cycles of reactions at 94° C. for 30 seconds, at 55° C. for 30 seconds, and at 72° C. for a half minutes, and at a reaction at 72° C. for 10 minutes were performed to get a PCR product. Furthermore, the base sequence of the subcloned vector was identified (FIG. 1).

<1-2> Expression and Purification of TMPRSS4 Protein

The subcloned vector was transformed with BL21 (DE3). The vector was inoculated in an LB (+amp) medium and incubated overnight, followed by dilution at 1:100 in 500 ml of LB (+amp) medium for inoculation. The mixture was additionally incubated at 37° C. for 2 hours until OD reached 0.5 and treated with IPTG at a concentration of 1 mM, followed by incubation for 4 hours. E. coli was obtained through centrifugation at 5000 rpm for 10 minutes and suspended in 10 ml of Bug buster solution for 15 minutes, followed by centrifugation at 12000 rpm for 30 minutes to separate the mixture into an aqueous fraction and an insoluble fraction. SDS-PAGE analysis showed that TMPRSS4 protein was present in the insoluble fraction.

Figure 2:
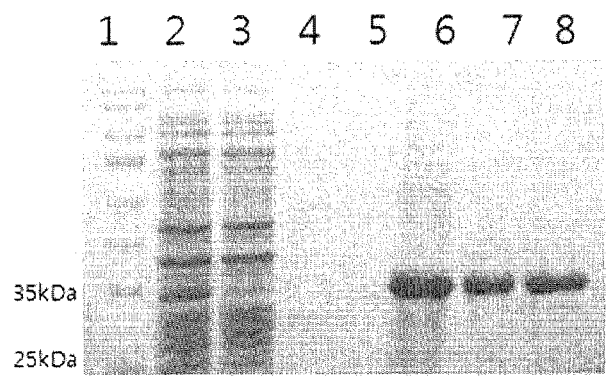
FIG. 2 is a photo illustrating results of a purified 2XFLAG-TMPRSS4 identified by SDS-PAGE.

The insoluble fraction was dissolved in 8 M urea solution (0.1 M $NaH_2PO_4$, 0.01 M TrisCl, pH 7.9), bound to 1 mL of Ni-NTA resin (Qiagen, USA), washed with 10 mL of washing buffer (8 M urea, 0.1 M $NaH_2PO_4$, 0.01 M TrisCl, pH 5.9), and eluted with 5 mL of elution buffer (8 M urea, 0.1 M $NaH_2PO_4$, 0.01 M TrisCl, pH 4.5). The eluted TMPRSS4 protein (TMPS4-FLAG) was dialyzed with PBS (+10% glycerol) and electrophresized in a 10% SDS-PAGE gel, followed by coomassie staining to confirm that it was about 35 kDa in size (FIG. 2).

As shown in FIG. 3a, 1 mL, of the purified TMPS4-FLAG protein was reacted with 40 ng of enterokinase (NEB, USA) at room temperature for 6 hours. Ni-NTA resin was used to purify only TMPRSS4 (TM-EK). The purified protein was electrophoresized in a 10% SDS-PAGE gel, followed by coomassie staining to confirm that it was about 31 kDa in size (FIG. 3b).

Example 2

Measurement of Enzyme Activity by TMPRSS4 Protein

In order to measure a trypsin-like proteolytic activity in the extracellular domain of TMPRSS4, Boc-Gln-Ala-Arg-Amc (t-butyloxycarbonylv(t-Boc)-Gln-Ala-Arg-7amido-4-methylcoumarin; B4153, Sigma, USA) as a fluorescent peptide trypsin substrate and Z-Phe-Arg-Amc (Z-Phe-Arg7-amido4-methylcoumarin hydrochloride; C9521, Sigma, USA) as a kallikrein substrate were each dissolved in substrate buffer (50 mM tris, 10 mM $CaCl_2$, 1 U M $ZnCl_2$) at a concentration of 100 μM and then mixed with TMPS4-FLAG protein (2.25 μg).

Enterokinase (0.09 ng) was added into the mixture and a Victor3 plate reader (PerkinElmer, USA) was used to measure fluorescent signals produced by hydrolysis of peptide substrate at 380/460 nm.

As a result, as shown in FIG. 4, it was confirmed that hydrolysis of the substrate by trypsin-like activity of active TMPRSS4 (TM-EK) showed activities over time compared to a control group, and that TMPRSS4 was successfully synthesized as a target antigen.

Example 3

Construction of library phage 2.7×10$^{10}$ human naive scFv library cells having diversity were incubated in a medium (3 L) containing 2XYTCM [17 g of Tryptone (CONDA, 1612.00), 10 g of yeast extract (CONDA, 1702.00), 5 g of NaCl (Sigma, S7653-5 kg), 34 µg/ml of chloramphenicol (Sigma, C0857)], 2% glucose (Sigma, G5400), and 5 mM MgCl$_2$ (Sigma, M2393) at 37° C. for 2-3 hours (OD$_{600}$=0.5~0.7). Then, the cells were infected with helper phage, followed by incubation in a medium containing 2×YTCMK [2 XYT CM, 70 µg/ml of Kanamycin (Sigma, K1876), 1 mM IPTG (ELPISBIO, IPTG025)] at 30° C. for 16 hours. The incubated cells were centrifuged (4500 rpm, 15 min, 4° C.) to obtain a supernatant. The supernatant was treated with PEG (Fluka, 81253) and NaCl (Sigma, S7653) until the two reagents became 4% and 3%, respectively. The reactant was centrifuged again (8000 rpm, 20 min, 4° C.). The pellet was dissolved in PBS, which proceeded to centrifugation again (12000 rpm, 10 min, 4° C.). As a result, the supernatant containing library phage was obtained, which was transferred to a new tube and stored at 4° C.

Example 4

Preparation of Polyclonal Antibody

Abfrontier (Korea) was requested to use TMPS4-FLAG as an antigen. The antigen was injected three times into two rabbits to obtain a polyclonal antibody serum. Antigen specific affinity purification was again performed with the serum to obtain 1 ml of a polyclonal antibody specifically bound to TMPS4-FLAG at 2 mg/mL. The obtained polyclonal antibody was identified by 10% SDS-PAGE under non-reducing conditions.

Figure 5:
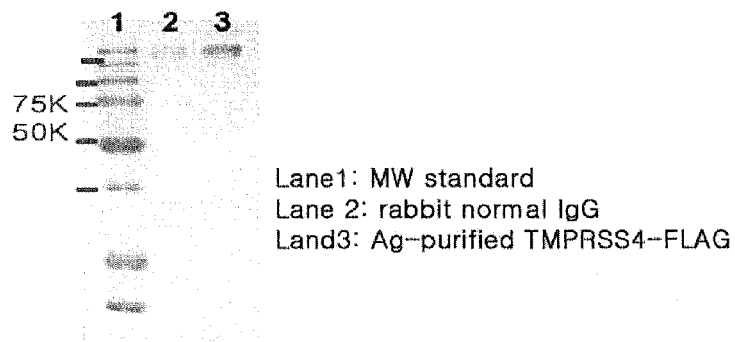
FIG. 5 is a graph illustrating results of phage screening in 1st to 3rd pannings.

As a result, as shown in FIG. 5, a purified antibody was identified. Subsequently, this was used as a positive control group.

Example 5

Preparation of Monoclonal Antibody

<5-1> Panning Process

An immunosorb tube (Nunc 470319) was coated with each of 30 µg of the purified TMPRSS4-antigens (TMPS4-FLAG and TM-EK) obtained in Example 2 using 4 ml of a coating buffer [1.59 g of Na$_2$CO$_3$ (Sigma, S7795), 2.93 g of NaHCO$_3$ (Sigma, S8875), 0.2 g of NaN$_3$ (Sigma, S2002)] at 4° C. for 16 hours with rotator. Then, the antigen was dissolved in PBS at room temperature for 2 hours, followed by blocking in the immunotube using skim milk [(BD, 232100) –4% in IXPBS]. 2 ml of library phage constructed in Example 3 was added into the immunotube, followed by reaction at room temperature for 2 hours. The immunotube was washed five times with PBST (0.05%) and twice with PBS. After washing, antigen specific scFV-phage was eluted using 100 mM TEA (Sigma T-0886). E. coli (XLI-blue, stratagene, 200249) was transfected with the eluted phage, followed by amplification. The 2nd and 3rd pannings was performed on the phage amplified at the first panning by the same manner as described above except that washing times with PBST were increased (2nd: 13 times, 3rd: 23 times).

As a result, as shown in Table 1, it was confirmed that colony titer of the phage against the antigen was increased at least 100 times in the 3rd panning.

TABLE 1

| Target antigen | Panning | Initial phage number | Binding phage number |
|---|---|---|---|
| TMPRSS4-FLAG | 1$^{st}$ | 4 × 10$^{13}$ | 4.6 × 10$^6$ |
| | 2$^{nd}$ | 7.7 × 10$^{12}$ | 5 × 10$^7$ |
| | 3$^{rd}$ | 7.2 × 10$^{12}$ | 1.9 × 10$^9$ |
| TM-EK | 1$^{st}$ | 2.3 × 10$^{13}$ | 5 × 10$^6$ |
| | 2$^{nd}$ | 1.2 × 10$^{13}$ | 4.8 × 10$^6$ |
| | 3$^{rd}$ | 1.24 × 10$^{13}$ | 2.96 × 10$^8$ |

<5-2> Screening of Phage Antibody by Phage ELISA
<5-2-1> Identification of Panning Results Cell stocks obtained from the 1$^{st}$-3$^{rd}$ pannings and stored as frozen were dissolved in a medium containing 5 mL of 2XYTCM, 2% glucose, and 5 mM MgCl$_2$ to make OD$_{600}$ as 0.1. Then, the cells were incubated at 37° C. for 2-3 hours (OD$_{600}$=0.5-0.7), which were infected with MI helper phage. Then, the cells were incubated in a medium containing 2XYTCMK, 5 mM MgCl$_2$ and 1 mM IPTG at 30° C. for 16 hours. The incubated cells were centrifuged (4500 rpm, 15 min, 4° C.), and the supernatant was transferred to a new tube (1st ~3rd panning poly scFv-phage). A 96-well immuno-plate (NUNC 439454) was coated with two kinds of antigens (100 ng/well) using a coating buffer at 4° C. for 16 hours, followed by blocking with skim milk dissolved in PBS (4%). Each well of the 96-well immuno-plate was washed with 0.2 of PBS-tween20 (0.05%). 100 µl of the 1st-3rd panning poly scFV-phage was added into each well, followed by reaction at room temperature for 2 hours. Again, each well was washed four times with 0.2 ml. of PBS-tween20 (0.05%). The secondary antibody anti-MI3-HRP (Amersham 27-9421-01) was diluted at 1:2000, followed by reaction at room temperature for 1 hour. An OPD tablet (Sigma 8787-TAB) was added into a PC buffer [5.1 g of C$_6$H$_8$O$_7$H$_2$O (Sigma, C0706), 7.3 g of Na$_2$HPO$_4$ (Sigma, S7907)] to make a substrate solution, which was added into each well by 100 ul/well, followed by color development for 10 minutes. The optical density was measured at 490 inn by using a spectrophotometer (MolecularDevice, USA).

As a result, as shown in FIG. 6, it was confirmed that binding capacities to the antigen were enhanced in the 3rd panning.

<5-2-2> Selection of Monoclonal Antibodies

Colonies obtained from a polyclonal antibody group (the 3rd panning) having strong binding capacity were incubated in a 96-deep well plate (Bioneer, 90030) containing 1 ml of a medium supplemented with 2XYTCM, 2% glucose and 5 mM MgCl$_2$ at 37° C. for 16 hours. 100-200 ul of the solution was incubated in 1 of a medium supplemented with 2XYTCM, 5 mM MgCl$_2$, and 1 mM IPTG, which was loaded in a 96-deep well plate at 37° C. for 2-3 hours, followed by inoculation at an initial OD$_{600}$ value of 0.1. The cells were infected with MI helper phage (MOI=I: 20) and the infected cells were cultured in a medium supplemented with 2XYTCMK, 5 mM MgCl$_2$, and 1 mM IPTG at 30° C. for 16 hours. The cultured cells were centrifuged (4500 rpm, 15 min, 4° C.) and a supernatant was obtained, to which 4% PEG 6000 and 3% NaCl were added. Upon completion of dissolving, reaction was induced in ice for 1 hour. The reactant was centrifuged (8000 rpm. 20 min, 4° C.) and pellet was dissolved in PBS. Centrifugation (12000 rpm, 10 min, 4° C.) was performed again and a supernatant was obtained, from which the 3rd panning monoclonal scFv phage was obtained. The phage was transferred to a new tube and stored at 4° C.

A 96-well immuno-plate was coated with the two antigens (100 ng/well) at 4° C. for 16 hours, followed by blocking with skim milk dissolved in PBS (4%). Each well of the 96-well immuno-plate was washed with 0.2 mL of PBS-tween20 (0.05%). 100 μL of the 3rd panning monoclonal scFV-phage was added to each well, followed by reaction at room temperature for 2 hours. Each well was washed four times with 0.2 ml of PBS-tween20 (0.05%). The secondary antibody anti-MI3-HRP was diluted at 1:2000, followed by reaction at room temperature for 1 hour. The plate was washed with 0.2 ml of PBS-tween20 (0.05%), followed by color development. The optical density was measured at 490 ran.

As a result, a total of 50 monoclonal phages having strong binding capacities to each antigen (15 phages against TMPS4-FLAG (Table 2) and 35 phages against TMPS4-EK (Table 3) were selected.

TABLE 2

| a-Myc | | | | 2xFlag peptide | | | | TMPRSS4 | | | |
| --- | --- | --- | --- | --- | --- | --- | --- | --- | --- | --- | --- |
| 0.1331 | 0.1004 | 0.161 | 0.3503 | 0.0007 | 0.0114 | −0.0004 | −0.0002 | 1.1864 | 0.0666 | 1.1335 | 0.6845 |
| 0.1811 | 0.1661 | 2.4121 | 0.1238 | −0.002 | 0.0039 | 0.0022 | −0.0001 | 1.1915 | 1.3613 | 2.8497 | 1.2023 |
| 0.5538 | 0.2104 | 0.1695 | 1.9212 | 0.0023 | −0.0028 | 0.0062 | −0.001 | 2.2938 | 1.499 | 1.3426 | 2.8607 |
| 0.1287 | 0.1887 | 0.1286 | 0.098 | −0.0018 | −0.0017 | −0.0014 | 0.0006 | 0.0073 | 1.3574 | 1.1518 | 1.1222 |
| 2.6361 | 0.1567 | 0.214 | 0.1308 | −0.0018 | −0.0024 | −0.0028 | −0.0016 | 2.8245 | 1.2143 | 1.7721 | 1.495 |
| 0.1153 | 0.1461 | 2.3709 | 0.7187 | −0.0018 | −0.0019 | −0.0015 | 0.0009 | 0.9604 | 1.2248 | 2.9253 | 2.4849 |
| 0.2106 | 0.1823 | 0.098 | 0.3629 | −0.0028 | −0.0039 | −0.0024 | −0.0002 | −0.0008 | 1.4834 | 1.0884 | 2.2009 |
| 0.0007 | 0.294 | 2.1367 | 0.1701 | −0.0012 | −0.0014 | 0.0055 | 0 | 0.0012 | 0.2502 | 2.9155 | 1.2892 |
| 0.1987 | 0.2519 | 0.1019 | −0.0022 | −0.0023 | −0.0022 | −0.002 | −0.0019 | −0.0024 | 1.2927 | 0.0156 | −0.0007 |
| 0.5709 | −0.0025 | 0.1009 | 0.0701 | −0.0037 | −0.0048 | −0.0038 | −0.0039 | 0.0034 | −0.0026 | 0.0037 | −0.0022 |
| −0.0035 | 0.2491 | 0.202 | 0.026 | −0.0033 | −0.0042 | −0.0037 | −0.004 | 0.0036 | 1.5313 | −0.0025 | −0.0019 |
| −0.0025 | −0.0029 | 0.0286 | 0.0596 | −0.0036 | −0.0032 | −0.0028 | −0.0023 | −0.0035 | −0.0037 | −0.0018 | −0.0034 |
| −0.0051 | 0.2243 | 0.0266 | −0.0003 | −0.0024 | 0.0035 | −0.0038 | −0.0046 | −0.0043 | 1.2621 | 0.0365 | −0.0033 |
| 0.2588 | 0.0142 | −0.0042 | 0.019 | −0.0036 | −0.0025 | 0.002 | −0.004 | 1.3278 | 0.1661 | −0.0036 | −0.0034 |
| 0.4319 | −0.0041 | −0.0034 | −0.0042 | −0.0043 | −0.0021 | −0.0034 | −0.0031 | 1.7376 | −0.0031 | −0.0039 | −0.0037 |
| 0.4176 | −0.0023 | 0.0848 | −0.0029 | −0.0023 | 0.006 | −0.0002 | 0 | 1.8127 | −0.0023 | 0.0037 | −0.0026 |

TABLE 3

| α-myc | | | | | | TM-EK | | | | | |
| --- | --- | --- | --- | --- | --- | --- | --- | --- | --- | --- | --- |
| 0.3591 | 0.783 | 2.2268 | 1.4212 | 1.9753 | 2.1453 | 0.0079 | 0.0542 | 2.3081 | 0.0442 | 2.7452 | 2.6617 |
| 0.5592 | 0.3708 | 0.004 | −0.0098 | 2.7023 | 1.0532 | 0.0061 | 0.0049 | −0.0077 | −0.0074 | 2.7663 | 1.3702 |
| −0.0098 | −0.0009 | 0.1083 | 0.1651 | 0.8825 | 1.4964 | −0.0086 | −0.0081 | 0.0451 | 0.0411 | 0.5213 | 2.7806 |
| 0.2322 | 0.5214 | 0.1214 | 0.6134 | 0.6602 | −0.0042 | 0.0017 | 0.0324 | −0.0078 | −0.0027 | 0.0107 | 0.0009 |
| −0.0083 | −0.0105 | −0.0104 | −0.007 | 1.087 | 1.0222 | −0.0091 | −0.0060 | −0.0072 | −0.0075 | 0.0321 | 0.0595 |
| −0.0116 | −0.0008 | 0.003 | 0.0337 | 0.9934 | 1.2158 | −0.007 | −0.0093 | −0.0066 | −0.0055 | 2.4717 | 2.617 |
| −0.0098 | −0.0104 | 0.0871 | −0.0102 | 1.0224 | 2.5485 | −0.0079 | −0.0104 | 0.0396 | −0.0093 | 0.4413 | 2.2067 |
| 1.3365 | 0.6618 | −0.0077 | −0.0096 | 1.3266 | −0.0087 | 0.0031 | 0.0477 | −0.0081 | −0.0046 | 2.4913 | 0 |
| 2.5569 | 2.2743 | 2.6546 | 2.4443 | −0.0113 | 0.6904 | 2.7672 | 2.7294 | 2.7506 | 2.7078 | 0 | 2.423 |
| 2.5541 | 1.187 | 1.6959 | 2.2482 | 0.9865 | −0.0104 | 2.3385 | 0.6491 | 1.7594 | 2.6667 | 0.2899 | −0.0084 |
| 1.2619 | 2.283 | 1.0976 | 1.039 | 0.6417 | 1.7241 | 2.4788 | 2.6489 | 2.4717 | 2.4135 | 0.8713 | 2.2305 |
| 1.286 | 0.3775 | 2.4574 | 0.9369 | 1.0916 | 0.5452 | 1.5297 | 0.003 | 2.4674 | 0.2737 | 2.5672 | 0.0206 |
| 1.358 | 0.6647 | 1.1115 | 2.1723 | 1.1206 | 1.3818 | 2.5558 | 0.2181 | 2.5539 | 2.2052 | 0.1395 | 2.7175 |
| 1.2434 | 2.3015 | 2.4622 | 2.0075 | 1.1916 | 1.8476 | 2.6169 | 2.4958 | 2.8229 | 1.3234 | 0.0937 | 2.471 |
| 1.1921 | 0.6616 | 2.26 | 0.0501 | 1.1977 | 1.039 | 0.7781 | 0.0054 | 2.7182 | 0.0167 | 2.4293 | 1.1626 |
| 1.3202 | 1.3396 | 0.2422 | −0.0068 | 1.2494 | 2.2726 | 0.724 | 1.6058 | 0.0319 | 0.0065 | 2.5365 | 2.6947 |

<5-3> Identification of Monoclonal Phages and Examination Thereof

<5-3-1> Verification by Fingerprinting

1 µl of the fifty monoclonal cells firstly selected, 0.2 µl of Tag DNA polymerase (Gendocs, Korea) (5 U/ul), 0.2 µl of each forward primer (peIB5, SEQ. ID. No. 5: 5'-CTA-GATAACGAGGGCAAATCATG-3') and reverse primer (cla3, SEQ. ID. No. 6: 5'-CGTCACCAATGAAACCATC-3') at 50 p/µl, 3 µl of 10× buffer, 0.6 µl of 10 mM dNTP mix, and 24.8 µl of distilled water were mixed to perform a colony PCR (iCycler iQ, BIO-RAD). PCR conditions are as shown in Table 4.

TABLE 4

| Temperature | Time | Cycle |
|---|---|---|
| 95° C. | 5 min | |
| 95° C. | 30 sec | 30 |
| 56° C. | 30 sec | |
| 72° C. | 1 min | |
| 72° C. | 10 min | |
| 4° C. | | |

The colony PCR product was identified on a 1% agarose gel (Seakem L E, CAMERES 50004). 0.2 µl of BstNI(Rochell1288075001, 10 U/µl) was added to perform a reaction at 37° C. for 2-3 hours. Reaction conditions are as shown in Table 5. The fragmented product was identified on an 8% DNA polyacrylamide gel.

TABLE 5

| 10X Buffer | 3 µl |
|---|---|
| colony PCR product | 10 µl |
| BstNI (10 U/µl) | 0.2 µl |
| Distilled water | 16.8 µl |

As a result, as shown in Table 7, fragments of monoclonal phage antibodies digested by BstNI were proved to have diversity.

<5-3-2> Verification by Base Sequence Analysis 50 kinds of the monoclonal phages were incubated in a medium (5 ml) supplemented with 2XYTCM, 2% glucose, and 5 mM $MgCl_2$ at 37° C. for 16 hours. A DNA purification kit (Nuclogen 5112) was used for the incubated monoclones to obtain a DNA, and then sequencing of the obtained DNA was performed by using a peIB5 primer of SEQ ID No. 5 (Solgent, Korea). As a result, as shown in Table 6 and FIG. 8, CDR regions of $V_H$ and $V_L$ of the selected antibody were identified.

Similarity between the antibody and germ line antibody group was investigated by Ig BLAST program of NCBI (//www.ncbi.nlm.nih.gov/igblast/). As a result, 13 kinds of TMPRSS4 specific phage antibodies were obtained, and the result was summarized and presented in Table 7.

TABLE 6

| Group | Clone name | Heavy Chain CDR1 | CDR2 | CDR3 | Light Chain CDR1 | CDR2 | CDR3 |
|---|---|---|---|---|---|---|---|
| 2 | T1-11G | RYTMH: SEQ ID No. 7 | VISSDGSKKYY GDSVKG: SEQ ID No. 19 | GGGKGHWLDT: SEQ ID No. 32 | RASQSISKWLA: SEQ ID No. 58 | AASNLQS: SEQ ID No. 71 | LQSNSLPIT: SEQ ID No. 84 |
| 3 | T1-12C | NYGMH: SEQ ID No. 8 | VISYDGSTKYY ADSVRG: SEQ ID No. 20 | GSDVAY: SEQ ID No. 33 | RSSQSLVYSDG NTYLN: SEQ ID No. 59 | KVSNRDS: SEQ ID No. 72 | MQSLRTPLT: SEQ ID No. 85 |
| 3 | T2-9G | NYGMH: SEQ ID No. 8 | VISYDGSTKYY ADSVRG: SEQ ID No. 20 | GSDVAY: SEQ ID No. 33 | RSSQSLVYSDG NTYLN: SEQ ID No. 59 | KVSNRDS: SEQ ID No. 72 | MQSLRTPLT: SEQ ID No. 85 |
| 4 | T1-9F | SYAMS: SEQ ID No. 9 | AITGSGGSTFY ADSVKG: SEQ ID No. 21 | GGNLDV: SEQ ID No. 34 | RSSQSLVHSNG NTYLT: SEQ ID No. 60 | KISKRFS: SEQ ID No. 77 | MQLTQFPLT: SEQ ID No. 86 |
| 4 | T2-12F | SYAMS: SEQ ID No. 9 | AITGSGGSTFY ADSVKG: SEQ ID No. 21 | GGNLDV: SEQ ID No. 34 | RSSQSLVHSNG NTYLT: SEQ ID No. 60 | KISKRFS: SEQ ID No. 77 | MQLTQFPLT: SEQ ID No. 86 |
| 9 | T2-8F | NYAMN: SEQ ID No. 10 | AISGSGGSTYY ADSVKG: SEQ ID No. 22 | LRGAFDI: SEQ ID No. 35 | RSSQSLLHSNG YNYLD: SEQ ID No. 64 | LGSKRAA: SEQ ID No. 74 | MQALQTPT: SEQ ID No. 87 |
| 12 | T2-12C | RYGIH: SEQ ID No. 11 | VISYDGNIKYY ADSVKG: SEQ ID No. 23 | LWRQSAADAFD I: SEQ ID No. 36 | TGTSSDVGGSS YVS: SEQ ID No. 62 | DVTRRPS: SEQ ID No. 75 | ASYAGSHYL: SEQ ID No. 88 |
| 5 | T2-3A | SYAMH: SEQ ID No. 12 | SISWSSNNIRY ADSVKG: SEQ ID No. 24 | RAAAKAFDI: SEQ ID No. 37 | TGTSTDIGGYN YVS: SEQ ID No. 63 | DVNNRPS: SEQ ID No. 76 | SSYTSSSFV: SEQ ID No. 89 |
| 8 | T2-7B | DSVAWN: SEQ ID No. 13 | RTYYKSKWYND YAVSVRS: SEQ ID No. 25 | GGGKGMDV: SEQ ID No. 38 | TGTSGDIGGFN YVS: SEQ ID No. 64 | DVSRRPS: SEQ ID No. 77 | ASYAGTKFWL: SEQ ID No. 90 |
| 7 | T2-6G | NYGMH: SEQ ID No. 8 | VISYDGSKKYY ADSVKG: SEQ ID No. 26 | GTTMDV: SEQ ID No. 39 | SGSNSNIGSNT VN: SEQ ID No. 65 | GHNQRPS: SEQ ID No. 78 | ASWDDTVSGPK WV: SEQ ID No. 91 |

TABLE 6-continued

| Group | Clone name | Heavy Chain | | | Light Chain | | |
|---|---|---|---|---|---|---|---|
| | | CDR1 | CDR2 | CDR3 | CDR1 | CDR2 | CDR3 |
| 10 | T2-10E | DYAMH: SEQ ID No. 14 | GISWNSGSIGY ADSVKG: SEQ ID No. 27 | GLRGLRYRNYY YGMDV: SEQ ID No. 40 | QASQDITNYLN: SEQ ID No. 66 | AASSLIIT: SEQ ID No. 79 | QQSHSPPFT: SEQ ID No. 92 |
| 11 | T2-6C | DYAIH: SEQ ID No. 15 | GISWNSEIVGY GDSVKG: SEQ ID No. 28 | GSSGRAFDI: SEQ ID No. 41 | RASQSISTYLN: SEQ ID No. 67 | GATSLQS: SEQ ID No. 80 | QQSYNLPRT: SEQ ID No. 93 |
| 1 | T1-5G | DHYMS: SEQ ID No. 16 | YISNRGYSIYY ADSVKD: SEQ ID No. 29 | DLRSSDAHTWG GVDAFDI: SEQ ID No. 42 | RASQSISSWLA: SEQ ID No. 68 | KASSLES: SEQ ID No. 81 | QQFNNNLFS: SEQ ID No. 94 |
| 6 | T2-6A | SYDVH: SEQ ID No. 17 | WVNPNSGNADY AQKFQG: SEQ ID No. 30 | GRFGAFDV: SEQ ID No. 43 | RASQGISRWLA: SEQ ID No. 69 | AASNLQS: SEQ ID No. 82 | QQANSFPLT: SEQ ID No. 95 |
| 13 | T2-12A | NYAMS: SEQ ID No. 18 | AISGSGASTNY ADSVKG: SEQ ID No. 31 | LGREQYLAR GYFEH: SEQ ID No. 44 | QGDSLRSYYAS: SEQ ID No. 70 | GKNNRPS: SEQ ID No. 83 | SSRDSSGNH LV: SEQ ID No. 96 |

[Table 7]

A. Four antibodies were obtained against antigen TMPS4-Flag

| Clone Name | VH | identities | VL | identities | VM (CDR3-a.a seq) | VL (CDR3-a.a seq) | Group |
|---|---|---|---|---|---|---|---|
| T1-5G | VH3-11 | 273/296 (92.23%) | L12A | 269/277 (97.11%) | DLRSSDAKTWGGVDAFDI (SEQ ID NO: 42) | QQFNNNLFS (SEQ ID NO: 94) | 1 |
| T1-11G | VH3-30 | 278/295 (94.24%) | L5 | 269/284 (94.72%) | GGGKGHWLDT (SEQ ID NO: 32) | LQSNSLPIT (SEQ ID NO: 84) | 2 |
| T1-12C | VH3-30 | 282/295 (95.59%) | A17 | 267/285 (93.68%) | GSDVAY (SEQ ID NO: 33) | MQSLRTPLT (SEQ ID NO: 85) | 3 |
| T1-9F | VH3-23 | 284/294 (96.60%) | A23 | 293/301 (97.34%) | GGNLDV (SEQ ID NO: 34) | MQLTQFPLT (SEQ ID NO: 86) | 4 |

B. Nine antibodies were obtained against antigen TMPS4-EK besides the four antibodies obtained against antigen TMPS4-Flag

| Clone Name | VH | identities | VL | identities | VM (CDR3- a.a seq) | VL (CDR3-a.a seq) | Group |
|---|---|---|---|---|---|---|---|
| T2-9G | VH3-30 | 283/295 (95.93%) | A17 | 267/285 (93.68%) | GSDVAY (SEQ ID NO: 33) | MQSLRTPLT (SEQ ID NO: 85) | 3 |
| T2-12F | VH3-23 | 285/294 (96.94%) | A23 | 293/301 (97.34%) | GGNLDV (SEQ ID NO: 34) | MQLTQFPLT (SEQ ID NO: 86) | 4 |
| T2-3A | VH3-9 | 262/286 (91.61%) | V1-4 | 280/290 (96.55%) | RAAAKAFDI (SEQ ID NO: 37) | SSYTSSSFV (SEQ ID NO: 89) | 5 |
| T2-6A | VH1-8 | 282/291 (96.91%) | L5 | 266/282 (94.33%) | GRFGAFDV (SEQ ID NO: 43) | QQANSFPLT (SEQ ID NO: 95) | 6 |
| T2-6G | VH3-30 | 283/295 (95.93%) | V1-16 | 255/283 (90.11%) | GTTMDV (SEQ ID NO: 39) | ASWDDTVSGPKWV (SEQ ID NO: 91) | 7 |
| T2-7B | VH6-1 | 289/304 (95.07%) | V1-3 | 265/286 (92.66%) | GGGKGMDV (SEQ ID NO: 38) | ASYAGTKFWL (SEQ ID NO: 90) | 8 |
| T2-8F | VH3-12 | 280/291 (96.22%) | A19 | 282/295 (95.59%) | LRGAFDI (SEQ ID NO: 35) | MQALQTPT (SEQ ID NO: 87) | 9 |

-continued

| Clone Name | VH | identities | VL | identities | VM (CDR3- a.a seq) | VL(CDR3-a.a seq) | Group |
|---|---|---|---|---|---|---|---|
| T2-10E | VH3-9 | 278/291 (95.53%) | 012 | 267/284 (94.01%) | GLRGLRYRNYYYGMDV (SEQ ID NO: 46) | QQSHSPPFT (SEQ ID NO: 92) | 10 |
| T2-6C | VH3-9 | 271/291 (93.13%) | 012 | 263/286 (91.96%) | GSSGRAFDI (SEQ ID NO: 41) | QQSYNLPRT (SEQ ID NO: 93) | 11 |
| T2-12C | VH3-30 | 280/294 (95.24%) | V1-3 | 272/287 (94.77%) | LWRQSAADAFDI (SEQ ID NO: 33) | ASYAGSHYL (SEQ ID NO: 85) | 12 |
| T2-12A | VH3-23 | 270/291 (92.78%) | V2-13 | 267/285 (93.68%) | LGREQYLARGYFLH (SEQ ID NO: 44) | SSRDSSGNHLV (SEQ ID NO: 96) | 13 |

Example 6

Analysis of Characteristics of Human Antibody Against TMPRSS4

<6-1> Western Blot Analysis of Phage

Two sheets of 10% SDS-PAGE gel into which the antigen TMPRSS4-FLAG is loaded (0.1-200 ng/well) were electrophoresized at 100 V for 2 hours and transferred to NC membrane (Millipore Cat. No. HATFOOOIO) at 85 V for 2 hours, followed by blocking with skim milk dissolved in TBST (4%) at 4° C. overnight. Subsequently, polyclonal α-TMPRSS4 antibody (1 mg/ml) constructed in Example 4 was diluted at 1:2000 in skim milk dissolved in TBST. A supernatant of the monoclonal phage antibody selected in Example 5 was diluted at 1:50 in skim milk dissolved in TBST, followed by reaction at room temperature for 1 and a half hours. The dilution was washed five times with TBST, each of anti-mouse IgG-HRP (Sigma) and anti-MI3-HRP (Amersham bioscience) was used for dilution at 1:3000 in skim milk in TBST (4%), followed by reaction at room temperature for 30 minutes. Then, it was washed by the same manner. After washing, developments were performed (Intron, Cat. No. 12145) to compare amounts of antigen proteins which could be detected by a polyclonal antibody and a monoclonal phage antibody.

Figure 9:
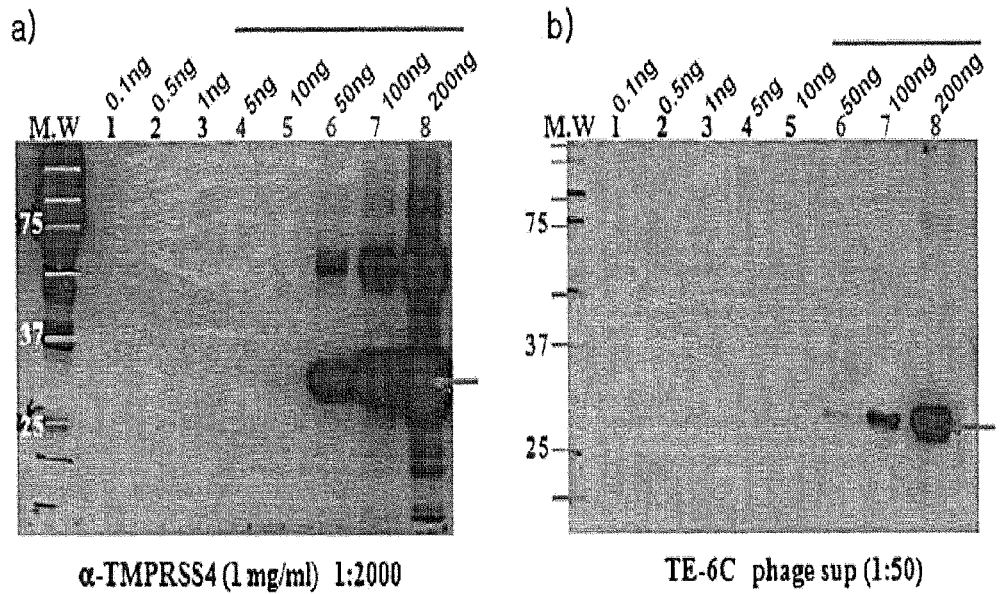
FIG. 9 is a group of photos illustrating results comparing binding specificities of TMPRSS4 polyclonal antibody and a monoclonal antibody: a: polyclonal antibody; and b: monoclonal antibody.

As a result, as shown in FIG. 9, the signal intensity in a TE-6C phage antibody was lower than that in a polyclonal antibody. However, about 30 KDa of antigen protein was obtained without any non-specific binding.

<6-2> Phage FACS Analysis

Colorectal cancer cell line (colo205; ATCC), known to overexpress TMPRSS4, was washed twice with PBS in a 100 mm plate. An enzyme-free PBS-based buffer (Gibco) was added into the plate, followed by incubation at 37° C. for 10 minutes. Subsequently, cells were collected by a scrapper and centrifuged at 1300 rpm for 3 minutes. The pellet was washed twice with a 2% PBF solution (IXPBS supplemented with 2% FBS), followed by resuspension with 2% PBF solution at a concentration of $\geq 5\times10^5$ cells. 100 μL of the monoclonal phage antibody of the present invention was concentrated 10 times by PEG, followed by dilution at 1:2. The dilution was mixed and stirred with the cells. The mixture was reacted in ice for 1 hour, followed by centrifugation at 1300 rpm at 4° C. for 3 minutes to remove a supernatant. The precipitate was washed three times with 200 μL of a 2% PBF solution. 100 μL of anti-g8p antibody (Abeam) diluted at 1:200 in a 2% PBF solution was mixed and stirred with the resulting solution, followed by reaction in ice for 30 minutes. The reactant was centrifuged at 1300 rpm at 4° C. for 3 minutes for removal of a supernatant, followed by washing three times with 200 μL of a 2% PBF solution. 100 μL 1 of FITC-linked anti-mouse IgG diluted at 1:1000 in a 2% PBF solution was mixed with each specimen, followed by reaction in ice for 30 minutes. After a washing was additionally performed, 500 μL of a 2% PBF solution was added into it. The mixture was transferred to a tube for FACS(Falcon) and vortexed, followed by analysis of stained cells by flow cytometer (Beckman Coulter). In each experiment, monoclonal phage antibodies were treated with a specimen under the same conditions and used as an internal control group. WINMDI2.9 software (//facs.s-cripps.edu/software.html, The Scripps Research Institute) was used to analyze the data.

As a result, as shown in FIG. 10, monoclonal phage antibodies T2-6G, T2-12A, ALC T1-9F, etc. specifically recognizing and bound to TMPRSS4 in a TMPRSS4 overexpressed colorectal cancer cell line were selected. Besides, T2-6C, T2-3A, T2-8F, etc. were selected, but only the results were not described in the specification.

<6-3> Analysis of Whole IgG Conversion

To covert monoclonal phage antibodies against TMPRSS4 into whole IgG vectors in phages, 1 ul of monoclonal DNA, 10 pmole/μl of each of heavy chain forward primer and reverse primer in Table 8, 5 μl of 10× buffer, 1 ul of 10 roM dNTP mix, 0.5 ul of pfu DNA polymerase (Solgent, 2.5 U/μl), and distilled water were mixed to perform a colony PCR (iCycler iQ, BIO-RAD). In addition, light chain forward and reverse primers in Table 8 were used to perform a colony PCR by the same manner.

TABLE 8

| Clone name | Heavy Chain | | Light Chain | |
|---|---|---|---|---|
| | Forward primer (Sfi I) | Reverse primer (Nhe I) | Forward primer (Sfi I) | Reverse primer (Bgl II) |
| T2-3A | NATVH1-2: SEQ ID No. 110 | TTGGTGG CCACAGC GGCCGAT GTCCACT | NATJH-ALL: SEQ ID No. 114 | CAGGAGGC TAGCTGAG GAGACGGT GA | NATVL4: SEQ ID No. 115 | TTGGTGGC CACAGCGG CCGATGTC CACTCGCA | NATJL1-R: SEQ ID No. 119 | GAGGAGAG ATCTTAGG ACGGTGAC CTTGGTCC |

TABLE 8-continued

| Clone name | Heavy Chain | | Light Chain | | |
|---|---|---|---|---|---|
| | Forward primer (Sfi I) | Reverse primer (Nhe I) | Forward primer (Sfi I) | | Reverse primer (Bgl II) |
| | | CGCAGAT GCAGCTG GTGCAGT C | | GTCTGCCC TGACTCAG CC | C |
| T2-6C | NATVH1-2: SEQ ID No. 111 | TTGGTGG CCACAGC GGCCGAT GTCCACT CGCAGGT GCAGCTG GTGCAGT C | NATVE1-1: SEQ ID NO. 116 | TTGGTGGC CACAGCGG CCGATGTC CACTCGGA CATCCAGA TGACCCAG TC | NATJK-R5: SEQ ID No. 120 | GAGGAGAG ATCTTTTG ATTTCCAG CTTGGT |
| T2-6G | NATVH3-2: SEQ ID No. 112 | TTGGTGG CCACAGC GGCCGAT GTCCACT CGCAGGT GCAGCTG GTGGAGT C | NATVL4: SEQ ID No. 117 | TTGGTGGC C'ACAGCG GCCGATGT CCACTCGC AGTCTGCC CTGACTCA GCC | NATJL2-R: SEQ ID No. 121 | GAGGAGAG ATCTTAGG ACGGTCAG CTTGGTCC C |
| T2-8F | NATVH3-2: SEQ ID No. 113 | TTGGTGG CCACAGC GGCCGAT GTCCACT CGCAGGT GCAGCTG GTGGAGT C | NATVK3: SEQ ID No. 118 | TTGGTGGC CACAGCGG CCGATGTC CACTCGGA TATTGTGA TGACCCAG ACTCC | NATJK-R4: SEQ ID No. 4 | GAGGAGAG ATCTTTTG ATTTCCAC CTTGGT |

After a heavy chain gene obtained through PCR was purified with DNA-gel extraction kit (Qiagen), 1 μi of pNATAB H vector (FIG. IIa) (10 ng), 15 μL of heavy chain (100-200 ng), 2 μl of 10× buffer, 1 μl of ligase (1 U/μl), and distilled water were mixed with the gene and left still at room temperature for 1-2 hours for linkage to the vector. The vector was left still in ice for 30 minutes along with a cell for transformation (XL1-blue), followed by heat shock at 42° C. for 90 sec for transfection. It was again left still in ice for 5 minutes and 1 ml of LB medium was injected, followed by incubation at 37° C. for 1 hour. The mixture was smeared in LB Amp liquid medium, followed by incubation at 37° C. for 16 hours. Single colony was inoculated into 5 ml of LB Amp liquid medium, followed by incubation at 37° C. for 16 hours. A DNA-prep kit (Nuclogen) was used for the medium to extract a DNA.

In addition, pNATAB L vector (FIG. IIb) was used by the same manner to extract a DNA of the light chain. Sequencing of the obtained DNA was performed by using a CMV-proF primer (SEQ ID No. 3: AAA TGG GCG GTA GGC GTG) (Solgent).

As a result, it was confirmed that the sequences of heavy and light chains of the 4 clone phages against TMPRSS4 converted into whole IgG were identical to those of the phage antibodies.

<6-4> Verification of Whole IgG 40 fig of PEI (Cat #23966, Polysciences, Inc) and 10 fig of each antibody heavy chain DNA and light chain DNA in the whole form were added into 293E cells (Invitrogen) for co-transfection to obtain a supernatant, which was identified by Western blot. Normal human IgG (Jacson Lab) was used as a control group.

As a result, as shown in FIG. 12, it was confirmed that four clone phages were successfully converted into whole IgG form compared to a control group.

Figure 14:
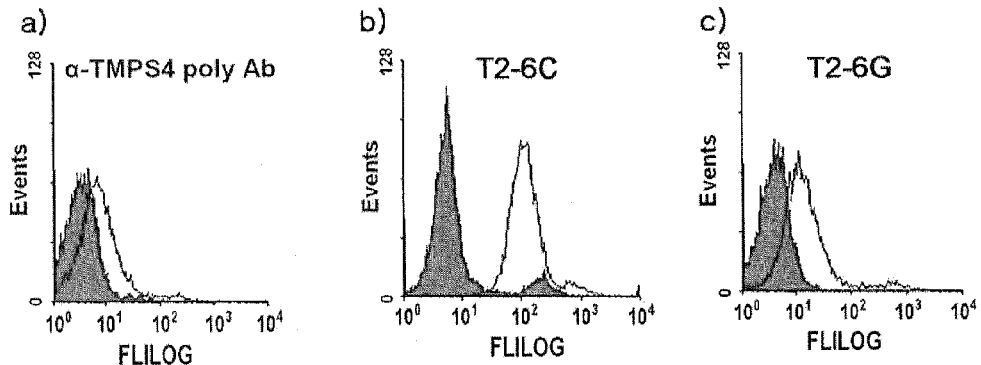
FIG. 14 is a group of graphs illustrating results, confirming that TMPRSS4 polyclonal antibody and purified monoclonal antibodies T2-6C and T2-6G specifically bind to colorectal cancer cell lines: a: polyclonal antibody; b: monoclonal antibody T2-6C; and c: monoclonal antibody T2-6G.

Protein A-affinity chromatography column (Pharmacia, GE, USA) was used to purify T2-6C and T2-6G whole form IgGs among the four clone phages (FIG. 13), and then binding capacities to TMPRSS4 were identified by FACS by the same manner as in Example 6-2 (FIG. 14).

Example 7

Figure 15:
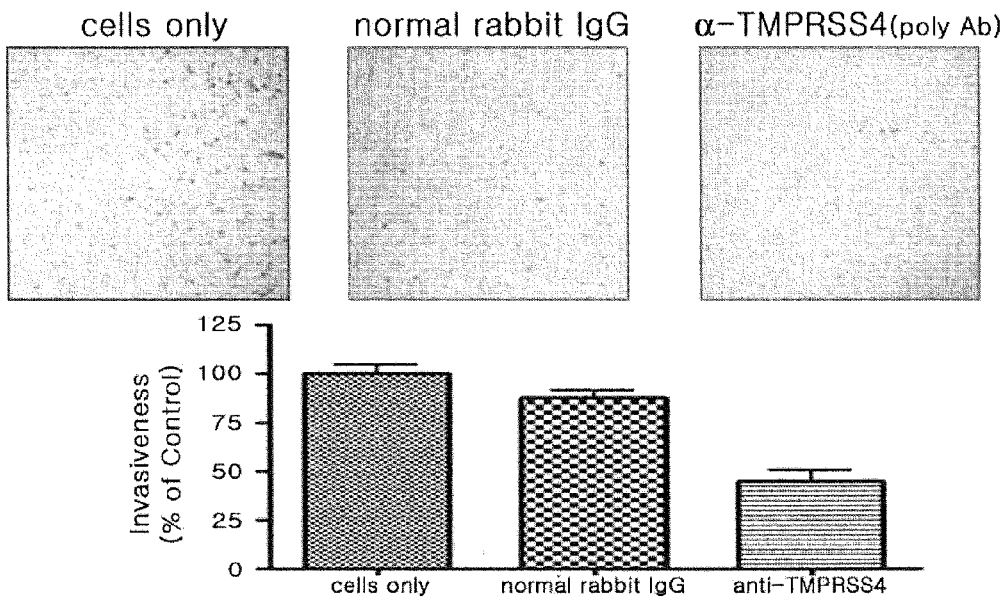
FIG. 15 is a group of photos and a graph illustrating results, confirming that TMPRSS4 polyclonal antibodies inhibit the invasion of colorectal cancer cell line Colo205.

Study on Effects of TMPRSS4 Human Antibodies on Invasion and Migration of Colorectal Cell Line <7-1> Analysis of Colo205 Cell Invasion Colo205 cells were collected with trypsin (Gibco 25300), washed twice with RPMI invasion medium supplemented with 10 mM HEPES and 0.5% BSA, and suspended at a concentration of $2\times10^6$/mL in the invasion medium. Each of purified TMPRSS4 polyclonal antibody and monoclonal T2-6C antibody was diluted at 30 ng/50 mL and 75 ng/50 ml, respectively with the invasion media. Then, 50 μl of the cell suspension and 50 ul of TMPRSS4 antibody solution were mixed, followed by pre-incubation at 37° C. for 2 hours. A 24-well transwell plate (8 μm pore size, costar 3422) was coated on the upper side of an insert at room temperature for 1 hour using a solution produced by dilution of matrigel (BD 354234) in 1 mg/ml of serum-free medium (RPMI, 10 mM HEPES). After 1 hour, matrigel in the insert was removed and the insert was washed with serum-free medium. Subsequently, 600 μl of RPMI invasion medium supplemented with 5% FBS was placed into a chamber. Sterilized forceps were used to place the insert into a chamber including the medium. 100 μl of a mixture containing pre-reacted cells and antibodies was introduced into the insert and incubated in 37° C./5% $CO_2$ for 24 hours. In order to measure cells invading through the matrigel, the upper side of the insert was cleaned with a swab dipped in PBS and the insert was placed into a chamber including 500 µL of 3.7% paraformaldehyde (Sigma HT50), followed by immobilization at room temperature for 30 minutes. Subsequently, the insert was stained with 500 µl of 1% crystal violet (Sigma C3886)/100 mM NaBorate (Sigma S9640), washed with water, and dried to count cells with a microscope of magnification×100. As a result, as shown in FIGS. 15, 16, and 17, it was observed that purified polyclonal and TMPRSS4 monoclonal antibodies (T2-6C and T2-6G) significantly inhibited invasion in Colo205, a colorectal cancer cell line by 50% or more than rabbit (FIG. 15) and human normal IGg (FIGS. 16 and 17) antibodies.

<7-2> Analysis of Colo205 Cell Migration

Colo205 and Sw480 (ATCC, CCL-228) cell lines known to overexpress and underexpress TMPRSS4, respectively were collected with trypsin, washed twice with RPMI migration medium supplemented with 10 mM HEPES and 0.5% BSA, and suspended at a concentration of $8 \times 10^5$ ml in the medium. 50 µl of the cell suspension and 50 ul of each of polyclonal TMPRSS4 antibody solutions diluted at three different concentrations (0, 1, and 2 µM) and monoclonal T2-6C and T2-6G antibodies (TMPRSS4 antibodies were diluted at 1000 ng/50 µl with migration medium) were each mixed, followed by pre-incubation at 37° C. for 2 hours. A 24-well transwell plate was coated on the lower side of an insert at room temperature for 1 hour using 0.05% gelatin (Sigma G1393). After 1 hour, matrigel in the insert was removed and the insert was washed with PBS. On completion of the process, 600 µL of RPMI migration medium supplemented with 5% FBS was placed into a chamber. Sterilized forceps were used to place the insert into a chamber. 100 ul of a mixture containing pre-reacted cells and antibodies was introduced into the insert and incubated in 37° C./5% $CO_2$ for 24 hours. In order to measure the migration of cells, the upper side of the insert was cleaned with a swab dipped in PBS and the insert was placed into a chamber including 500 ul of 3.7% paraformaldehyde (Sigma HT50), followed by immobilization at room temperature for 30 minutes. Subsequently, the insert was stained with 500 ul of 1% crystal violet/100 mM NaBorate, washed with water, and dried to count cells with a microscope of magnification×100. As a result, as shown in 18, it was confirmed that the two colorectal cancer cell lines make a significant difference in migration, and that the migration caused by TMPRSS4 as a target antigen was inhibited by TMPRSS4-specific polyclonal antibodies. It was observed that purified monoclonal T2-6C (FIG. 19) and T2-6G (FIG. 20) antibodies as well as polyclonal antibodies against TMPRSS4 significantly inhibited invasion in Colo205, an overexpressed colorectal cancer cell line by 50% or more, respectively than human normal IGg.

<7-3> Analysis of Colo205 Proliferation

Colo205 cells were collected with trypsin, washed twice with RPMI medium supplemented with 2% FBS, and suspended at a concentration of $2 \times 10^5$/ml in serum-free medium (RPMI, 10 mM HEPES). Purified TMPRSS4 antibodies diluted at 250, 500, and 1000 ng/40 ul, respectively in serum-free medium, 50 ul of the cell suspension, and 50 µl of TMPRSS4 T2-6C antibody solution were mixed, followed by pre-incubation at 37° C. for 2 hours. 10 ul of FBS was added into 90 ul of a mixture containing cells after the reaction and antibodies and introduced into a 96-well plate (100 µl/well). Incubations were performed in 37° C./5% $CO_2$ for 24, 48, 72 hours, respectively. Each of 10 µl of PreMix WST-I cell proliferation solution (takara, MK400) was added into well at each time point, followed by reaction at 37° C. for 2 hours. The optical density of each sample was measured at 440 nm on a VERSA max microplate reader.

As a result, it was confirmed that the purified TMPRSS4 T2-6C antibodies induced a significant inhibition of Colo205 cell proliferation (data not shown).

Example 8

Measurement of Binding Capacity

Binding capacities of antibodies against TMPRSS4 antigens were measured by ELISA and analyzed by GraphPad PRISM 4.0 program. As a result, it was confirmed that the binding constant value $K_D$ was measured at about $1.03 \times 10^{-9}$ M.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A TMPRSS4-specific human antibody selected from the group consisting of
   a. an antibody comprising a heavy chain comprising a heavy chain variable region ($V_H$) comprising a heavy chain complementarity determining region (HCDR) 1 having an amino acid sequence of SEQ ID No. 7, HCDR 2 having an amino acid sequence of SEQ ID No. 19, and HCDR 3 having an amino acid sequence of SEQ ID No. 32; and a light chain comprising a light chain variable region ($V_L$) comprising a light chain complementarity determining region (LCDR) 1 having an amino acid sequence of SEQ ID No. 58, LCDR 2 having an amino acid sequence of SEQ ID No. 71, and LCDR 3 having an amino acid sequence of SEQ ID No. 84;
   b. an antibody comprising a heavy chain comprising a heavy chain variable region ($V_H$) comprising a heavy chain complementarity determining region (HCDR) 1 having an amino acid sequence of SEQ ID No. 8, HCDR 2 having an amino acid sequence of SEQ ID No. 20, and HCDR 3 having an amino acid sequence of SEQ ID No. 33; and a light chain comprising a light chain variable region ($V_L$) comprising a light chain complementarity determining region (LCDR) 1 having an amino acid sequence of SEQ ID No. 59, LCDR 2 having an amino acid sequence of SEQ ID No. 72, and LCDR 3 having an amino acid sequence of SEQ ID No. 85;
   c. an antibody comprising a heavy chain comprising a heavy chain variable region ($V_H$) comprising a heavy chain complementarity determining region (HCDR) 1 having an amino acid sequence of SEQ ID No. 9, HCDR 2 having an amino acid sequence of SEQ ID No. 21, and HCDR 3 having an amino acid sequence of SEQ ID No. 34; and a light chain comprising a light chain variable region ($V_L$) comprising a light chain complementarity determining region (LCDR) 1 having an amino acid sequence of SEQ ID No. 60, LCDR 2 having an amino acid sequence of SEQ ID No. 77, and LCDR 3 having an amino acid sequence of SEQ ID No. 86;
   d. an antibody comprising a heavy chain comprising a heavy chain variable region ($V_H$) comprising a heavy chain complementarity determining region (HCDR) 1 having an amino acid sequence of SEQ ID No. 10, HCDR 2 having an amino acid sequence of SEQ ID No. 22, and HCDR 3 having an amino acid sequence of SEQ ID No. 35; and a light chain comprising a light chain variable region ($V_L$) comprising a light chain complementarity determining region (LCDR) 1 having an amino acid sequence of SEQ ID No. 64, LCDR 2 having an amino acid sequence of SEQ ID No. 74, and LCDR 3 having an amino acid sequence of SEQ ID No. 87;
   e. an antibody comprising a heavy chain comprising a heavy chain variable region ($V_H$) comprising a heavy chain complementarity determining region (HCDR) 1 having an amino acid sequence of SEQ ID No. 11, HCDR 2 having an amino acid sequence of SEQ ID No. 23, and HCDR 3 having an amino acid sequence of SEQ ID No. 36; and a light chain comprising a light chain variable region ($V_L$) comprising a light chain complementarity determining region (LCDR) 1 having an amino acid sequence of SEQ ID No. 62, LCDR 2 having an amino acid sequence of SEQ ID No. 75, and LCDR 3 having an amino acid sequence of SEQ ID No. 88;
   f. an antibody comprising a heavy chain comprising a heavy chain variable region ($V_H$) comprising a heavy chain complementarity determining region (HCDR) 1 having an amino acid sequence of SEQ ID No. 12, HCDR 2 having an amino acid sequence of SEQ ID No. 24, and HCDR 3 having an amino acid sequence of SEQ ID No. 37; and a light chain comprising a light chain variable region (V_L) comprising a light chain complementarity determining region (LCDR) 1 having an amino acid sequence of SEQ ID No. 63, LCDR 2 having an amino acid sequence of SEQ ID No. 76, and LCDR 3 having an amino acid sequence of SEQ ID No. 89;

g. an antibody comprising a heavy chain comprising a heavy chain variable region (V_H) comprising a heavy chain complementarity determining region (HCDR) 1 having an amino acid sequence of SEQ ID No. 13, HCDR 2 having an amino acid sequence of SEQ ID No. 25, and HCDR 3 having an amino acid sequence of SEQ ID No. 38; and a light chain comprising a light chain variable region (V_L) comprising a light chain complementarity determining region (LCDR) 1 having an amino acid sequence of SEQ ID No. 64, LCDR 2 having an amino acid sequence of SEQ ID No. 77, and LCDR 3 having an amino acid sequence of SEQ ID No. 90;

h. an antibody comprising a heavy chain comprising a heavy chain variable region (V_H) comprising a heavy chain complementarity determining region (HCDR) 1 having an amino acid sequence of SEQ ID No. 8, HCDR 2 having an amino acid sequence of SEQ ID No. 26, and HCDR 3 having an amino acid sequence of SEQ ID No. 39; and a light chain comprising a light chain variable region (V_L) comprising a light chain complementarity determining region (LCDR) 1 having an amino acid sequence of SEQ ID No. 65, LCDR 2 having an amino acid sequence of SEQ ID No. 78, and LCDR 3 having an amino acid sequence of SEQ ID No. 91;

i. an antibody comprising a heavy chain comprising a heavy chain variable region (V_H) comprising a heavy chain complementarity determining region (HCDR) 1 having an amino acid sequence of SEQ ID No. 14, HCDR 2 having an amino acid sequence of SEQ ID No. 27, and HCDR 3 having an amino acid sequence of SEQ ID No. 40; and a light chain comprising a light chain variable region (V_L) comprising a light chain complementarity determining region (LCDR) 1 having an amino acid sequence of SEQ ID No. 66, LCDR 2 having an amino acid sequence of SEQ ID No. 79, and LCDR 3 having an amino acid sequence of SEQ ID No. 92;

j. an antibody comprising a heavy chain comprising a heavy chain variable region (V_H) comprising a heavy chain complementarity determining region (HCDR) 1 having an amino acid sequence of SEQ ID No. 15, HCDR 2 having an amino acid sequence of SEQ ID No. 28, and HCDR 3 having an amino acid sequence of SEQ ID No. 41; and a light chain comprising a light chain variable region (V_L) comprising a light chain complementarity determining region (LCDR) 1 having an amino acid sequence of SEQ ID No. 67, LCDR 2 having an amino acid sequence of SEQ ID No. 80, and LCDR 3 having an amino acid sequence of SEQ ID No. 93;

k. an antibody comprising a heavy chain comprising a heavy chain variable region (V_H) comprising a heavy chain complementarity determining region (HCDR) 1 having an amino acid sequence of SEQ ID No. 16, HCDR 2 having an amino acid sequence of SEQ ID No. 29, and HCDR 3 having an amino acid sequence of SEQ ID No. 42; and a light chain comprising a light chain variable region (V_L) comprising a light chain complementarity determining region (LCDR) 1 having an amino acid sequence of SEQ ID No. 68, LCDR 2 having an amino acid sequence of SEQ ID No. 81, and LCDR 3 having an amino acid sequence of SEQ ID No. 94;

l. an antibody comprising a heavy chain comprising a heavy chain variable region (V_H) comprising a heavy chain complementarity determining region (HCDR) 1 having an amino acid sequence of SEQ ID No. 17, HCDR 2 having an amino acid sequence of SEQ ID No. 30, and HCDR 3 having an amino acid sequence of SEQ ID No. 43; and a light chain comprising a light chain variable region (V_L) comprising a light chain complementarity determining region (LCDR) 1 having an amino acid sequence of SEQ ID No. 69, LCDR 2 having an amino acid sequence of SEQ ID No. 82, and LCDR 3 having an amino acid sequence of SEQ ID No. 95; and m. an antibody comprising a heavy chain comprising a heavy chain variable region (V_H) comprising a heavy chain complementarity determining region (HCDR) 1 having an amino acid sequence of SEQ ID No. 18, HCDR 2 having an amino acid sequence of SEQ ID No. 31, and HCDR 3 having an amino acid sequence of SEQ ID No. 44; and a light chain comprising a light chain variable region (V_L) comprising a light chain complementarity determining region (LCDR) 1 having an amino acid sequence of SEQ ID No. 70, LCDR 2 having an amino acid sequence of SEQ ID No. 83, and LCDR 3 having an amino acid sequence of SEQ ID No. 96.

2. The human antibody as set forth in claim 1, wherein the heavy chain variable region is selected from the group consisting of the heavy chain variable region of (a) having amino acid sequence of SEQ ID No. 45;
the heavy chain variable region of (b) having amino acid sequence of SEQ ID No. 46;
the heavy chain variable region of (c) having amino acid sequence of SEQ ID No. 47;
the heavy chain variable region of (d) having amino acid sequence of SEQ ID No. 48;
the heavy chain variable region of (e) having amino acid sequence of SEQ ID No. 49;
the heavy chain variable region of (f) having amino acid sequence of SEQ ID No. 50;
the heavy chain variable region of (g) having amino acid sequence of SEQ ID No. 51;
the heavy chain variable region of (h) having amino acid sequence of SEQ ID No. 52;
the heavy chain variable region of (i) having amino acid sequence of SEQ ID No. 53;
the heavy chain variable region of (j) having amino acid sequence of SEQ ID No. 54;
the heavy chain variable region of (k) having amino acid sequence of SEQ ID No. 55;
the heavy chain variable region of (l) having amino acid sequence of SEQ ID No. 56; and
the heavy chain variable region of (m) having amino acid sequence of SEQ ID No. 57.

3. The human antibody as set forth in claim 1, wherein the light chain variable region is selected from the group consisting of the light chain variable region of (a) having amino acid sequence of SEQ ID No. 97;
the light chain variable region of (b) having amino acid sequence of SEQ ID No. 98;
the light chain variable region of (c) having amino acid sequence of SEQ ID No. 99;
the light chain variable region of (d) having amino acid sequence of SEQ ID No. 100;
the light chain variable region of (e) having amino acid sequence of SEQ ID No. 101;
the light chain variable region of (f) having amino acid sequence of SEQ ID No. 102;

the light chain variable region of (g) having amino acid sequence of SEQ ID No. 103;
the light chain variable region of (h) having amino acid sequence of SEQ ID No. 104;
the light chain variable region of (i) having amino acid sequence of SEQ ID No. 105;
the light chain variable region of (j) having amino acid sequence of SEQ ID No. 106;
the light chain variable region of (k) having amino acid sequence of SEQ ID No. 107;
the light chain variable region of (l) having amino acid sequence of SEQ ID No. 108; and
the light chain variable region of (m) having amino acid sequence of SEQ ID No. 109.

4. An in vitro method for inhibiting invasion, migration or proliferation of a TMPRSS4-overexpressed cancer cell comprising treating the TMPRSS4-overexpressed cancer cell with an effective amount of the human antibody of claim 1.

5. The in vitro method as set forth in claim 4, wherein the TMPRSS4-overexpressed cancer cell is a cell selected from the group consisting of colorectal cancer cell, lung cancer cell, liver cancer cell, pancreatic cancer cell, gastric cancer cell, and malignant thyroid neoplasms cell.

6. A composition comprising the human antibody of claim 1, and a radioactive isotope for in vitro radioimmuno treatment or detection of a TMPRSS4-overexpressed cancer.

7. The composition as set forth in claim 6, wherein the TMPRSS4-overexpressed cancer is selected from the group consisting of colorectal cancer, lung cancer, liver cancer, pancreatic cancer, gastric cancer, and malignant thyroid neoplasms.

8. The composition as set forth in claim 6, wherein the radioactive isotope is selected from the group consisting of $^{3}H$, $^{11}C$, $^{14}C$, $C^{18}F$, $^{64}Cu$, $^{76}Br$, $^{86}Y$, $^{99m}Tc$, $^{111}In$, $^{123}I$, $^{177}Lu$, and a mixture or combination thereof.

9. The composition as set forth in claim 6, wherein the radioactive isotope is bound to a human antibody or included in a carrier to which the human antibody is bound.

10. An in vitro method for imaging TMPRSS4-overexpressed cancer, the method comprising:
   1) treating a sample from a subject with a diagnostically effective amount of the composition of claim 6; and
   2) obtaining a detection image for the subject.

11. The in vitro method as set forth in claim 10, wherein the TMPRSS4-overexpressed cancer is selected from the group consisting of colorectal cancer, lung cancer, liver cancer, pancreatic cancer, gastric cancer, and malignant thyroid neoplasms.

12. An in vitro method for prognostic evaluation of a cancer patient, the method comprising:
   1) treating a sample from a patient whose tumor has been eliminated with the composition of claim 6;
   2) detecting the composition of Step 1) to identify tumor cells; and
   3) judging that all tumor cells have been eliminated when tumor cells are not detected in step 2).

* * * * *

SEQUENCE LISTING

```
<160> NUMBER OF SEQ ID NOS: 121

<210> SEQ ID NO 1
<211> LENGTH: 75
<212> TYPE: DNA
<213> ORGANISM: Artificial Sequence
<220> FEATURE:
<223> OTHER INFORMATION: TMPRSS4 forward primer

<400> SEQUENCE: 1
gaggagcata tggattataa agatcatgat attgattata aagatgatga tgataaagtg      60
gtgggtgggg aggag                                                      75

<210> SEQ ID NO 2
<211> LENGTH: 30
<212> TYPE: DNA
<213> ORGANISM: Artificial Sequence
<220> FEATURE:
<223> OTHER INFORMATION: TMPRSS4 reverse primer
```

```
<400> SEQUENCE: 2
gaggagctcg agcagctcag ccttccagac                                30

<210> SEQ ID NO 3
<211> LENGTH: 18
<212> TYPE: DNA
<213> ORGANISM: Artificial Sequence
<220> FEATURE:
<223> OTHER INFORMATION: CMV-proF primer

<400> SEQUENCE: 3
aaatgggcgg taggcgtg                                             18

<210> SEQ ID NO 4
<211> LENGTH: 30
<212> TYPE: DNA
<213> ORGANISM: Artificial Sequence
<220> FEATURE:
<223> OTHER INFORMATION: NATJK-R4

<400> SEQUENCE: 4
gaggagagat cttttgattt ccaccttggt                                30

<210> SEQ ID NO 5
<211> LENGTH: 23
<212> TYPE: DNA
<213> ORGANISM: Artificial Sequence
<220> FEATURE:
<223> OTHER INFORMATION: pelB5

<400> SEQUENCE: 5
ctagataacg agggcaaatc atg                                       23

<210> SEQ ID NO 6
<211> LENGTH: 19
<212> TYPE: DNA
<213> ORGANISM: Artificial Sequence
<220> FEATURE:
<223> OTHER INFORMATION: cla3

<400> SEQUENCE: 6
cgtcaccaat gaaaccatc                                            19

<210> SEQ ID NO 7
<211> LENGTH: 5
<212> TYPE: PRT
<213> ORGANISM: Artificial Sequence
<220> FEATURE:
<223> OTHER INFORMATION: T1-11G VH CDR 1

<400> SEQUENCE: 7

Arg Tyr Thr Met His
1               5

<210> SEQ ID NO 8
<211> LENGTH: 5
<212> TYPE: PRT
<213> ORGANISM: Artificial Sequence
<220> FEATURE:
<223> OTHER INFORMATION: T1-12C VH CDR 1

<400> SEQUENCE: 8

Asn Tyr Gly Met His
1               5
```

<210> SEQ ID NO 9
<211> LENGTH: 5
<212> TYPE: PRT
<213> ORGANISM: Artificial Sequence
<220> FEATURE:
<223> OTHER INFORMATION: T1-9F VH CDR 1

<400> SEQUENCE: 9

Ser Tyr Ala Met Ser
1               5

<210> SEQ ID NO 10
<211> LENGTH: 5
<212> TYPE: PRT
<213> ORGANISM: Artificial Sequence
<220> FEATURE:
<223> OTHER INFORMATION: T2-8F VH CDR 1

<400> SEQUENCE: 10

Asn Tyr Ala Met Asn
1               5

<210> SEQ ID NO 11
<211> LENGTH: 5
<212> TYPE: PRT
<213> ORGANISM: Artificial Sequence
<220> FEATURE:
<223> OTHER INFORMATION: T2-12C VH CDR 1

<400> SEQUENCE: 11

Arg Tyr Gly Ile His
1               5

<210> SEQ ID NO 12
<211> LENGTH: 5
<212> TYPE: PRT
<213> ORGANISM: Artificial Sequence
<220> FEATURE:
<223> OTHER INFORMATION: T2-3A VH CDR 1

<400> SEQUENCE: 12

Ser Tyr Ala Met His
1               5

<210> SEQ ID NO 13
<211> LENGTH: 6
<212> TYPE: PRT
<213> ORGANISM: Artificial Sequence
<220> FEATURE:
<223> OTHER INFORMATION: T2-7B VH CDR 1

<400> SEQUENCE: 13

Asp Ser Val Ala Trp Asn
1               5

<210> SEQ ID NO 14
<211> LENGTH: 5
<212> TYPE: PRT
<213> ORGANISM: Artificial Sequence
<220> FEATURE:
<223> OTHER INFORMATION: T2-10E VH CDR 1

<400> SEQUENCE: 14

Asp Tyr Ala Met His
1               5

```
<210> SEQ ID NO 15
<211> LENGTH: 5
<212> TYPE: PRT
<213> ORGANISM: Artificial Sequence
<220> FEATURE:
<223> OTHER INFORMATION: T2-6C VH CDR 1

<400> SEQUENCE: 15

Asp Tyr Ala Ile His
1               5

<210> SEQ ID NO 16
<211> LENGTH: 5
<212> TYPE: PRT
<213> ORGANISM: Artificial Sequence
<220> FEATURE:
<223> OTHER INFORMATION: T1-5G VH CDR 1

<400> SEQUENCE: 16

Asp His Tyr Met Ser
1               5

<210> SEQ ID NO 17
<211> LENGTH: 5
<212> TYPE: PRT
<213> ORGANISM: Artificial Sequence
<220> FEATURE:
<223> OTHER INFORMATION: T2-6A VH CDR 1

<400> SEQUENCE: 17

Ser Tyr Asp Val His
1               5

<210> SEQ ID NO 18
<211> LENGTH: 5
<212> TYPE: PRT
<213> ORGANISM: Artificial Sequence
<220> FEATURE:
<223> OTHER INFORMATION: T2-12A VH CDR 1

<400> SEQUENCE: 18

Asn Tyr Ala Met Ser
1               5

<210> SEQ ID NO 19
<211> LENGTH: 17
<212> TYPE: PRT
<213> ORGANISM: Artificial Sequence
<220> FEATURE:
<223> OTHER INFORMATION: T1-11G VH CDR 2

<400> SEQUENCE: 19

Val Ile Ser Ser Asp Gly Ser Lys Lys Tyr Tyr Gly Asp Ser Val Lys
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: T1-12C VH CDR 2

<400> SEQUENCE: 20

Val Ile Ser Tyr Asp Gly Ser Thr Lys Tyr Tyr Ala Asp Ser Val Arg
1               5                   10                  15
```

Gly

<210> SEQ ID NO 21
<211> LENGTH: 17
<212> TYPE: PRT
<213> ORGANISM: Artificial Sequence
<220> FEATURE:
<223> OTHER INFORMATION: T1-9F VH CDR 2

<400> SEQUENCE: 21

Ala Ile Thr Gly Ser Gly Gly Ser Thr Phe Tyr Ala Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: T2-8F VH CDR 2

<400> SEQUENCE: 22

Ala Ile Ser Gly Ser Gly Gly Ser Thr Tyr Tyr Ala Asp Ser Val Lys
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: T2-12C VH CDR 2

<400> SEQUENCE: 23

Val Ile Ser Tyr Asp Gly Asn Ile Lys Tyr Tyr Ala Asp Ser Val Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: T2-3A VH CDR 2

<400> SEQUENCE: 24

Ser Ile Ser Trp Ser Ser Asn Asn Ile Arg Tyr Ala Asp Ser Val Lys
1               5                   10                  15

Gly

<210> SEQ ID NO 25
<211> LENGTH: 18
<212> TYPE: PRT
<213> ORGANISM: Artificial Sequence
<220> FEATURE:
<223> OTHER INFORMATION: T2-7B VH CDR 2

<400> SEQUENCE: 25

Arg Thr Tyr Tyr Lys Ser Lys Trp Tyr Asn Asp Tyr Ala Val Ser Val
1               5                   10                  15

Arg Ser

<210> SEQ ID NO 26

```
<211> LENGTH: 17
<212> TYPE: PRT
<213> ORGANISM: Artificial Sequence
<220> FEATURE:
<223> OTHER INFORMATION: T2-6G VH CDR 2

<400> SEQUENCE: 26

Val Ile Ser Tyr Asp Gly Ser Lys Lys Tyr Tyr Ala Asp Ser Val Lys
 1               5                  10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: T2-10E VH CDR 2

<400> SEQUENCE: 27

Gly Ile Ser Trp Asn Ser Gly Ser Ile Gly Tyr Ala Asp Ser Val Lys
 1               5                  10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: T2-6C VH CDR 2

<400> SEQUENCE: 28

Gly Ile Ser Trp Asn Ser Glu Ile Val Gly Tyr Gly Asp Ser Val Lys
 1               5                  10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: T1-5G VH CDR 2

<400> SEQUENCE: 29

Tyr Ile Ser Asn Arg Gly Tyr Ser Ile Tyr Tyr Ala Asp Ser Val Lys
 1               5                  10                  15

Asp

<210> SEQ ID NO 30
<211> LENGTH: 17
<212> TYPE: PRT
<213> ORGANISM: Artificial Sequence
<220> FEATURE:
<223> OTHER INFORMATION: T2-6A VH CDR 2

<400> SEQUENCE: 30

Trp Val Asn Pro Asn Ser Gly Asn Ala Asp Tyr Ala Gln Lys Phe Gln
 1               5                  10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: T2-12A VH CDR 2
```

```
<400> SEQUENCE: 31

Ala Ile Ser Gly Ser Gly Ala Ser Thr Asn Tyr Ala Asp Ser Val Lys
1               5                   10                  15
Gly

<210> SEQ ID NO 32
<211> LENGTH: 10
<212> TYPE: PRT
<213> ORGANISM: Artificial Sequence
<220> FEATURE:
<223> OTHER INFORMATION: T1-11G VH CDR 3

<400> SEQUENCE: 32

Gly Gly Gly Lys Gly His Trp Leu Asp Thr
1               5                   10

<210> SEQ ID NO 33
<211> LENGTH: 6
<212> TYPE: PRT
<213> ORGANISM: Artificial Sequence
<220> FEATURE:
<223> OTHER INFORMATION: T1-12C VH CDR 3

<400> SEQUENCE: 33

Gly Ser Asp Val Ala Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: T1-9F VH CDR 3

<400> SEQUENCE: 34

Gly Gly Asn Leu Asp Val
1               5

<210> SEQ ID NO 35
<211> LENGTH: 7
<212> TYPE: PRT
<213> ORGANISM: Artificial Sequence
<220> FEATURE:
<223> OTHER INFORMATION: T2-8F VH CDR 3

<400> SEQUENCE: 35

Leu Arg Gly Ala Phe Asp Ile
1               5

<210> SEQ ID NO 36
<211> LENGTH: 12
<212> TYPE: PRT
<213> ORGANISM: Artificial Sequence
<220> FEATURE:
<223> OTHER INFORMATION: T2-12C VH CDR 3

<400> SEQUENCE: 36

Leu Trp Arg Gln Ser Ala Ala Asp Ala Phe Asp Ile
1               5                   10

<210> SEQ ID NO 37
<211> LENGTH: 9
<212> TYPE: PRT
<213> ORGANISM: Artificial Sequence
<220> FEATURE:
<223> OTHER INFORMATION: T2-3A VH CDR 3
```

```
<400> SEQUENCE: 37

Arg Ala Ala Ala Lys Ala Phe Asp Ile
1               5

<210> SEQ ID NO 38
<211> LENGTH: 8
<212> TYPE: PRT
<213> ORGANISM: Artificial Sequence
<220> FEATURE:
<223> OTHER INFORMATION: T2-7B VH CDR 3

<400> SEQUENCE: 38

Gly Gly Gly Lys Gly Met Asp Val
1               5

<210> SEQ ID NO 39
<211> LENGTH: 6
<212> TYPE: PRT
<213> ORGANISM: Artificial Sequence
<220> FEATURE:
<223> OTHER INFORMATION: T2-6G VH CDR 3

<400> SEQUENCE: 39

Gly Thr Thr Met Asp Val
1               5

<210> SEQ ID NO 40
<211> LENGTH: 16
<212> TYPE: PRT
<213> ORGANISM: Artificial Sequence
<220> FEATURE:
<223> OTHER INFORMATION: T2-10E VH CDR 3

<400> SEQUENCE: 40

Gly Leu Arg Gly Leu Arg Tyr Arg Asn Tyr Tyr Tyr Gly Met Asp Val
1               5                   10                  15

<210> SEQ ID NO 41
<211> LENGTH: 9
<212> TYPE: PRT
<213> ORGANISM: Artificial Sequence
<220> FEATURE:
<223> OTHER INFORMATION: T2-6C VH CDR 3

<400> SEQUENCE: 41

Gly Ser Ser Gly Arg Ala Phe Asp Ile
1               5

<210> SEQ ID NO 42
<211> LENGTH: 18
<212> TYPE: PRT
<213> ORGANISM: Artificial Sequence
<220> FEATURE:
<223> OTHER INFORMATION: T1-5G VH CDR 3

<400> SEQUENCE: 42

Asp Leu Arg Ser Ser Asp Ala His Thr Trp Gly Gly Val Asp Ala Phe
1               5                   10                  15

Asp Ile

<210> SEQ ID NO 43
<211> LENGTH: 8
<212> TYPE: PRT
<213> ORGANISM: Artificial Sequence
<220> FEATURE:
<223> OTHER INFORMATION: T2-6A VH CDR 3
```

```
<400> SEQUENCE: 43

Gly Arg Phe Gly Ala Phe Asp Val
1               5

<210> SEQ ID NO 44
<211> LENGTH: 14
<212> TYPE: PRT
<213> ORGANISM: Artificial Sequence
<220> FEATURE:
<223> OTHER INFORMATION: T2-12A VH CDR 3

<400> SEQUENCE: 44

Leu Gly Arg Glu Gln Tyr Leu Ala Arg Gly Tyr Phe Glu His
1               5                   10

<210> SEQ ID NO 45
<211> LENGTH: 139
<212> TYPE: PRT
<213> ORGANISM: Artificial Sequence
<220> FEATURE:
<223> OTHER INFORMATION: T1-11G heavy chain

<400> SEQUENCE: 45

Met Ala Gln Val Gln Leu Val Gln Ser Gly Gly Val Val Gln Pro
1               5                   10                  15

Gly Arg Ser Leu Arg Leu Ser Cys Ala Ala Ser Gly Phe Thr Leu Ser
            20                  25                  30

Arg Tyr Thr Met His Trp Val Arg Gln Ala Pro Gly Lys Gly Leu Gln
            35                  40                  45

Trp Val Ala Val Ile Ser Ser Asp Gly Ser Lys Lys Tyr Tyr Gly Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Gly Gly Gly Lys Gly His Trp Leu Asp Thr Trp Gly
            100                 105                 110

Gln Gly Ser Leu Val Thr Val Ser Ser Gly Leu Gly Gly Leu Gly Gly
            115                 120                 125

Gly Gly Ser Gly Gly Gly Gly Ser Gly Gly Ser
        130                 135

<210> SEQ ID NO 46
<211> LENGTH: 137
<212> TYPE: PRT
<213> ORGANISM: Artificial Sequence
<220> FEATURE:
<223> OTHER INFORMATION: T2- 6A heavy chain

<400> SEQUENCE: 46

Met Ala Gln Met Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ser Tyr Asp Val His Trp Val Arg Gln Ala Thr Gly Gln Gly Leu Glu
            35                  40                  45

Trp Met Gly Trp Val Asn Pro Asn Ser Gly Asn Ala Asp Tyr Ala Gln
    50                  55                  60

Lys Phe Gln Gly Arg Val Thr Met Thr Arg Asn Ser Ser Ile Ser Thr
65                  70                  75                  80
```

Ala Tyr Met Glu Leu Ser Ser Leu Arg Ser Glu Asp Thr Ala Val Tyr
                85                  90                  95

Tyr Cys Ala Val Gly Arg Phe Gly Ala Phe Asp Val Trp Gly Gln Gly
            100                 105                 110

Ser Met Val Thr Val Ser Ser Gly Leu Gly Gly Leu Gly Gly Gly Gly
        115                 120                 125

Ser Gly Gly Gly Gly Ser Gly Gly Ser
        130                 135

<210> SEQ ID NO 47
<211> LENGTH: 135
<212> TYPE: PRT
<213> ORGANISM: Artificial Sequence
<220> FEATURE:
<223> OTHER INFORMATION: T1-12C heavy chain

<400> SEQUENCE: 47

Met Ala Gln Val Gln Leu Val Glu Ser Gly Gly Gly Val Val Gln Pro
1               5                   10                  15

Gly Arg Ser Leu Arg Leu Ser Cys Thr Ala Ser Gly Phe Thr Phe Arg
            20                  25                  30

Asn Tyr Gly Met His Trp Val Arg Gln Ala Pro Gly Lys Gly Leu Glu
        35                  40                  45

Trp Val Ala Val Ile Ser Tyr Asp Gly Ser Thr Lys Tyr Tyr Ala Asp
    50                  55                  60

Ser Val Arg Gly Arg Phe Thr Ile Ser Arg Asp Asn Ser Lys Asn Thr
65                  70                  75                  80

Leu Tyr Leu Gln Met Asn Ser Leu Arg Ser Glu Asp Thr Ala Val Tyr
                85                  90                  95

Tyr Cys Ala Arg Gly Ser Asp Val Ala Tyr Trp Gly Gln Gly Thr Leu
            100                 105                 110

Val Thr Val Ser Ser Gly Leu Gly Gly Leu Gly Gly Gly Gly Ser Gly
        115                 120                 125

Gly Gly Gly Ser Gly Gly Ser
        130                 135

<210> SEQ ID NO 48
<211> LENGTH: 135
<212> TYPE: PRT
<213> ORGANISM: Artificial Sequence
<220> FEATURE:
<223> OTHER INFORMATION: T1- 9F heavy chain

<400> SEQUENCE: 48

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Thr Gly Ser Gly Gly Ser Thr Phe Tyr Ala Asp
    50                  55                  60

Ser Val Lys Gly Arg Phe Thr Ile Ser Arg Asp Asn Ser Lys Asn Met
65                  70                  75                  80

Leu Tyr Leu Gln Met Asn Ser Leu Arg Ala Glu Asp Thr Ala Val Tyr
                85                  90                  95

Tyr Cys Ala Arg Gly Gly Asn Leu Asp Val Trp Gly Leu Gly Thr Thr
            100                 105                 110

```
Val Thr Val Ser Ser Gly Leu Gly Gly Leu Gly Gly Gly Ser Gly
        115                 120                 125
Gly Gly Gly Ser Gly Gly Ser
        130             135

<210> SEQ ID NO 49
<211> LENGTH: 135
<212> TYPE: PRT
<213> ORGANISM: Artificial Sequence
<220> FEATURE:
<223> OTHER INFORMATION: T2-12F heavy chain

<400> SEQUENCE: 49

Met Ala Gln Val Gln Leu Val Glu Ser Gly Gly Gly Leu Val Gln Pro
1               5                   10                  15
Gly Gly Ser Leu Arg Leu Ser Cys Ala Ala Ser Gly Phe Thr Phe Ser
            20                  25                  30
Ser Tyr Ala Met Ser Trp Val Arg Gln Ala Pro Gly Lys Gly Leu Glu
        35                  40                  45
Trp Val Ser Ala Ile Thr Gly Ser Gly Gly Ser Thr Phe Tyr Ala Asp
    50                  55                  60
Ser Val Lys Gly Arg Phe Thr Ile Ser Arg Asp Asn Ser Lys Asn Met
65                  70                  75                  80
Leu Tyr Leu Gln Met Asn Ser Leu Arg Ala Glu Asp Thr Ala Val Tyr
                85                  90                  95
Tyr Cys Ala Arg Gly Gly Asn Leu Asp Val Trp Gly Leu Gly Thr Thr
            100                 105                 110
Val Thr Val Ser Ser Gly Leu Gly Gly Leu Gly Gly Gly Ser Gly
        115                 120                 125
Gly Gly Gly Ser Gly Gly Ser
        130             135

<210> SEQ ID NO 50
<211> LENGTH: 136
<212> TYPE: PRT
<213> ORGANISM: Artificial Sequence
<220> FEATURE:
<223> OTHER INFORMATION: T2- 8F heavy chain

<400> SEQUENCE: 50

Met Ala Gln Val Gln Leu Val Glu Ser Gly Gly Gly Leu Val Gln Pro
1               5                   10                  15
Gly Gly Ser Leu Arg Leu Ser Cys Ala Ala Ser Gly Phe Thr Phe Arg
            20                  25                  30
Asn Tyr Ala Met Asn Trp Val Arg Gln Ala Pro Gly Lys Gly Leu Glu
        35                  40                  45
Trp Val Ser Ala Ile Ser Gly Ser Gly Gly Ser Thr Tyr Tyr Ala Asp
    50                  55                  60
Ser Val Lys Gly Arg Phe Thr Ile Ser Arg Asp Asn Ala Lys Gly Thr
65                  70                  75                  80
Leu Tyr Leu Gln Met Asn Ser Leu Arg Ala Glu Asp Thr Ala Val Tyr
                85                  90                  95
Tyr Cys Ala Arg Leu Arg Gly Ala Phe Asp Ile Trp Gly Gln Gly Thr
            100                 105                 110
Met Ile Thr Val Ser Ser Gly Leu Gly Gly Leu Gly Gly Gly Ser
        115                 120                 125
Gly Gly Gly Gly Ser Gly Gly Ser
        130             135
```

<210> SEQ ID NO 51
<211> LENGTH: 143
<212> TYPE: PRT
<213> ORGANISM: Artificial Sequence
<220> FEATURE:
<223> OTHER INFORMATION: T2-12A heavy chain

<400> SEQUENCE: 51

```
Met Ala Gln Val Gln Leu Val Lys Ser Gly Gly Gly Leu Val Gln Pro
1               5                   10                  15

Gly Gly Ser Leu Arg Leu Ser Cys Ala Ala Ser Gly Val Asn Phe Asn
            20                  25                  30

Asn Tyr Ala Met Ser Trp Val Arg Gln Ala Pro Gly Lys Gly Leu Glu
        35                  40                  45

Trp Val Ser Ala Ile Ser Ser Gly Ala Ser Thr Asn Tyr Ala Asp
    50                  55                  60

Ser Val Lys Gly Arg Phe Thr Ile Ser Arg Asp Asn Ser Glu Asn Thr
65                  70                  75                  80

Leu Tyr Leu Gln Met Asn Ser Leu Arg Ala Glu Asp Thr Ala Val Tyr
            85                  90                  95

Tyr Cys Ala Val Leu Gly Arg Glu Gln Tyr Leu Ala Arg Gly Tyr Phe
        100                 105                 110

Glu His Trp Gly Arg Gly Thr Leu Val Thr Val Ser Ser Gly Leu Gly
        115                 120                 125

Gly Leu Gly Gly Gly Ser Gly Gly Gly Ser Gly Gly Ser
        130                 135                 140
```

<210> SEQ ID NO 52
<211> LENGTH: 141
<212> TYPE: PRT
<213> ORGANISM: Artificial Sequence
<220> FEATURE:
<223> OTHER INFORMATION: T2-12C heavy chain

<400> SEQUENCE: 52

```
Met Ala Gln Val Gln Leu Val Gln Ser Gly Gly Gly Val Val Gln Pro
1               5                   10                  15

Gly Arg Ser Leu Arg Leu Ser Cys Ala Ala Ser Gly Phe Thr Phe Asn
            20                  25                  30

Arg Tyr Gly Ile His Trp Val Arg Gln Ala Pro Gly Lys Gly Leu Glu
        35                  40                  45

Trp Val Thr Val Ile Ser Tyr Asp Gly Asn Ile Lys Tyr Tyr Ala Asp
    50                  55                  60

Ser Val Lys Gly Arg Phe Thr Ile Ser Arg Asp Asn Ser Lys Asn Thr
65                  70                  75                  80

Val Tyr Leu Gln Met Asn Ser Leu Arg Ser Glu Asp Thr Ala Val Tyr
            85                  90                  95

Tyr Cys Ala Arg Leu Trp Arg Gln Ser Ala Ala Asp Ala Phe Asp Ile
        100                 105                 110

Trp Gly Pro Gly Thr Met Ile Thr Val Ser Ser Gly Leu Gly Leu
        115                 120                 125

Gly Gly Gly Gly Ser Gly Gly Gly Ser Gly Gly Ser
        130                 135                 140
```

<210> SEQ ID NO 53
<211> LENGTH: 138
<212> TYPE: PRT
<213> ORGANISM: Artificial Sequence
<220> FEATURE:
<223> OTHER INFORMATION: T2- 3A heavy chain

<400> SEQUENCE: 53

Met Ala Gln Met Gln Leu Val Gln Ser Gly Gly Gly Val Val Gln Pro
1               5                   10                  15

Gly Arg Ser Leu Arg Leu Ser Cys Ala Ala Ser Gly Phe Thr Phe Ser
            20                  25                  30

Ser Tyr Ala Met His Trp Val Arg Gln Ala Pro Gly Lys Gly Leu Glu
        35                  40                  45

Trp Ile Ser Ser Ile Ser Trp Ser Ser Asn Asn Ile Arg Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ser Glu Asp Thr Ala Val Tyr
                85                  90                  95

Tyr Cys Ala Arg Arg Ala Ala Ala Lys Ala Phe Asp Ile Trp Gly Gln
            100                 105                 110

Gly Thr Arg Val Thr Val Ser Ser Gly Leu Gly Gly Leu Gly Gly Gly
        115                 120                 125

Gly Ser Gly Gly Gly Gly Ser Gly Gly Ser
    130                 135

<210> SEQ ID NO 54
<211> LENGTH: 140
<212> TYPE: PRT
<213> ORGANISM: Artificial Sequence
<220> FEATURE:
<223> OTHER INFORMATION: T2- 7B heavy chain

<400> SEQUENCE: 54

Met Ala Gln Val Gln Leu Gln Glu Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Arg Asp Ser Val Ala Trp Asn Trp Ile Arg Gln Ser Pro Ser Arg Gly
        35                  40                  45

Leu Glu Trp Leu Gly Arg Thr Tyr Tyr Lys Ser Lys Trp Tyr Asn Asp
    50                  55                  60

Tyr Ala Val Ser Val Arg Ser Arg Ile Thr Ile Asn Pro Asp Thr Ser
65                  70                  75                  80

Lys Asn Gln Phe Ser Leu Gln Leu Asn Ser Val Thr Ala Val Asp Thr
                85                  90                  95

Ala Val Tyr Tyr Cys Ser Arg Gly Gly Gly Lys Gly Met Asp Val Trp
            100                 105                 110

Gly Gln Gly Thr Ser Val Thr Val Ser Ser Gly Leu Gly Gly Leu Gly
        115                 120                 125

Gly Gly Gly Ser Gly Gly Gly Gly Ser Gly Gly Ser
    130                 135                 140

<210> SEQ ID NO 55
<211> LENGTH: 135
<212> TYPE: PRT
<213> ORGANISM: Artificial Sequence
<220> FEATURE:
<223> OTHER INFORMATION: T2- 6G heavy chain

<400> SEQUENCE: 55

Met Ala Gln Val Gln Leu Val Glu Ser Gly Gly Gly Val Val Gln Pro

```
               1               5                  10                 15
Gly Arg Ser Leu Arg Leu Ser Cys Val Gly Ser Gly Phe Thr Phe Ser
                20                   25                30

Asn Tyr Gly Met His Trp Val Arg Gln Ala Pro Gly Lys Gly Leu Gln
                35                   40                45

Trp Val Ala Val Ile Ser Tyr Asp Gly Ser Lys Lys Tyr Tyr Ala Asp
                50                   55                60

Ser Val Lys Gly Arg Phe Thr Ile Ser Arg Asp Asn Ser Lys Asn Thr
65                   70                   75                80

Leu Tyr Leu Gln Met Asn Ser Leu Arg Ser Glu Asp Thr Ala Val Tyr
                85                   90                95

Tyr Cys Ala Arg Gly Thr Thr Met Asp Val Trp Gly Lys Gly Thr Thr
                100                  105               110

Val Thr Val Ser Ser Gly Leu Gly Gly Leu Gly Gly Gly Gly Ser Gly
                115                  120               125

Gly Gly Gly Ser Gly Gly Ser
                130                  135

<210> SEQ ID NO 56
<211> LENGTH: 145
<212> TYPE: PRT
<213> ORGANISM: Artificial Sequence
<220> FEATURE:
<223> OTHER INFORMATION: T2-10E heavy chain

<400> SEQUENCE: 56

Met Ala Gln Met Gln Leu Val Gln Ser Gly Gly Gly Val Val Lys Pro
1               5                  10                 15

Gly Gly Ser Leu Arg Leu Ser Cys Gly Ala Ser Gly Phe Thr Phe Asp
                20                   25                30

Asp Tyr Ala Met His Trp Val Arg Gln Ala Pro Gly Lys Gly Leu Glu
                35                   40                45

Trp Val Ser Gly Ile Ser Trp Asn Ser Gly Ser Ile Gly Tyr Ala Asp
                50                   55                60

Ser Val Lys Gly Arg Phe Thr Ile Ser Arg Asp Asn Ser Lys Asn Ser
65                   70                   75                80

Leu Tyr Leu Gln Met Asn Ser Leu Arg Ala Glu Asp Thr Ala Val Tyr
                85                   90                95

Tyr Cys Ala Lys Gly Leu Arg Gly Leu Arg Tyr Arg Asn Tyr Tyr Tyr
                100                  105               110

Gly Met Asp Val Trp Gly Gln Gly Thr Thr Val Thr Val Ser Ser Gly
                115                  120               125

Leu Gly Gly Leu Gly Gly Gly Gly Ser Gly Gly Gly Gly Ser Gly Gly
                130                  135               140

Ser
145

<210> SEQ ID NO 57
<211> LENGTH: 138
<212> TYPE: PRT
<213> ORGANISM: Artificial Sequence
<220> FEATURE:
<223> OTHER INFORMATION: T2- 6C heavy chain

<400> SEQUENCE: 57

Met Ala Gln Met Gln Leu Val Glu Ser Gly Gly Gly Leu Val Gln Pro
1               5                  10                 15

Gly Arg Ser Leu Arg Leu Ser Cys Ala Ala Ser Gly Phe Thr Phe Asp
```

```
                    20                  25                  30
Asp Tyr Ala Ile His Trp Val Arg Gln Ala Pro Gly Lys Gly Leu Glu
            35                  40                  45
Trp Val Ser Gly Ile Ser Trp Asn Ser Glu Ile Val Gly Tyr Gly Asp
        50                  55                  60
Ser Val Lys Gly Arg Phe Thr Ile Ser Arg Asp Asn Ala Lys Asn Ser
65                  70                  75                  80
Leu Asp Leu Gln Met Asn Ser Leu Arg Ala Glu Asp Thr Ala Val Tyr
                85                  90                  95
Tyr Cys Ala Arg Gly Ser Ser Gly Arg Ala Phe Asp Ile Trp Gly Gln
            100                 105                 110
Gly Thr Met Val Thr Val Ser Ser Gly Leu Gly Gly Leu Gly Gly Gly
        115                 120                 125
Gly Ser Gly Gly Gly Gly Ser Gly Gly Ser
    130                 135

<210> SEQ ID NO 58
<211> LENGTH: 11
<212> TYPE: PRT
<213> ORGANISM: Artificial Sequence
<220> FEATURE:
<223> OTHER INFORMATION: T1-11G VL CDR 1

<400> SEQUENCE: 58

Arg Ala Ser Gln Ser Ile Ser Lys Trp Leu Ala
1               5                   10

<210> SEQ ID NO 59
<211> LENGTH: 16
<212> TYPE: PRT
<213> ORGANISM: Artificial Sequence
<220> FEATURE:
<223> OTHER INFORMATION: T1-12C VL CDR 1

<400> SEQUENCE: 59

Arg Ser Ser Gln Ser Leu Val Tyr Ser Asp Gly Asn Thr Tyr Leu Asn
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: T1-9F VL CDR 1

<400> SEQUENCE: 60

Arg Ser Ser Gln Ser Leu Val His Ser Asn Gly Asn Thr Tyr Leu Thr
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: T2-8F VL CDR 1

<400> SEQUENCE: 61

Arg Ser Ser Gln Ser Leu Leu His Ser Asn Gly Tyr Asn Tyr Leu Asp
1               5                   10                  15

<210> SEQ ID NO 62
<211> LENGTH: 14
<212> TYPE: PRT
<213> ORGANISM: Artificial Sequence
```

-continued

```
<220> FEATURE:
<223> OTHER INFORMATION: T2-12C VL CDR 1

<400> SEQUENCE: 62

Thr Gly Thr Ser Ser Asp Val Gly Gly Ser Ser Tyr Val Ser
1               5                   10

<210> SEQ ID NO 63
<211> LENGTH: 14
<212> TYPE: PRT
<213> ORGANISM: Artificial Sequence
<220> FEATURE:
<223> OTHER INFORMATION: T2-3A VL CDR 1

<400> SEQUENCE: 63

Thr Gly Thr Ser Thr Asp Ile Gly Gly Tyr Asn Tyr Val Ser
1               5                   10

<210> SEQ ID NO 64
<211> LENGTH: 14
<212> TYPE: PRT
<213> ORGANISM: Artificial Sequence
<220> FEATURE:
<223> OTHER INFORMATION: T2-7B VL CDR 1

<400> SEQUENCE: 64

Thr Gly Thr Ser Gly Asp Ile Gly Gly Phe Asn Tyr Val Ser
1               5                   10

<210> SEQ ID NO 65
<211> LENGTH: 13
<212> TYPE: PRT
<213> ORGANISM: Artificial Sequence
<220> FEATURE:
<223> OTHER INFORMATION: T2-6G VL CDR 1

<400> SEQUENCE: 65

Ser Gly Ser Asn Ser Asn Ile Gly Ser Asn Thr Val Asn
1               5                   10

<210> SEQ ID NO 66
<211> LENGTH: 11
<212> TYPE: PRT
<213> ORGANISM: Artificial Sequence
<220> FEATURE:
<223> OTHER INFORMATION: T2-10E VL CDR 1

<400> SEQUENCE: 66

Gln Ala Ser Gln Asp Ile Thr Asn Tyr Leu Asn
1               5                   10

<210> SEQ ID NO 67
<211> LENGTH: 11
<212> TYPE: PRT
<213> ORGANISM: Artificial Sequence
<220> FEATURE:
<223> OTHER INFORMATION: T2-6C VL CDR 1

<400> SEQUENCE: 67

Arg Ala Ser Gln Ser Ile Ser Thr Tyr Leu Asn
1               5                   10

<210> SEQ ID NO 68
<211> LENGTH: 11
<212> TYPE: PRT
<213> ORGANISM: Artificial Sequence
<220> FEATURE:
<223> OTHER INFORMATION: T1-5G VL CDR 1
```

```
<400> SEQUENCE: 68

Arg Ala Ser Gln Ser Ile Ser Ser Trp Leu Ala
1               5                   10

<210> SEQ ID NO 69
<211> LENGTH: 11
<212> TYPE: PRT
<213> ORGANISM: Artificial Sequence
<220> FEATURE:
<223> OTHER INFORMATION: T2-6A VL CDR 1

<400> SEQUENCE: 69

Arg Ala Ser Gln Gly Ile Ser Arg Trp Leu Ala
1               5                   10

<210> SEQ ID NO 70
<211> LENGTH: 11
<212> TYPE: PRT
<213> ORGANISM: Artificial Sequence
<220> FEATURE:
<223> OTHER INFORMATION: T2-12A VL CDR 1

<400> SEQUENCE: 70

Gln Gly Asp Ser Leu Arg Ser Tyr Tyr Ala Ser
1               5                   10

<210> SEQ ID NO 71
<211> LENGTH: 7
<212> TYPE: PRT
<213> ORGANISM: Artificial Sequence
<220> FEATURE:
<223> OTHER INFORMATION: T1-11G VL CDR 2

<400> SEQUENCE: 71

Ala Ala Ser Asn Leu Gln Ser
1               5

<210> SEQ ID NO 72
<211> LENGTH: 7
<212> TYPE: PRT
<213> ORGANISM: Artificial Sequence
<220> FEATURE:
<223> OTHER INFORMATION: T1-12C VL CDR 2

<400> SEQUENCE: 72

Lys Val Ser Asn Arg Asp Ser
1               5

<210> SEQ ID NO 73
<211> LENGTH: 7
<212> TYPE: PRT
<213> ORGANISM: Artificial Sequence
<220> FEATURE:
<223> OTHER INFORMATION: T1-9F VL CDR 2

<400> SEQUENCE: 73

Lys Ile Ser Lys Arg Phe Ser
1               5

<210> SEQ ID NO 74
<211> LENGTH: 7
<212> TYPE: PRT
<213> ORGANISM: Artificial Sequence
<220> FEATURE:
<223> OTHER INFORMATION: T2-8F VL CDR 2

<400> SEQUENCE: 74
```

```
Leu Gly Ser Lys Arg Ala Ala
1               5

<210> SEQ ID NO 75
<211> LENGTH: 7
<212> TYPE: PRT
<213> ORGANISM: Artificial Sequence
<220> FEATURE:
<223> OTHER INFORMATION: T2-12C VL CDR 2

<400> SEQUENCE: 75

Asp Val Thr Arg Arg Pro Ser
1               5

<210> SEQ ID NO 76
<211> LENGTH: 7
<212> TYPE: PRT
<213> ORGANISM: Artificial Sequence
<220> FEATURE:
<223> OTHER INFORMATION: T2-3A VL CDR 2

<400> SEQUENCE: 76

Asp Val Asn Asn Arg Pro Ser
1               5

<210> SEQ ID NO 77
<211> LENGTH: 7
<212> TYPE: PRT
<213> ORGANISM: Artificial Sequence
<220> FEATURE:
<223> OTHER INFORMATION: T2-7B VL CDR 2

<400> SEQUENCE: 77

Asp Val Ser Arg Arg Pro Ser
1               5

<210> SEQ ID NO 78
<211> LENGTH: 7
<212> TYPE: PRT
<213> ORGANISM: Artificial Sequence
<220> FEATURE:
<223> OTHER INFORMATION: T2-6G VL CDR 2

<400> SEQUENCE: 78

Gly His Asn Gln Arg Pro Ser
1               5

<210> SEQ ID NO 79
<211> LENGTH: 7
<212> TYPE: PRT
<213> ORGANISM: Artificial Sequence
<220> FEATURE:
<223> OTHER INFORMATION: T2-10E VL CDR 2

<400> SEQUENCE: 79

Ala Ala Ser Ser Leu His Thr
1               5

<210> SEQ ID NO 80
<211> LENGTH: 7
<212> TYPE: PRT
<213> ORGANISM: Artificial Sequence
<220> FEATURE:
<223> OTHER INFORMATION: T2-6C VL CDR 2

<400> SEQUENCE: 80

Gly Ala Thr Ser Leu Gln Ser
```

```
<210> SEQ ID NO 81
<211> LENGTH: 7
<212> TYPE: PRT
<213> ORGANISM: Artificial Sequence
<220> FEATURE:
<223> OTHER INFORMATION: T1-5G VL CDR 2

<400> SEQUENCE: 81

Lys Ala Ser Ser Leu Glu Ser
1               5

<210> SEQ ID NO 82
<211> LENGTH: 7
<212> TYPE: PRT
<213> ORGANISM: Artificial Sequence
<220> FEATURE:
<223> OTHER INFORMATION: T2-6A VL CDR 2

<400> SEQUENCE: 82

Ala Ala Ser Asn Leu Gln Ser
1               5

<210> SEQ ID NO 83
<211> LENGTH: 7
<212> TYPE: PRT
<213> ORGANISM: Artificial Sequence
<220> FEATURE:
<223> OTHER INFORMATION: T2-12A VL CDR 2

<400> SEQUENCE: 83

Gly Lys Asn Asn Arg Pro Ser
1               5

<210> SEQ ID NO 84
<211> LENGTH: 9
<212> TYPE: PRT
<213> ORGANISM: Artificial Sequence
<220> FEATURE:
<223> OTHER INFORMATION: T1-11G VL CDR 3

<400> SEQUENCE: 84

Leu Gln Ser Asn Ser Leu Pro Ile Thr
1               5

<210> SEQ ID NO 85
<211> LENGTH: 9
<212> TYPE: PRT
<213> ORGANISM: Artificial Sequence
<220> FEATURE:
<223> OTHER INFORMATION: T1-12C VL CDR 3

<400> SEQUENCE: 85

Met Gln Ser Leu Arg Thr Pro Leu Thr
1               5

<210> SEQ ID NO 86
<211> LENGTH: 9
<212> TYPE: PRT
<213> ORGANISM: Artificial Sequence
<220> FEATURE:
<223> OTHER INFORMATION: T1-9F VL CDR 3

<400> SEQUENCE: 86

Met Gln Leu Thr Gln Phe Pro Leu Thr
1               5
```

```
<210> SEQ ID NO 87
<211> LENGTH: 8
<212> TYPE: PRT
<213> ORGANISM: Artificial Sequence
<220> FEATURE:
<223> OTHER INFORMATION: T2-8F VL CDR 3

<400> SEQUENCE: 87

Met Gln Ala Leu Gln Thr Pro Thr
1               5

<210> SEQ ID NO 88
<211> LENGTH: 9
<212> TYPE: PRT
<213> ORGANISM: Artificial Sequence
<220> FEATURE:
<223> OTHER INFORMATION: T2-12C VL CDR 3

<400> SEQUENCE: 88

Ala Ser Tyr Ala Gly Ser His Tyr Leu
1               5

<210> SEQ ID NO 89
<211> LENGTH: 9
<212> TYPE: PRT
<213> ORGANISM: Artificial Sequence
<220> FEATURE:
<223> OTHER INFORMATION: T2-3A VL CDR 3

<400> SEQUENCE: 89

Ser Ser Tyr Thr Ser Ser Ser Phe Val
1               5

<210> SEQ ID NO 90
<211> LENGTH: 10
<212> TYPE: PRT
<213> ORGANISM: Artificial Sequence
<220> FEATURE:
<223> OTHER INFORMATION: T2-7B VL CDR 3

<400> SEQUENCE: 90

Ala Ser Tyr Ala Gly Thr Lys Phe Trp Leu
1               5                   10

<210> SEQ ID NO 91
<211> LENGTH: 13
<212> TYPE: PRT
<213> ORGANISM: Artificial Sequence
<220> FEATURE:
<223> OTHER INFORMATION: T2-6G VL CDR 3

<400> SEQUENCE: 91

Ala Ser Trp Asp Asp Thr Val Ser Gly Pro Lys Trp Val
1               5                   10

<210> SEQ ID NO 92
<211> LENGTH: 9
<212> TYPE: PRT
<213> ORGANISM: Artificial Sequence
<220> FEATURE:
<223> OTHER INFORMATION: T2-10E VL CDR 3

<400> SEQUENCE: 92

Gln Gln Ser His Ser Pro Pro Phe Thr
1               5

<210> SEQ ID NO 93
```

```
<211> LENGTH: 9
<212> TYPE: PRT
<213> ORGANISM: Artificial Sequence
<220> FEATURE:
<223> OTHER INFORMATION: T2-6C VL CDR 3

<400> SEQUENCE: 93

Gln Gln Ser Tyr Asn Leu Pro Arg Thr
1               5

<210> SEQ ID NO 94
<211> LENGTH: 9
<212> TYPE: PRT
<213> ORGANISM: Artificial Sequence
<220> FEATURE:
<223> OTHER INFORMATION: T1-5G VL CDR 3

<400> SEQUENCE: 94

Gln Gln Phe Asn Asn Asn Leu Phe Ser
1               5

<210> SEQ ID NO 95
<211> LENGTH: 9
<212> TYPE: PRT
<213> ORGANISM: Artificial Sequence
<220> FEATURE:
<223> OTHER INFORMATION: T2-6A VL CDR 3

<400> SEQUENCE: 95

Gln Gln Ala Asn Ser Phe Pro Leu Thr
1               5

<210> SEQ ID NO 96
<211> LENGTH: 11
<212> TYPE: PRT
<213> ORGANISM: Artificial Sequence
<220> FEATURE:
<223> OTHER INFORMATION: T2-12A VL CDR 3

<400> SEQUENCE: 96

Ser Ser Arg Asp Ser Ser Gly Asn His Leu Val
1               5                   10

<210> SEQ ID NO 97
<211> LENGTH: 131
<212> TYPE: PRT
<213> ORGANISM: Artificial Sequence
<220> FEATURE:
<223> OTHER INFORMATION: T1-11G light chain

<400> SEQUENCE: 97

Ser Gly Val Gly Ser Asp Ile Gln Met Thr Gln Ser Pro Ser Ser Val
1               5                   10                  15

Ser Ala Ser Val Gly Asp Arg Val Thr Ile Thr Cys Arg Ala Ser Gln
            20                  25                  30

Ser Ile Ser Lys Trp Leu Ala Trp Tyr Gln Gln Lys Pro Gly Lys Ala
        35                  40                  45

Pro Lys Leu Leu Ile Tyr Ala Ala Ser Asn Leu Gln Ser Gly Val Pro
    50                  55                  60

Ser Arg Phe Asn Gly Ser Gly Ser Gly Thr Asp Phe Thr Leu Thr Ile
65                  70                  75                  80

Asn Ser Leu Gln Pro Glu Asp Phe Ala Thr Tyr Tyr Cys Leu Gln Ser
                85                  90                  95

Asn Ser Leu Pro Ile Thr Phe Gly Gln Gly Thr Arg Leu Asp Ile Lys
            100                 105                 110
```

Arg Gly Gly Ala Ser Leu Val Glu Phe Glu Gln Lys Leu Ile Ser Glu
        115                 120                 125

Glu Asp Leu
    130

<210> SEQ ID NO 98
<211> LENGTH: 131
<212> TYPE: PRT
<213> ORGANISM: Artificial Sequence
<220> FEATURE:
<223> OTHER INFORMATION: T2- 6A light chain

<400> SEQUENCE: 98

Ser Gly Val Gly Ser Asp Ile Gln Met Thr Gln Ser Pro Ser Ser Val
1               5                   10                  15

Ser Ala Ser Val Gly Asp Arg Val Thr Ile Thr Cys Arg Ala Ser Gln
                20                  25                  30

Gly Ile Ser Arg Trp Leu Ala Trp Tyr Gln Gln Lys Pro Gly Lys Ala
            35                  40                  45

Pro Lys Leu Leu Ile Tyr Ala Ala Ser Asn Leu Gln Ser Gly Val Pro
    50                  55                  60

Ser Arg Phe Ser Gly Ser Gly Ser Gly Thr Asp Phe Thr Leu Thr Ile
65                  70                  75                  80

Asn Ser Leu Gln Pro Asp Asp Phe Ala Ile Tyr Tyr Cys Gln Gln Ala
                85                  90                  95

Asn Ser Phe Pro Leu Thr Phe Gly Pro Gly Thr Lys Val Asp Ile Lys
            100                 105                 110

Arg Gly Gly Ala Ser Leu Val Glu Phe Glu Gln Lys Leu Ile Ser Glu
        115                 120                 125

Glu Asp Leu
    130

<210> SEQ ID NO 99
<211> LENGTH: 136
<212> TYPE: PRT
<213> ORGANISM: Artificial Sequence
<220> FEATURE:
<223> OTHER INFORMATION: T1-12C light chain

<400> SEQUENCE: 99

Ser Gly Val Gly Ser Asp Ile Val Met Thr Gln Thr Pro Leu Ser Leu
1               5                   10                  15

Ser Val Thr Pro Gly Gln Pro Ala Ser Ile Ser Cys Arg Ser Ser Gln
                20                  25                  30

Ser Leu Val Tyr Ser Asp Gly Asn Thr Tyr Leu Asn Trp Phe His Gln
            35                  40                  45

Arg Pro Gly Gln Pro Pro Arg Arg Leu Ile Tyr Lys Val Ser Asn Arg
    50                  55                  60

Asp Ser Gly Val Pro Gly Arg Phe Ser Gly Ser Gly Ser Gly Thr Asp
65                  70                  75                  80

Phe Thr Leu Arg Ile Ser Arg Val Glu Ala Glu Asp Val Gly Val Tyr
                85                  90                  95

Tyr Cys Met Gln Ser Leu Arg Thr Pro Leu Thr Phe Gly Gly Gly Thr
            100                 105                 110

Lys Val Asp Ile Lys Arg Gly Gly Ala Ser Leu Val Glu Phe Glu Gln
        115                 120                 125

Lys Leu Ile Ser Glu Glu Asp Leu
    130                 135

<210> SEQ ID NO 100
<211> LENGTH: 136
<212> TYPE: PRT
<213> ORGANISM: Artificial Sequence
<220> FEATURE:
<223> OTHER INFORMATION: T1- 9F light chain

<400> SEQUENCE: 100

```
Ser Gly Val Gly Ser Asp Ile Val Met Thr Gln Thr Pro Leu Ser Ser
1               5                   10                  15

Pro Val Thr Leu Gly Gln Pro Ala Ser Ile Ser Cys Arg Ser Ser Gln
            20                  25                  30

Ser Leu Val His Ser Asn Gly Asn Thr Tyr Leu Thr Trp Leu Gln Gln
        35                  40                  45

Arg Pro Gly Gln Pro Pro Arg Leu Leu Ile Tyr Lys Ile Ser Lys Arg
    50                  55                  60

Phe Ser Gly Val Pro Asp Arg Phe Ser Gly Ser Gly Ala Gly Thr Asp
65                  70                  75                  80

Phe Thr Leu Lys Ile Ser Arg Val Glu Ala Glu Asp Val Gly Val Tyr
                85                  90                  95

Tyr Cys Met Gln Leu Thr Gln Phe Pro Leu Thr Phe Gly Gly Gly Thr
            100                 105                 110

Lys Val Glu Ile Lys Arg Gly Gly Ala Ser Leu Val Glu Phe Glu Gln
        115                 120                 125

Lys Leu Ile Ser Glu Glu Asp Leu
    130                 135
```

<210> SEQ ID NO 101
<211> LENGTH: 136
<212> TYPE: PRT
<213> ORGANISM: Artificial Sequence
<220> FEATURE:
<223> OTHER INFORMATION: T2-12F light chain

<400> SEQUENCE: 101

```
Ser Gly Val Gly Ser Asp Ile Val Met Thr Gln Thr Pro Leu Ser Ser
1               5                   10                  15

Pro Val Thr Leu Gly Gln Pro Ala Ser Ile Ser Cys Arg Ser Ser Gln
            20                  25                  30

Ser Leu Val His Ser Asn Gly Asn Thr Tyr Leu Thr Trp Leu Gln Gln
        35                  40                  45

Arg Pro Gly Gln Pro Pro Arg Leu Leu Ile Tyr Lys Ile Ser Lys Arg
    50                  55                  60

Phe Ser Gly Val Pro Asp Arg Phe Ser Gly Ser Gly Ala Gly Thr Asp
65                  70                  75                  80

Phe Thr Leu Lys Ile Ser Arg Val Glu Ala Glu Asp Val Gly Val Tyr
                85                  90                  95

Tyr Cys Met Gln Leu Thr Gln Phe Pro Leu Thr Phe Gly Gly Gly Thr
            100                 105                 110

Lys Val Glu Ile Lys Arg Gly Gly Ala Ser Leu Val Glu Phe Glu Gln
        115                 120                 125

Lys Leu Ile Ser Glu Glu Asp Leu
    130                 135
```

<210> SEQ ID NO 102
<211> LENGTH: 135
<212> TYPE: PRT
<213> ORGANISM: Artificial Sequence -continued

```
<220> FEATURE:
<223> OTHER INFORMATION: T2- 8F light chain

<400> SEQUENCE: 102

Ser Gly Val Gly Ser Asp Ile Val Met Thr Gln Thr Pro Leu Ser Leu
1               5                   10                  15

Pro Val Thr Pro Gly Glu Pro Ala Ser Ile Ser Cys Arg Ser Ser Gln
            20                  25                  30

Ser Leu Leu His Ser Asn Gly Tyr Asn Tyr Leu Asp Trp Tyr Leu Gln
        35                  40                  45

Lys Pro Gly Gln Ser Pro Gln Leu Leu Ile Tyr Leu Gly Ser Lys Arg
    50                  55                  60

Ala Ala Gly Val Pro Asp Arg Phe Ser Gly Ser Gly Ser Gly Thr Asp
65                  70                  75                  80

Phe Thr Leu Lys Ile Ser Arg Val Glu Ala Glu Asp Val Gly Val Tyr
                85                  90                  95

Tyr Cys Met Gln Ala Leu Gln Thr Pro Thr Phe Gly Gln Gly Thr Lys
            100                 105                 110

Val Asp Ile Lys Arg Gly Gly Ala Ser Leu Val Glu Phe Glu Gln Lys
        115                 120                 125

Leu Ile Ser Glu Glu Asp Leu
    130                 135

<210> SEQ ID NO 103
<211> LENGTH: 132
<212> TYPE: PRT
<213> ORGANISM: Artificial Sequence
<220> FEATURE:
<223> OTHER INFORMATION: T2-12A light chain

<400> SEQUENCE: 103

Ser Gly Val Gly Ser Tyr Glu Leu Thr Gln Asp Pro Ala Val Ser
1               5                   10                  15

Val Ala Leu Gly Gln Thr Val Arg Ile Thr Cys Gln Gly Asp Ser Leu
            20                  25                  30

Arg Ser Tyr Tyr Ala Ser Trp Tyr Gln Gln Lys Pro Gly Gln Ala Pro
        35                  40                  45

Val Leu Val Ile Tyr Gly Lys Asn Asn Arg Pro Ser Gly Ile Pro Asp
    50                  55                  60

Arg Phe Ser Gly Ser Asn Ser Gly Asn Thr Ala Ser Leu Thr Ile Thr
65                  70                  75                  80

Gly Thr Gln Ala Glu Asp Glu Ala Val Tyr Tyr Cys Ser Ser Arg Asp
                85                  90                  95

Ser Ser Gly Asn His Leu Val Phe Gly Gly Gly Thr Lys Leu Thr Val
            100                 105                 110

Leu Gly Gly Gly Ala Ser Leu Val Glu Phe Glu Gln Lys Leu Ile Ser
        115                 120                 125

Glu Glu Asp Leu
    130

<210> SEQ ID NO 104
<211> LENGTH: 133
<212> TYPE: PRT
<213> ORGANISM: Artificial Sequence
<220> FEATURE:
<223> OTHER INFORMATION: T2-12C light chain

<400> SEQUENCE: 104

Ser Gly Val Gly Ser Gln Phe Ala Leu Thr Gln Pro Arg Ser Val Ser
```

```
                    1               5                  10                 15
Gly Ser Pro Gly Gln Ser Val Thr Ile Ser Cys Thr Gly Thr Ser Ser
                   20                 25                 30

Asp Val Gly Gly Ser Ser Tyr Val Ser Trp Tyr Gln Gln His Pro Gly
                   35                 40                 45

Lys Ala Pro Lys Leu Met Ile Tyr Asp Val Thr Arg Arg Pro Ser Gly
         50                 55                 60

Val Pro Asp Arg Phe Ser Gly Ser Lys Ser Asp Asn Thr Ala Ser Leu
 65                 70                 75                 80

Thr Ile Ser Gly Leu Gln Pro Lys Asp Glu Ala Asp Tyr Tyr Cys Ala
                 85                 90                 95

Ser Tyr Ala Gly Ser His Tyr Leu Phe Gly Thr Gly Thr Lys Val Thr
                100                105                110

Val Leu Gly Gly Gly Ala Ser Leu Val Glu Phe Glu Gln Lys Leu Ile
             115                120                125

Ser Glu Glu Asp Leu
         130
```

<210> SEQ ID NO 105
<211> LENGTH: 133
<212> TYPE: PRT
<213> ORGANISM: Artificial Sequence
<220> FEATURE:
<223> OTHER INFORMATION: T2- 3A light chain

<400> SEQUENCE: 105

```
Ser Gly Val Gly Ser Gln Ser Ala Leu Thr Gln Pro Ala Ser Val Ser
 1               5                  10                 15

Gly Ser Pro Gly Gln Ser Ile Thr Ile Ser Cys Thr Gly Thr Ser Thr
                   20                 25                 30

Asp Ile Gly Gly Tyr Asn Tyr Val Ser Trp Tyr Gln Gln His Pro Gly
                   35                 40                 45

Lys Ala Pro Lys Leu Met Ile Ser Asp Val Asn Asn Arg Pro Ser Gly
         50                 55                 60

Val Ser His Arg Phe Ser Gly Ser Lys Ser Gly Asn Thr Ala Ser Leu
 65                 70                 75                 80

Thr Ile Ser Gly Leu Gln Ser Glu Asp Glu Ala Asp Tyr Tyr Cys Ser
                 85                 90                 95

Ser Tyr Thr Ser Ser Ser Phe Val Phe Gly Thr Gly Thr Lys Val Thr
                100                105                110

Val Leu Gly Gly Gly Ala Ser Leu Val Glu Phe Glu Gln Lys Leu Ile
             115                120                125

Ser Glu Glu Asp Leu
         130
```

<210> SEQ ID NO 106
<211> LENGTH: 134
<212> TYPE: PRT
<213> ORGANISM: Artificial Sequence
<220> FEATURE:
<223> OTHER INFORMATION: T2- 7B light chain

<400> SEQUENCE: 106

```
Ser Gly Val Gly Ser Gln Ser Ala Leu Thr Gln Pro Arg Ser Val Ser
 1               5                  10                 15

Gly Ser Pro Gly Gln Ser Val Thr Ile Ser Cys Thr Gly Thr Ser Gly
                   20                 25                 30

Asp Ile Gly Gly Phe Asn Tyr Val Ser Trp Tyr Gln Gln His Pro Gly
```

```
                35                  40                  45
Arg Ala Pro Lys Ile Ile Ile Tyr Asp Val Ser Arg Arg Pro Ser Gly
     50                  55                  60

Val Pro Asn Arg Phe Ser Ala Ser Lys Ser Gly Asn Thr Ala Ser Leu
 65                  70                  75                  80

Thr Val Ser Gly Leu Gln Pro Glu Asp Glu Ala Thr Tyr Phe Cys Ala
                 85                  90                  95

Ser Tyr Ala Gly Thr Lys Phe Trp Leu Phe Gly Gly Gly Thr Lys Leu
             100                 105                 110

Thr Val Leu Gly Gly Gly Ala Ser Leu Val Glu Phe Glu Gln Lys Leu
         115                 120                 125

Ile Ser Glu Glu Asp Leu
        130

<210> SEQ ID NO 107
<211> LENGTH: 136
<212> TYPE: PRT
<213> ORGANISM: Artificial Sequence
<220> FEATURE:
<223> OTHER INFORMATION: T2- 6G light chain

<400> SEQUENCE: 107

Ser Gly Val Gly Ser Gln Ser Ala Leu Thr Gln Pro Pro Ser Ala Ser
 1               5                  10                  15

Gly Thr Pro Gly Gln Arg Val Thr Ile Ser Cys Ser Gly Ser Asn Ser
             20                  25                  30

Asn Ile Gly Ser Asn Thr Val Asn Trp Tyr Gln Gln Phe Pro Gly Lys
         35                  40                  45

Ala Pro Gln Leu Leu Ile Phe Gly His Asn Gln Arg Pro Ser Gly Val
     50                  55                  60

Pro Asp Arg Phe Ser Gly Ser Lys Ser Gly Thr Ser Ala Ser Leu Ser
 65                  70                  75                  80

Ile Ser Gly Leu Gln Ser Glu Asp Glu Ala His Tyr Tyr Cys Ala Ser
                 85                  90                  95

Trp Asp Asp Thr Val Ser Gly Pro Lys Trp Val Phe Gly Gly Gly Thr
             100                 105                 110

Lys Leu Thr Val Leu Gly Gly Gly Ala Ser Leu Val Glu Phe Glu Gln
         115                 120                 125

Lys Leu Ile Ser Glu Glu Asp Leu
     130                 135

<210> SEQ ID NO 108
<211> LENGTH: 131
<212> TYPE: PRT
<213> ORGANISM: Artificial Sequence
<220> FEATURE:
<223> OTHER INFORMATION: T2-10E light chain

<400> SEQUENCE: 108

Ser Gly Val Gly Ser Asp Ile Gln Met Thr Gln Ser Ser Ser Ser Leu
 1               5                  10                  15

Ser Ala Ser Ile Gly Asp Arg Val Thr Ile Thr Cys Gln Ala Ser Gln
             20                  25                  30

Asp Ile Thr Asn Tyr Leu Asn Trp Tyr Gln Gln Lys Pro Gly Lys Ala
         35                  40                  45

Pro Lys Leu Leu Ile Tyr Ala Ala Ser Ser Leu His Thr Gly Val Pro
     50                  55                  60

Ser Arg Phe Ser Gly Ser Gly Ser Gly Thr Asp Phe Thr Leu Thr Ile
```

```
                65                  70                  75                  80
Thr Asn Met Leu Pro Glu Asp Phe Ala Thr Tyr Tyr Cys Gln Gln Ser
                    85                  90                  95

His Ser Pro Pro Phe Thr Phe Gly Gly Gly Thr Lys Val Asp Ile Lys
                100                 105                 110

Arg Gly Gly Ala Ser Leu Val Glu Phe Glu Gln Lys Leu Ile Ser Glu
            115                 120                 125

Glu Asp Leu
        130

<210> SEQ ID NO 109
<211> LENGTH: 131
<212> TYPE: PRT
<213> ORGANISM: Artificial Sequence
<220> FEATURE:
<223> OTHER INFORMATION: T2- 6C light chain

<400> SEQUENCE: 109

Ser Gly Val Gly Ser Asp Ile Gln Met Thr Gln Ser Pro Ser Ser Val
1               5                   10                  15

Ser Ala Ser Val Gly Asp Arg Ile Thr Ile Thr Cys Arg Ala Ser Gln
                20                  25                  30

Ser Ile Ser Thr Tyr Leu Asn Trp Tyr Gln Gln Lys Pro Gly Lys Ala
            35                  40                  45

Pro Lys Leu Leu Ile Tyr Gly Ala Thr Ser Leu Gln Ser Gly Val Pro
        50                  55                  60

Ser Arg Phe Ser Gly Ser Gly Ser Gly Thr Asp Phe Thr Leu Thr Ile
65                  70                  75                  80

Arg Gly Leu Gln Pro Asp Asp Phe Gly Thr Tyr Tyr Cys Gln Gln Ser
                    85                  90                  95

Tyr Asn Leu Pro Arg Thr Phe Gly Gln Gly Thr Lys Leu Asp Ile Lys
                100                 105                 110

Arg Gly Gly Ala Ser Leu Val Glu Phe Glu Gln Lys Leu Ile Ser Glu
            115                 120                 125

Glu Asp Leu
        130

<210> SEQ ID NO 110
<211> LENGTH: 50
<212> TYPE: DNA
<213> ORGANISM: Artificial Sequence
<220> FEATURE:
<223> OTHER INFORMATION: NATVH1-2

<400> SEQUENCE: 110
ttggtggcca cagcggccga tgtccactcg cagatgcagc tggtgcagtc            50

<210> SEQ ID NO 111
<211> LENGTH: 50
<212> TYPE: DNA
<213> ORGANISM: Artificial Sequence
<220> FEATURE:
<223> OTHER INFORMATION: NATVH1-2

<400> SEQUENCE: 111
ttggtggcca cagcggccga tgtccactcg cagatgcagc tggtgcagtc            50

<210> SEQ ID NO 112
<211> LENGTH: 50
<212> TYPE: DNA
<213> ORGANISM: Artificial Sequence
```

```
<220> FEATURE:
<223> OTHER INFORMATION: NATVH3-2

<400> SEQUENCE: 112
ttggtggcca cagcggccga tgtccactcg caggtgcagc tggtggagtc        50

<210> SEQ ID NO 113
<211> LENGTH: 50
<212> TYPE: DNA
<213> ORGANISM: Artificial Sequence
<220> FEATURE:
<223> OTHER INFORMATION: NATVH3-2

<400> SEQUENCE: 113
ttggtggcca cagcggccga tgtccactcg caggtgcagc tggtggagtc        50

<210> SEQ ID NO 114
<211> LENGTH: 26
<212> TYPE: DNA
<213> ORGANISM: Artificial Sequence
<220> FEATURE:
<223> OTHER INFORMATION: NATJH-ALL

<400> SEQUENCE: 114
gaggaggcta gctgaggaga cggtga                                  26

<210> SEQ ID NO 115
<211> LENGTH: 50
<212> TYPE: DNA
<213> ORGANISM: Artificial Sequence
<220> FEATURE:
<223> OTHER INFORMATION: NATVL4

<400> SEQUENCE: 115
ttggtggcca cagcggccga tgtccactcg cagtctgccc tgactcagcc        50

<210> SEQ ID NO 116
<211> LENGTH: 50
<212> TYPE: DNA
<213> ORGANISM: Artificial Sequence
<220> FEATURE:
<223> OTHER INFORMATION: NATVK1-1

<400> SEQUENCE: 116
ttggtggcca cagcggccga tgtccactcg gacatccaga tgacccagtc        50

<210> SEQ ID NO 117
<211> LENGTH: 50
<212> TYPE: DNA
<213> ORGANISM: Artificial Sequence
<220> FEATURE:
<223> OTHER INFORMATION: NATVL4

<400> SEQUENCE: 117
ttggtggcca cagcggccga tgtccactcg cagtctgccc tgactcagcc        50

<210> SEQ ID NO 118
<211> LENGTH: 53
<212> TYPE: DNA
<213> ORGANISM: Artificial Sequence
<220> FEATURE:
<223> OTHER INFORMATION: NATVK3

<400> SEQUENCE: 118
ttggtggcca cagcggccga tgtccactcg gatattgtga tgacccagac tcc    53
```

```
<210> SEQ ID NO 119
<211> LENGTH: 33
<212> TYPE: DNA
<213> ORGANISM: Artificial Sequence
<220> FEATURE:
<223> OTHER INFORMATION: NATJL1-R

<400> SEQUENCE: 119
gaggagagat cttaggacgg tgaccttggt ccc                                33

<210> SEQ ID NO 120
<211> LENGTH: 30
<212> TYPE: DNA
<213> ORGANISM: Artificial Sequence
<220> FEATURE:
<223> OTHER INFORMATION: NATJK-R5

<400> SEQUENCE: 120
gaggagagat cttttgattt ccagcttggt                                    30

<210> SEQ ID NO 121
<211> LENGTH: 33
<212> TYPE: DNA
<213> ORGANISM: Artificial Sequence
<220> FEATURE:
<223> OTHER INFORMATION: NATJL2-R

<400> SEQUENCE: 121
gaggagagat cttaggacgg tcagcttggt ccc                                33
```